(12) United States Patent
Okuzumi et al.

(10) Patent No.: US 7,250,516 B2
(45) Date of Patent: Jul. 31, 2007

(54) PHENYLALANINE DERIVATIVES

(75) Inventors: Tatsuya Okuzumi, Kawasaki (JP);
Kazuyuki Sagi, Kawasaki (JP);
Toshihiko Yoshimura, Kawasaki (JP);
Yuji Tanaka, Kawasaki (JP); Eiji Nakanishi, Kawasaki (JP); Miho Ono, Kawasaki (JP); Masahiro Murata, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 476 days.

(21) Appl. No.: 10/866,260

(22) Filed: Jun. 14, 2004

(65) Prior Publication Data

US 2004/0235848 A1  Nov. 25, 2004

Related U.S. Application Data

(63) Continuation of application No. PCT/JP02/13070, filed on Dec. 13, 2002.

(30) Foreign Application Priority Data

Dec. 13, 2001 (JP) .............................. 2001-380655
Feb. 15, 2002 (JP) .............................. 2002-039070

(51) Int. Cl.
*C07D 215/38* (2006.01)
*A61K 31/47* (2006.01)

(52) U.S. Cl. ..................... 546/157; 546/153; 514/311; 514/312; 514/314

(58) Field of Classification Search ................ 546/157, 546/153; 514/311, 312, 314
See application file for complete search history.

(56) References Cited

U.S. PATENT DOCUMENTS

| | | | |
|---|---|---|---|
| 6,229,011 B1 * | 5/2001 | Chen et al. ................. | 544/171 |
| 6,455,550 B1 * | 9/2002 | Chen et al. ................. | 514/341 |
| 6,610,710 B2 | 8/2003 | Tanaka et al. | |
| 6,855,706 B2 * | 2/2005 | Tanaka et al. ......... | 514/210.17 |
| 2004/0235848 A1 | 11/2004 | Okuzumi et al. | |

FOREIGN PATENT DOCUMENTS

| IN | 190990 | * | 9/2003 |
|---|---|---|---|
| WO | WO 99/10312 | | 3/1999 |
| WO | WO 99/10313 | | 3/1999 |
| WO | WO 99/35163 | | 7/1999 |
| WO | WO 99/36393 | | 7/1999 |
| WO | WO 99/37618 | | 7/1999 |
| WO | WO 01/36376 | | 5/2001 |
| WO | WO 01/42215 A1 | | 6/2001 |
| WO | WO 01/42225 A2 | | 6/2001 |
| WO | WO 02/16329 | | 2/2002 |
| WO | WO 02/28830 | | 4/2002 |

OTHER PUBLICATIONS

Fera,I J of Clin Invest, vol. 116 (3), pp. 715-723, Mar. 2006.*
Engelhardt, Eur J Immunol, vol. 35, pp. 2268-2273, 2005.*
Xiaoli, J of Leukocyte Biology, vol. 75, pp. 1016-1021, Jun. 2004.*
Sandbom, American J of Gastroenterology, vol. 98(11), pp. 2372-2382, 2003.*
Foster, J Allergy Clin Immunol, vol. 98, No. 6 part 2, pp. S270-S277, 1996.*
Dostal, V., et al., "Determination of Acids and Their Strength in Isobutyl Methyl Ketone," Collection of Czechoslovak Chemical Communications, vol. 47, No. 4, 1982, pp. 1203-1215, XP002405365.
U.S. Appl. No. 11/018,226, filed Dec. 22, 2004, Sagi et al.
U.S. Appl. No. 10/866,260, filed Jun. 14, 2004, Okuzumi et al.
U.S. Appl. No. 10/866,260, filed Jun. 14, 2004, Okuzumi et al.
U.S. Appl. No. 10/921,929, filed Aug. 20, 2004, Sagi et al.
J.W. Tilley, et al., "Imide and Lactam Derivatives of N-Benzyl-pyroglutamyl-L-Phenylalanine as VCAM/VLA-4 Antagonists", Bioorganic & Medicinal Chemistry Letters, 11, 2001, pp. 1-4.
U.S. Appl. No. 10/300,856, filed Nov. 21, 2002, Makino et al.
U.S. Appl. No. 10/150,067, filed May 20, 2002, Tanaka et al.
U.S. Appl. No. 10/252,003, filed Sep. 23, 2002, Suzuki et al.
U.S. Appl. No. 10/402,006, filed Mar. 31, 2003, Suzuki et al.
U.S. Appl. No. 10/763,237, filed Jan. 26, 2004, Chiba et al.

* cited by examiner

*Primary Examiner*—D. Margaret Seaman
(74) *Attorney, Agent, or Firm*—Oblon, Spivak, McClelland, Maier & Neustadt, P.C.

(57) ABSTRACT

Phenylalanine derivatives of the following formula, analogues thereof and pharmaceutically acceptable salts thereof have an antagonistic activity to α4 integrin. They are used as therapeutic agents or preventive agents for various diseases concerning α4 integrin in which α4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

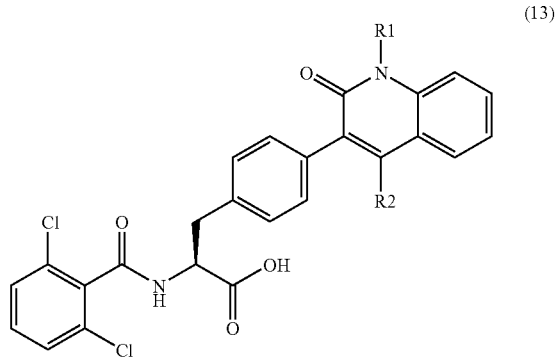

(13)

wherein R1 is a methyl group and R2 is a methoxy group.

14 Claims, No Drawings

PHENYLALANINE DERIVATIVES

This application is a continuation of PCT/JP02/13070, filed on Dec. 13, 2002. which claims priority to JP 2001-380655, filed on Dec. 13, 2001, and JP 2002-039070, filed on Feb. 15, 2002.

BACKGROUND OF THE INVENTION

The present invention relates to new phenylalanine derivatives and the use of the phenylalanine derivatives as medicines. The present invention also relates to the compounds usable as therapeutic agents or preventive agents for inflammatory diseases in which α4 integrin-depending adhesion process participates in the pathology. It was reported that α4 integrins participate in rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection. The compounds of the present invention having an antagonistic effect on the α4 integrins are usable as therapeutic agents or preventive agents for the above-described diseases.

In the inflammatory reactions, it is generally understood that when a microorganism invades a tissue or when the tissue is injured, leukocytes play an important role for the exclusion of the microorganism or for the repair of the injured tissue. It is also widely understood that in such cases, leukocytes usually circulating in the blood must pass through the vascular wall and be newly supplied to the injured tissue. It has been elucidated that the infiltration of the leukocytes from the blood vessel into the tissue is carried out by integrin molecules which are a group of heterodimeric proteins expressing on the leukocytes. The integrin molecules are classified into at least 8 subfamilies (β1 through β8 subfamilies) depending on the β chains thereof. Known typical subfamilies are β1 and β3 subfamilies involved in the adhesion of cell ingredients to the extracellular matrix such as collagen and fibronectin; β2 subfamily involved in cell-to-cell adhesion in the immune system; and β7 subfamily which mainly participates in the infiltration of leukocytes into mucosal tissues (Shimizu et al., Adv. Immunol. 72: 325-380, 1999). As for the above-described α4 integrins, two kinds of molecules thereof are known. They are VLA-4 (very late antigen-4) molecule belonging to the β1 subfamily and comprising α4β1 chain and LPAM-1 (lymphocyte Peyer's patch HEV adhesion molecule-1) molecule belonging to the β7 subfamily and comprising α4β7 chain. Usually most of leukocytes circulating in the blood have only a low adhesion affinity for the vascular-endothelium cells and they cannot move out of the blood vessel. However, lymphocytes mainly comprising T cells and B cells are capable of moving out of the blood vessel by a so-called lymphocyte homing phenomenon wherein they move from the blood into the lymphoid tissue through the blood vessel wall and then they return into the blood through the lymphatic vessel under the physiological conditions. It is known that LPAM-1 molecules participate in the lymphocyte homing into the lymphoid tissue of an intestinal tract such as Peyer's patch (Butcher et al., Adv. Immunol. 72: 209-253, 1999). On the other hand, when an inflammation occurs, the vascular-endothelium cells are activated by cytokine and chemokine released from the inflamed tissue, the expression of a group of cell surface antigens (adhesion molecules) participating in the adhesion of leukocytes to the vascular-endothelium cells is caused, and a lot of leukocytes infiltrate out of the blood vessel toward the inflamed tissue through the adhesion molecules.

As the cell surface antigens on the vascular-endothelium cells participating in the adhesion of the leukocytes, there have been known E-selectin (adhesion molecule mainly participating in the adhesion of neutrophils), ICAM-1 and VCAM-1 mainly participating in the adhesion of lymphocytes, and MAdCAM-1 mainly participating in the adhesion of lymphocytes in the lymphoid tissue of an intestinal tract such as Peyer's patch (Shimizu et al., Adv. Immunol. 72: 325-380, 1999). It was reported that in those adhesion molecules, VCAM-1 acts as a ligand of both VLA-4 and LPAM-1 and that MAdCAM-1 acts as the ligand of LPAM-1. As a ligand of both VLA-4 and LPAM-1, fibronectin which is a kind of extracellular matrix is also known (Shimizu et al., Adv. Immunol. 72: 325-380, 1999). The β1 integrin subfamily to which VLA-4 belongs comprises at least 6 integrins (VLA-1 to VLA-6) using extracellular matrixes such as fibronectin, collagen and laminin as the ligands. Many of integrins using extracellular matrixes as the ligands, such as VLA-5, β3 subfamily and β5 subfamily, recognize arginine-glycine-aspartic acid (RGD) sequence in fibronectin, vitronectin, tenascin and osteopontin. On the other hand, in the interaction of VLA-4 and fibronectin, the RGD sequence does not participate but a CS-1 peptide segment comprising leucine-aspartic acid-valine (LDV) as the core sequence participates (Pulido et al., J. Biol. Chem. 266: 10241-10245, 1991). Clements et al. found a sequence similar to LDV in amino acid sequences of VCAM-1 and MAdCAM-1. It has been elucidated that a variant obtained by partially modifying the CS-1-like sequence of VCAM-1 and MAdCAM-1 molecules cannot interact to VLA-4 or LPAM-1 (Clements et al., J. Cell Sci. 107: 2127-2135, 1994, Vonderheide et al., J. Cell. Biol. 125: 215-222, 1994, Renz et al., J. Cell. Biol. 125: 1395-1406, 1994, and Kilger et al., Int. Immunol. 9: 219-226, 1997). Thus, it was found that the CS-1-like sequence is important for the interaction of VLA-4/LPAM-1 and VCAM-1/MAdCAM-1.

It was also reported that the cyclic peptide having the CS-1-like structure is antagonistic both to the interaction of VLA-4 or LPAM-1 with VCAM-1, MAdCAM-1 or CS-1 peptide (Vanderslice et al., J. Immunol. 158: 1710-1718, 1997). The above-described facts indicate that all the interactions of α4 integrin and VCAM-1, MAdCAM-1 or fibronectin can be blocked by using a suitable α4 integrin antagonist (the term "α4 integrin antagonist" in the specification indicates a substance antagonistic to α4β1 and/or α4β7 integrin).

It is also known that the expression of VCAM-1 in vascular-endothelium cells is caused by inflammatory factors such as LPS, TNF-α or IL-1 and that when the inflammation occurs, the infiltration of the leukocytes from the blood vessel into the tissue is carried out by the VLA-4/VCAM-1 adhesion mechanism (Elices, Cell 60: 577-584, 1990, Osborn et al., Cell 59: 1203-1211, 1989 and Issekutz et al., J. Eex. Med. 183: 2175-2184, 1996). Because VLA-4 is expressed on the surfaces of activated lymphocytes, monocytes, eosinophils, mast cells and neutrophils, the adhesion mechanism of VLA-4/VCAM-1 plays an important role for the infiltration of those cells into the inflamed tissue. It was reported that VLA-4 is expressed on various sarcoma cells such as melanoma cells, and it was also elucidated that the adhesion mechanism of VLA-4/VCAM-1 participates in the metastasis of these tumors. By investigating the expression of VCAM-1 in various pathological tissues, it was made apparent that the adhesion mechanism of this VLA-4/VCAM-1 participates in various pathological stages. Namely, it was reported that in addition to the activated vascular-endothelium cells, the expression of VCAM-1 is increased in the inflamed tissues in the patients with autoimmune diseases such as rheumatoid synovial membrane (van Dinther-Janssen, J. Immunol. 147: 4207-4210, 1991 and Morales-Ducret et al., J. Immunol. 149: 1424-1431, 1992), lungs and respiratory tract epithelium in asthma (ten Hacken et al., Clin. Exp. Allergy 12: 1518-1525, 1998) and allergic diseases (Randolph et al., J. Clin. Invest. 104: 1021-1029, 1999), systemic lupus erythematosus (Takeuchi et al., J. Clin. Invest. 92: 3008-3016, 1993), Sjögren's syndrome (Edwards et al., Ann. Rheum. Dis. 52: 806-811, 1993), multiple sclerosis (Steffen et al., Am. J. Pathol. 145: 189-201, 1994) and psoriasis (Groves et al., J. Am. Acad. Dermatol. 29: 67-72, 1993); atherosclerotic plagues (O'Brien et al., J. Clin. Invest. 92: 945-951, 1993), intestinal tissues of the patients with inflammatory bowel diseases such as Crohn's disease and ulcerative colitis (Koizumi et al., Gastroenterol. 103: 840-847, 1992 and Nakamura et al., Lab. Invest. 69: 77-85, 1993), inflamed tissue of Langerhans island of patients with diabetes (Martin et al., J. Autoimmun. 9: 637-643, 1996) and implants during the rejection of transplantation of heart or kidney (Herskowitz et al. Am. J. Pathol. 145: 1082-1094, 1994 and Hill et al., Kidney Int. 47: 1383-1391, 1995). The adhesion mechanism of VLA-4/VCAM-1 participates in these various diseases.

There are many reports showing that in vivo administration of VLA-4 or VCAM-1 antibody was effective in improving the diseases of animal models with those inflammatory diseases. Concretely, Yednock et al. and Baron et al. reported that the in vivo administration of an antibody against α4 integrins was effective in controlling the incidence rate or in controlling encephalomyelitis in the experimental autoimmune encephalomyelitis models, i. e. multiple sclerosis models (Yednock et al., Nature 356: 63-66, 1992 and Baron et al., J. Exp. Med. 177: 57-68, 1993). Zeidler et al. reported that in vivo administration of an antibody against α4-integrin was effective in controlling the incidence rate of mouse collagen arthritis (rheumatoid models) (Zeidler et al., Autoimmunity 21: 245-252, 1995). The therapeutic effect of an antibody against α4-integrin in asthma models was reported by Abraham et al. and Sagara et al. (Abraham et al., J. Clin. Invest. 93: 776-787, 1994 and Sagara et al., Int. Arch. Allergy Immunol. 112: 287-294, 1997). The effect of an antibody against α4-integrin in inflammatory bowel disease models was reported by Podolsky et al. (Podolsky et al., J. Clin. Invest. 92: 372-380, 1993). The effect of an antibody against α4-integrin and that against VCAM antibody in insulin-dependent diabetes models were reported by Baron et al. (Baron et al., J. Clin. Invest. 93: 1700-1708, 1994). It was made apparent with baboon models that the restenosis of a blood vessel after an angioplasty carried out because of arteriosclerosis can be inhibited by the administration of α4 integrin antibody (Lumsden et al., J. Vasc. Surg. 26: 87-93, 1997). It was also reported that α4 integrin or VCAM antibody is effective in inhibiting the rejection of an implant or inhibiting metastasis of a cancer (Isobe et al., J. Immunol. 153: 5810-5818, 1994 and Okahara et al., Cancer Res. 54: 3233-3236, 1994).

As described above, unlike VCAM-1, MAdCAM-1 which is a ligand of LPAM-1 is constitutively expressed on high endothelial venules (HEV) in the intestinal mucosa, mesenteric lymphatic nodes, Peyer's patch and spleen and it participates in the homing of mucosal lymphocytes. It is also known that LPAM-1/MAdCAM-1 adhesion mechanism not only has physiological roles in the homing of the lymphocytes but also participates in some pathological processes.

Briskin et al reported an increase in the expression of MAdCAM-1 in inflamed regions in intestinal tracts of patients with inflammatory bowel diseases such as Crohn's disease and ulcerative colitis (Briskin et al., Am. J. Pathol. 151: 97-110, 1997). Hanninen et al. reported that induction of the expression is observed in an inflamed tissue of Langerhans island of NOD mouse which is a model of an insulin-dependent diabetes (Hanninen et al., J. Immunol. 160: 6018-6025, 1998). The fact that LPAM-1/MAdCAM-1 adhesion mechanism participates in the progress of diseases is apparent from the fact that conditions of mouse models with inflammatory bowel disease (Picarella et al., J. Immunol. 158: 2099-2106, 1997) and the above-described NOD mouse models are improved by the in vivo administration of antibody to MAdCAM or antibody to β7 integrin (Hanninen et al., J. Immunol. 160: 6018-6025, 1998 and Yang et al., Diabetes 46: 1542-1547, 1997).

The above-described facts indicate the possibility in that employing the blocking of VLA-4/VCAM-1, LPAM-1/VCAM-1 or LPAM-1/MAdCAM-1 adhesion mechanism by a suitable antagonist is effective in treating the chronic inflammatory diseases described above. The use of the antibody against VLA-4 as the VLA-4 antagonist is described in WO 93/13798, WO 93/15764, WO 94/16094 and WO 95/19790. Peptide compounds as VLA-4 antagonists are described in WO 94/15958, WO 95/15973, WO 96/00581 and WO 96/06108. Amino acid derivatives usable as VLA-4 antagonists are described in WO 99/10312, WO 99/10313, WO 99/36393, WO 99/37618 and WO 99/43642. However, none of them is practically used for the therapeutic treatment at present because of the lack of oral bioavailability and immunogenic properties during the use of them for a long period of time. Amino acid derivatives usable as VLA-4 antagonists are also described in WO 01/36376, WO 01/47868, WO 01/70670 and WO 01/42215.

α4 integrin antagonists wherein A of the general formula (1) represents a nonaromatic heterocyclic ring having a monocyclic structure are disclosed in WO 01/42215. However, there is no disclosure therein on the compounds which the present invention refers to, wherein A of the general formula (1) represents either one of the general formula (2) and (2-1) to (2-7).

α4 integrin antagonists wherein A of the general formula (1) represents (2-5) are disclosed in WO 02/28830. However, there is no disclosure therein on the compounds which the present invention refers to, wherein C of the general formula (1) represents the general formula (3).

DISCLOSURE OF THE INVENTION

An object of the present invention is to provide new compounds having α4 integrin antagonistic effect.

Another object of the present invention is to provide the compounds having α4 integrin antagonistic effect, which can be administered orally.

Still another object of the present invention is to provide α4 integrin antagonists.

A further object of the present invention is to provide a pharmaceutical composition containing such new compounds.

An additional object of the present invention is to provide therapeutic agents or preventive agents for diseases in which α4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

For the purpose of solving the above-described problems, the inventors have synthesized various phenylalanine derivatives and examined α4 integrin antagonistic activities thereof, and the inventors have found that specified, new phenylalanine derivatives have an excellent α4 integrin antagonistic activity. The present invention has been completed on the basis of this finding.

Namely, the present invention provides phenylalanine derivatives of the following general formula (1) and pharmaceutically acceptable salts thereof:

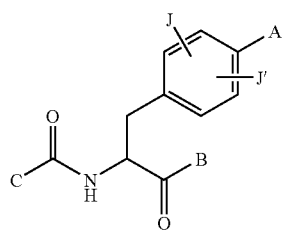
(1)

wherein A represents one of the following general formulae (2), (2-1), (2-2), (2-3), (2-4) and (2-5):

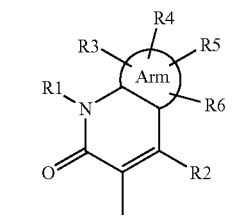
(2)

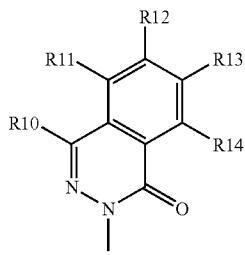
(2-1)

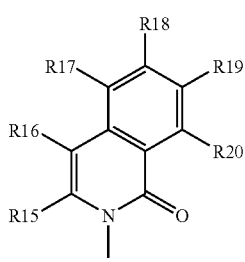
(2-2)

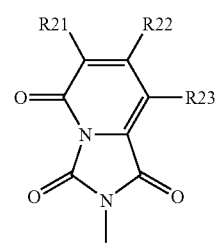
(2-3)

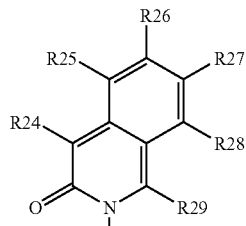
(2-4)

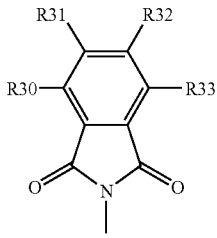
(2-5)

wherein Arm represents a cyclic alkyl group or an aromatic ring containing 0, 1, 2, 3 or 4 hetero atoms selected from the group consisting of oxygen, sulfur and nitrogen atoms, R1 represents a hydrogen atom, an alkyl group which may have a substituent(s), a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower hydroxyalkyl group, a lower halogenoalkyl group, a cycloalkyl group which may contain a hetero atom(s) in the ring thereof, an alkenyl group which may have a substituent(s), a lower hydroxyalkenyl group, a lower halogenoalkenyl group, an alkynyl group which may have a substituent(s), an aryl group, a heteroaryl group, a lower alkyloxycarbonyl group, a substituted or unsubstituted carbamoyl group, a lower alkanoyl group, an aroyl group, a lower alkylsulfonyl group or a substituted or unsubstituted sulfamoyl group, R2 to R6 and R10 to R33 may be the same or different from one another and each represents a hydrogen atom, an alkyl group which may have a substituent(s), a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower hydroxyalkyl group, a lower halogenoalkyl group, a cycloalkyl group which may contain a hetero atom(s) in the ring thereof, an alkenyl group which may have a substituent(s), a lower hydroxyalkenyl group, a lower halogenoalkenyl group, an alkynyl group which may have a substituent(s), an aryl group, a heteroaryl group, a lower alkyloxycarbonyl group, a substituted or unsubstituted carbamoyl group, a lower alkanoyl group, an aroyl group, a lower alkylsulfonyl group, a substituted or unsubstituted sulfamoyl group, a halogen atom, a hydroxyl group, a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a lower hydroxyalkoxyl group, a lower halogeno alkoxyl group, a lower halogenoalkylthio group, a cycloalkyloxy group which may contain a hetero atom(s) in the ring thereof, an aryloxy group, a heteroaryloxy group, a nitro group, a cyano group, a substituted or unsubstituted amino group, carboxyl group or a trialkylammonium group, B represents a hydroxyl group, an alkoxyl group, a substituted lower alkoxyl group or a hydroxylamino group, in cases where A represents the general formula (2), (2-1), (2-2), (2-3) or (2-4), C represents an aryl group, a heteroaryl group, a cycloalkyl group which may contain a hetero atom(s) in the ring thereof, a lower alkyl group substituted with a cycloalkyl group(s) which may contain a hetero atom(s) in the ring thereof, a lower alkyl group substituted with an aryl group(s), a lower alkyl group substituted with a heteroaryl group(s), an alkyl group which may have a substituent(s), a lower hydroxyalkyl group, a lower halogenoalkyl group, an alkenyl group which may have a substituent(s), a lower hydroxyalkenyl group, a lower halogenoalkenyl group, an alkynyl group which may have a substituent(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxylalkoxyl group, a lower halogeno alkoxyl group, a substituted or unsubstituted amino group or a lower alkylthio group, or C also represents an organic group of the following general formula (3):

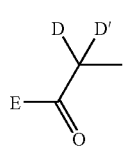

(3)

wherein D and D' may be the same or different from one another and each represents a hydrogen atom, an alkyl group which may have a substituent(s), an alkenyl group which may have a substituent(s) or an alkynyl group which may have a substituent(s), and D and D' may be bonded together to form a ring which may contain one or two oxygen, nitrogen or sulfur atoms, E represents an amino group or a lower alkylamino group which may have a substituent(s), including an amino group(s) having two substituents wherein the substituents are bonded together to form a ring, in cases where A represents the general formula (2-5), C represents an organic group of the general formula (3) wherein D, D' and E represent the same groups as those mentioned above, J and J' may be the same or different from one another and each represents a hydrogen atom, a halogen atom, a lower alkyl group, a lower alkyloxy group, a nitro group, an amino group and a hydroxyl group.

The present invention also provides phenylalanine derivatives of the following general formula (22) and pharmaceutically acceptable salts thereof:

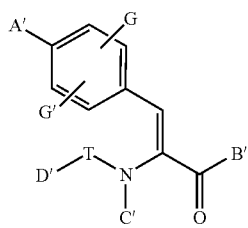

(22)

wherein A' represents one of the following general formulae (23-1), (23-2), (23-3) and (23-4):

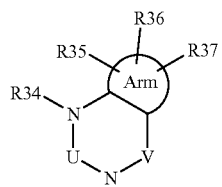

(23-1)

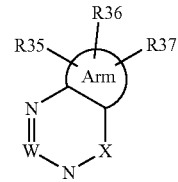

(23-2)

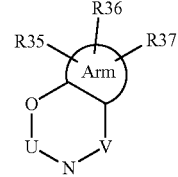

(23-3)

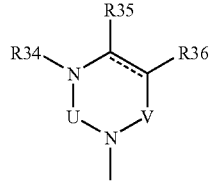

(23-4)

wherein Arm represents a cyclic alkyl group or an aromatic ring containing 0, 1, 2, 3 or 4 hetero atoms selected from the group consisting of oxygen, sulfur and nitrogen atoms, the composite line of solid line and dotted line in the formula (23-4) represents a single bond or a double bond, U, V and X represent $C(=O)$, $S(=O)_2$, $C(-R38)(-R39)$, $C(=C(R38)(R39))$, $C(=S)$, $S(=O)$, $P(=O)(-OH)$ or $P(-H)(=O)$, W represents C(-R40) or a nitrogen atom, R34 to R40 may be the same or different from one another and each represents a hydrogen atom, a halogen atom, a hydroxyl group, a lower alkyl group, a substituted lower alkyl group, a lower alkenyl group, a substituted lower alkenyl group, a lower alkynyl group, a substituted lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxylalkoxyl group, a lower halogenoalkyl group, a lower halogeno alkoxyl group, a lower halogenoalkylthio group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylsulfonyl group, a substituted or unsubstituted sulfamoyl group or an ammonium group, R38 and R39 may be bonded together to form a ring which may contain one or two oxygen, nitrogen or sulfur atoms, B' represents a hydroxyl group, a lower alkoxyl group, a substituted lower alkoxyl group or a hydroxylamino group, C' represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), D' represents a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, C' and D' may be bonded together to form a ring which may contain one or two oxygen, nitrogen or sulfur atoms, T represents an interatomic bond, C(=O), C(=S), S(=O), S(=O)$_2$, N(H)—C(=O), or N(H)—C(=S), G and G' may be the same or different from each other and each represents a hydrogen atom, a halogen atom, a lower alkyl group, a lower alkyloxy group or nitro group.

The present invention also provides the phenylalanine derivatives of the above general formula (1) and pharmaceutically acceptable salts thereof wherein A represents the following general formula (2-6):

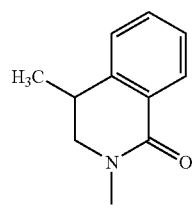

(2-6)

B represents a hydroxyl group or a lower alkoxyl group,
C represents either one of the general formulae (3-1), (3-2) and (3-3) mentioned below, R7 represents a halogen atom or a methyl group, R8 represents a halogen atom, R9 represents a hydrogen atom, a halogen atom, a hydroxyl group, a lower alkyl group, a lower alkoxyl group, a lower alkylthio group, a lower halogenoalkyl group, a lower halogeno alkoxyl group, a lower halogenoalkylthio group, a nitro group, a cyano group, an amino group, a lower alkylamino group, a trialkylammonium group, a methansulfonylamino group or a tetrazolyl group, and J and J' represent a hydrogen atom.

The present invention also provides the phenylalanine derivatives of the above general formula (1) and pharmaceutically acceptable salts thereof wherein A represents the following general formula (2-7):

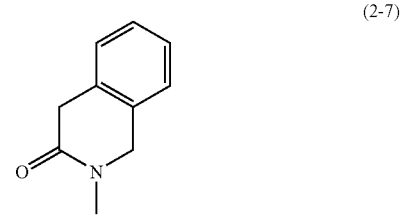

(2-7)

B represents a hydroxyl group or a lower alkoxyl group,
C represents either one of the general formulae (3-1), (3-2) and (3-3) mentioned below, R7 represents a halogen atom or a methyl group, R8 represents a halogen atom, R9 represents a hydrogen atom, a halogen atom, a hydroxyl group, a lower alkyl group, a lower alkoxyl group, a lower alkylthio group, a lower halogenoalkyl group, a lower halogeno alkoxyl group, a lower halogenoalkylthio group, a nitro group, a cyano group, an amino group, a lower alkylamino group, a trialkylammonium group, a methansulfonylamino group or a tetrazolyl group, and J and J' represent a hydrogen atom.

The present invention provides an α4 integrin antagonist containing the above-described phenylalanine derivative or a pharmaceutically acceptable salt thereof as the active ingredient.

The present invention also provides a pharmaceutical composition containing the above-described phenylalanine derivative or a pharmaceutically acceptable salt thereof.

The present invention further provides a therapeutic agent or preventive agent, containing the phenylalanine derivative or a pharmaceutically acceptable salt thereof as the active ingredient, for diseases in which α4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

BEST MODE FOR CARRYING OUT THE INVENTION

"Arm" in the present specification is a cyclic alkyl group or an aromatic ring containing 0, 1, 2, 3 or 4 hetero atoms selected from the group consisting of oxygen, sulfur and nitrogen atoms. It includes, for example, cyclopentane, cyclohexane, piperidine, piperazine, morpholine, pyrrolidine, tetrahydrofuran, benzene, naphthalene, pyridine, pyridazine, pyrimidine, pyrazine, furan, thiophene, pyrrole, isoxazole, isothiazole, pyrazole, imidazole and tetrazole.

Among them, the preferred are cyclohexane, piperidine, benzene, pyridine, thiophene, pyrazole, tetrazole and the like.

The term "lower" in, for example, a lower alkyl group indicates that the group has 1 to 6 carbon atoms and preferably 1 to 4 carbon atoms.

Alkyl groups, alkenyl groups and alkynyl groups in alkyl, alkenyl and alkynyl groups which may have a substituent(s), alkoxyl groups, alkylthio groups, alkanoyl groups, alkylamino groups, alkylsulfonyl groups, lower halogenoalkyl groups, lower hydroxyalkyl groups and the like may be either linear or branched. Examples of these alkyl groups are methyl group, ethyl group, propyl group, isopropyl group, butyl group, secondary butyl group, tertiary butyl group, pentyl group and hexyl group. It is preferable that the alkyl groups have 1 to 6 carbon atoms and more preferable that the groups have 1 to 4 carbon atoms. The alkenyl groups are, for example, vinyl group, propenyl group, butenyl group and pentenyl group. It is preferable that the alkenyl groups have 2 to 6 carbon atoms and more preferable that the groups have 2 to 4 carbon atoms. The alkynyl groups include ethynyl group, propynyl group and butynyl group. It is preferable that the alkenyl groups have 2 to 8 carbon atoms and more preferable that the groups have 2 to 4 carbon atoms.

The lower halogenoalkyl groups include chloromethyl group, trichloromethyl group, trifluoromethyl group, trifluoroethyl group, pentafluoromethyl group, etc.

The lower hydroxyalkyl groups include hydroxymethyl group, hydroxyethyl group, etc.

The cycloalkyl groups or the cycloalkyl groups as a component(s) indicate substituted or unsubstituted cycloalkyl groups and they are preferably nonaromatic hydrocarbon ring groups having 3 to 10 carbon atoms. They include, for example, cyclopropyl group, cyclobutyl group, cyclopentyl group, cyclohexyl group, cycloheptyl group, norbornyl group, adamantyl group and cyclohexenyl group. It is preferable that the cycloalkyl groups have 3 to 8 carbon atoms and more preferable that the groups have 3 to 6 carbon atoms.

The cycloalkyl groups which may contain a hetero atom(s) in the ring thereof may be either substituted or unsubstituted and they are monocyclic or bicyclic nonaromatic ring groups containing 0, 1, 2, 3 or 4 hetero atoms selected from the group consisting of oxygen, sulfur and nitrogen atoms. They include, in addition to the above mentioned cycloalkyl group, pyrrolidinyl group, pyrazolidinyl group, imidazolidinyl group, pyrrolinyl group, pyrazolinyl group, imidazolinyl group, tetrahydrofuranyl group, tetrahydrothiophenyl group, thiazolidinyl group, piperidyl group, piperazinyl group, quinuclidinyl group, tetrahydropyranyl group, morpholinyl group, thiomorpholinyl group, dioxoranyl group, uracil group, homopiperidyl group, homopiperazinyl group, indolinyl group, isoindolinyl group, chromanyl group and isochromanyl group, which are preferably 3-to-8-membered cyclic group, and more preferably 5-to-7-membered cyclic group. It is particularly preferred that they are piperidyl group, piperazinyl group, morpholinyl group, pyrrolidinyl group, tetrahydrofuranyl group or uracil group.

The alkoxyl groups include methoxyl group, ethoxyl group, propyloxy group, isopropyloxy group, etc. The lower halogenoalkoxyl groups include trichloromethoxyl group, trifluoromethoxyl group, etc.

The hetero atoms include nitrogen atoms, oxygen atoms, sulfur atoms, etc.

The halogen atoms are fluorine, chlorine, bromine and iodine.

The substituents in alkyl groups which may have the above substituent(s), alkenyl groups which may have a substituent(s), alkynyl groups which may have a substituent(s), substituted carbamoyl groups, substituted sulfamoyl groups and substituted lower alkoxyl groups are, for example, those mentioned in the above R2 to R6 and R10 to R40. Namely, they are a halogen atom, a hydroxyl group, a substituted or unsubstituted lower alkyl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower hydroxyalkyl group, a lower halogenoalkyl group, a substituted or unsubstituted lower alkenyl group, a lower hydroxyalkenyl group, a lower halogenoalkenyl group, a substituted or unsubstituted lower alkynyl group, a cycloalkyl group which may contain a hetero atom(s) in the ring thereof, an aryl group, a heteroaryl group, a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a lower hydroxylalkoxyl group, a lower halogeno alkoxyl group, a lower halogenoalkylthio group, a cycloalkyloxy group which may contain a hetero atom(s) in the ring thereof, an aryloxy group, a heteroaryloxy group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylsulfonyl group, a substituted or unsubstituted sulfamoyl group or a trialkylammonium group.

In the present specification, the aryl groups in aryl groups, arylsulfonyl groups, arylcarbonyl groups, arylalkoxylcarbonyl groups and the like are substituted or unsubstituted aryl groups. They are monocyclic or bicyclic aromatic hydrocarbon ring groups having 6 to 10 carbon atoms such as phenyl, 1-naphthyl and 2-naphthyl groups which may have a substituent(s). They are preferably phenyl groups which may have a substituent(s).

The heteroaryl groups or the heteroaryl groups as a component(s) are substituted or unsubstituted heteroaryl groups. They are monocyclic, bicyclic or tricyclic aromatic heterocyclic groups such as pyridyl, pyridazinyl, pyrimidinyl, pyrazinyl, furyl, thienyl, pyrrolyl, isoxazolyl, oxazolyl, isothiazolyl, thiazolyl, pyrazolyl, imidazolyl, oxadiazolyl, thiadiazolyl, triazoyl, triazinyltetrazolyl, benzofuranyl, benzothienyl, indolyl, isoindolyl, benzoxazolyl, benzothiazolyl, benzimidazolyl, indazolyl, benzisoxazolyl, benzisothiazolyl, benzofurazanyl, benzothiadiazolyl, purinyl, quinolyl, isoquinolyl, cinnolinyl, phthalazinyl, quinazolinyl, quinoxalinyl, pteridinyl, imidazoxazolyl, imidazothiazolyl, imidazoimidazolyl, dibenzofuranyl, dibenzothienyl, carbazolyl and acridinyl groups which may have a substituent(s). Preferred heteroaryl groups are, for example, pyridyl, furyl and thienyl groups which may have a substituent(s).

When the aryl groups or the heteroaryl groups have a substituent(s), the substituent(s) may be multiple and their examples are those mentioned in the above R2 to R6 and R10 to R40. Namely, they are a halogen atom, a hydroxyl group, a substituted or unsubstituted lower alkyl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower hydroxyalkyl group, a lower halogenoalkyl group, a substituted or unsubstituted lower alkenyl group, a lower hydroxyalkenyl group, a lower halogenoalkenyl group, a substituted or unsubstituted lower alkynyl group, a cycloalkyl group which may contain a hetero atom(s) in the ring thereof, an aryl group, a heteroaryl group, a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a lower hydroxylalkoxyl group, a lower halogeno alkoxyl group, a lower halogenoalkylthio group, a cycloalkyloxy group which may contain a hetero atom(s) in the ring thereof, an aryloxy group, a heteroaryloxy group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylsulfonyl group, a substituted or unsubstituted sulfamoyl group or a trialkylammonium group.

The alkanoyl groups include, for example, formyl groups, acetyl groups, propanoyl group, butanoyl group and pivaloyl group. The lower halogenoalkanoyl groups include, for example, trichloroacetyl group and trifluoroacetyl group.

The aroyl groups are arylcarbonyl groups or heteroarylcarbonyl groups. They include, for example, benzoyl groups which may have a substituent(s) and pyridylcarbonyl group.

The alkylsulfonyl groups include, for example, methanesulfonyl group, ethanesulfonyl group, etc. The arylsulfonyl groups include, for example, benzenesulfonyl group and p-toluenesulfonyl group. The heteroarylsulfonyl groups include, for example, pyridylsulfonyl group. The lower halogenoalkylsulfonyl groups include, for example, trifluoromethanesulfonyl group. The alkyloxycarbonyl groups include, for example, methoxycarbonyl group, ethoxycarbonyl group and tert-butoxycarbonyl group. The aryl alkoxycarbonyl groups include, for example, benzyloxycarbonyl group and 9-fluorenylmethoxycarbonyl group.

The substituted carbamoyl groups include, for example, methylcarbamoyl group and arylcarbamoyl group. The substituted thiocarbamoyl groups include, for example, methylthiocarbamoyl group and arylthiocarbamoyl group.

The substituted amino groups in the present specification indicate mono-substituted or di-substituted amino groups and the substituents thereof include substituted or unsubstituted lower alkyl groups, lower alkyl groups substituted with an aryl group, lower alkyl groups substituted with a heteroaryl group, lower alkanoyl groups, aroyl groups, lower halogenoalkanoyl groups, lower alkylsulfonyl groups, arylsulfonyl groups, heteroarylsulfonyl groups, lower halogenoalkylsulfonyl groups, lower alkyloxycarbonyl groups, aryl-substituted lower alkyloxycarbonyl groups, substituted or unsubstituted carbamoyl groups and substituted or unsubstituted thiocarbamoyl groups. When the substituted amino groups are di-substituted amino groups, those two substituents may be bonded together to form a ring. Such substituents include pyrrolidyl group, piperidyl group and morpholinyl group.

Because the phenylalanine derivatives of the general formula (1) of the present invention include asymmetric carbons, it can be considered that the phenylalanine derivatives of the general formula (1) of the present invention are optical isomers and the compound indicated in the present invention include the said optical isomers. However, L-form is preferable.

Because the phenylalanine derivatives of the general formula (22) of the present invention include double bond, it can be considered that the phenylalanine derivatives of the general formula (22) of the present invention are geometric isomers and the compound indicated in the present invention include the said geometric isomers. However, Z-form is preferable.

Regarding the compound in which a diastereomer exists, the diastereomer and the diastereomer mixture are included in the said phenylalanine derivatives. Because the phenylalanine derivatives of the general formulae (1) and (22) of the present invention include a movable hydrogen atom, it can be considered that the phenylalanine derivatives of the general formulae (1) and (22) of the present invention include a variety of tautomeric forms and the compounds indicated in the present invention include the said tautomeric forms.

Further, the carboxyl groups of the compound of the present invention (for example, the carboxyl groups when B of the general formula (1) or (22) is a hydroxyl group) may be subtituted with appropriate substituents which are converted into a carboxyl group in vivo. Examples of such substituents are those mentioned in Prog. Med. 5: 2157-2161 (1985), in Iyakuhin no Kaihatsu Vol. 7 Bunshisekkei p.163-198 (Hirokawa-shoten, 1990) and in Saishin Soyak Kagaku Gekan p.271-298 (Technomics, Inc., 1999). More concretely, they include, for example, lower alkoxycarbonyl groups such as methoxycarbonyl group, ethoxycarbonyl group and isopropoxycarbonyl group and lower alkoxycarbonyl groups having a substituent(s) such as pivaloyloxymethyloxycarbonyl group, 2-morpholinoethyloxycarbonyl group and cyclohexyloxycarbonyloxymethyloxycarbonyl group.

In the general formula (1), it is preferable that A is the above mentioned general formula (2) wherein Arm is preferably an aromatic ring containing 0, 1, 2, 3 or 4 hetero atoms selected from the group consisting of oxygen, sulfur and nitrogen atoms and more preferably a benzene ring, a pyridine ring or a thiophene ring and particularly preferably a benzene ring. R1 in the formula (2) is preferably a hydrogen atom or a lower alkyl group which may have a substituent(s). It is more preferable that R1 is methyl group or ethyl group.

It is preferable that R2 of the formula (2) is a halogen atom, a cyano group, a lower halogenoalkyl group, a hydrogen atom, a hydroxyl group or a lower alkoxy group. R2 is more preferably methoxy group, ethoxy group or propyloxy group.

R2 of the formula (2) is also preferably a lower alkyl group and more preferably methyl group, ethyl group, propyl group or butyl group and particularly preferably methyl group or propyl group.

R3, R4, R5 and R6 of the formula (2) are preferably a hydrogen atom, a halogen atom, a hydroxyl group, a lower alkyl group, a cycloalkyl group which may contain a hetero atom(s) in the ring thereof, a lower alkoxyl group, a lower halogenoalkyl group, a lower halogeno alkoxyl group, a substituted or unsubstituted amino group, a lower alkylsulfonyl group or a trialkylammonium group.

Further, it is preferable that A is the above mentioned general formula (2) wherein Arm is a benzene ring, R1 is a lower alkyl group, R2 is a lower alkoxyl group or a hydrogen atom, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, an amino group substituted with a lower alkanoyl group, an amino group substituted with a lower alkyloxycarbonyl group, a lower alkylsulfonyl groups or a lower trialkylammonium group. An example of the amino group substituted with a lower alkyl group is a dimethylamino group.

It is also preferable that A is the above mentioned general formula (2) wherein Arm is a benzene ring, R1 is a lower alkyl group, R2 is a lower alkyl group, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, an amino group substituted with a lower alkanoyl group, an amino group substituted with a lower alkyloxycarbonyl group, a lower alkylsulfonyl groups or a lower trialkylammonium group. An example of the amino group substituted with a lower alkyl group is a dimethylamino group.

B is preferably a hydroxyl group or a lower alkoxyl group. B is particularly preferably a hydroxyl group because, when B is a hydroxyl group, it can raise the blood concentration of the compound as the ester compound. Examples of the lower alkoxyl group are methoxy group, ethoxy group and isopropyl group.

When B is a substituted lower alkoxyl group, the substituents thereof are, for example, an aryl group, a heteroaryl group, a cycloalkyl group which may contain a hetero atom(s) in the ring thereof, a lower alkylcarbonyloxy group, an arylcarbonyloxy group, a heteroaryl-carbonyloxy group, a cycloalkylcarbonyloxy group which may contain a hetero atom(s) in the ring thereof, a lower alkyloxycarbonyloxy group, an aryloxycarbonyloxy group, a heteroaryloxycarbonyloxy group and a cycloalkyloxycarbonyloxy group which may contain a hetero atom(s) in the ring thereof. Examples of the substituted lower alkoxyl group are a pivaloyloxymethoxy group, a morpholin-4-yl-ethoxy group and a 1-(cyclohexyloxylcarbonyloxy) ethoxy group.

C is preferably an aryl group, a heteroaryl group, the above mentioned general formula (3) or a cycloalkyl group which may contain a hetero atom(s) in the ring thereof. The aryl group, the heteroaryl group and the cycloalkyl group which may contain a hetero atom(s) in the ring thereof may have a substituent(s) as mentioned above, the substituents thereof are those mentioned in the above R3 to R6 and R10 to R33.

It is more preferable that C represents the above mentioned general formula (3) or the following general formulae (3-1), (3-2), (3-3) or (3-4):

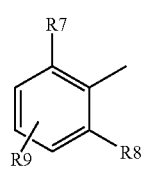
(3-1)

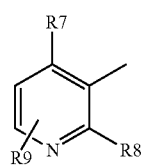
(3-2)

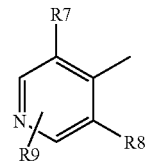
(3-3)

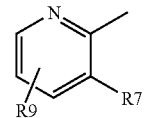
(3-4)

wherein R7 represents a halogen atom or methyl group, R8 represents a halogen atom, methyl group, trifluoromethyl group, methoxy group or a hydrogen atom, R9 represents a hydrogen atom, halogen atom, hydroxyl group, lower alkyl group, cycloalkyl group which may contain a hetero atom(s) in the ring thereof, lower alkoxyl group, lower alkylthio group, lower halogenoalkyl group, lower halogenoalkoxyl group, lower halogenoalkylthio group, nitro group, cyano group, amino group, amino group substituted with a lower alkyl group(s), lower trialkylammonium group, lower alkylsulfonylamino group or tetrazolyl group.

C is further more preferably the above general formula (3-1) and particularly the formula (3-1) wherein R8 represents a halogen atom or methyl group. An Example of such a group is 2,6-dichlorophenyl group.

J and J' are preferably a hydrogen atom.

The compounds of the general formula (1) are preferably the following compounds:

It is preferably the phenylalanine derivatives or a pharmaceutically acceptable salt thereof wherein A is the above mentioned general formula (2) wherein Arm is a benzene ring, R1 is a lower alkyl group, R2 is a lower alkyl group, a lower alkoxyl group or a hydrogen atom, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, an amino group substituted with a lower alkanoyl group, an amino group substituted with a lower alkyloxycarbonyl group, a lower alkylsulfonyl groups or a lower trialkylammonium group.

In this connection, it is further preferably the phenylalanine derivatives or a pharmaceutically acceptable salt thereof wherein B is a hydroxyl group or a lower alkoxyl group.

In this connection, it is further more preferably the phenylalanine derivatives or a pharmaceutically acceptable salt thereof wherein C is the above mentioned general formulae (3), (3-1), (3-2), (3-3) or (3-4).

It is also preferably the phenylalanine derivatives or a pharmaceutically acceptable salt thereof wherein A is the above mentioned general formula (2) wherein Arm is a benzene ring, R1 is a lower alkyl group, R2 is a lower alkoxyl group or a hydrogen atom, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, an amino group substituted with a lower alkanoyl group, an amino group substituted with a lower alkyloxycarbonyl group, a lower alkylsulfonyl groups or a lower trialkylammonium group.

In this connection, it is further preferably the phenylalanine derivatives or a pharmaceutically acceptable salt thereof wherein B is a hydroxyl group or a lower alkoxyl group.

In this connection, it is further more preferably the phenylalanine derivatives or a pharmaceutically acceptable salt thereof wherein C is the above mentioned general formulae (3), (3-1), (3-2), (3-3) or (3-4).

It is also preferably the phenylalanine derivatives or a pharmaceutically acceptable salt thereof wherein A is the above mentioned general formula (2) wherein Arm is a benzene ring, R1 is a lower alkyl group, R2 is a lower alkyl group, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B is a hydroxyl group or a lower alkoxyl group, C is the above mentioned general formulae (3-1) or (3-2), and J and J' are a hydrogen atom.

It is also preferably the phenylalanine derivatives or a pharmaceutically acceptable salt thereof wherein A is the above mentioned general formula (2) wherein Arm is a benzene ring, R1 is a lower alkyl group, R2 is a lower alkoxyl group, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B is a hydroxyl group or a lower alkoxyl group, C is the above mentioned general formulae (3-1) or (3-2), and J and J' are a hydrogen atom.

It is also preferably the phenylalanine derivatives or a pharmaceutically acceptable salt thereof wherein A is the above mentioned general formula (2) wherein Arm is a benzene ring, R1 is a lower alkyl group, R2 is a hydrogen atom, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B is a hydroxyl group or a lower alkoxyl group, C is the above mentioned general formulae (3-1) or (3-2), and J and J' are a hydrogen atom.

It is also preferably the phenylalanine derivatives or a pharmaceutically acceptable salt thereof wherein A is the above mentioned general formula (2) wherein Arm is a benzene ring, R1 is a methyl group or an ethyl group, R2 is a methoxy group or a hydrogen atom, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B is a hydroxyl group, C is the above mentioned general formulae (3-1) or (3-2) wherein R7 represents a halogen atom or methyl group, R8 represents a halogen atom, R9 represents a hydrogen atom, halogen atom, hydroxyl group, lower alkyl group, lower alkoxyl group, lower alkylthio group, lower halogenoalkyl group, lower halogenoalkoxyl group, lower halogenoalkylthio group, nitro group, cyano group, amino group, amino group substituted with a lower alkyl group(s), lower trialkylammonium group, methanesulfonyl amino group or tetrazolyl group, and J and J' are a hydrogen atom.

It is also preferably the phenylalanine derivatives or a pharmaceutically acceptable salt thereof wherein A is the above mentioned general formula (2) wherein Arm is a benzene ring, R1 is a methyl group or an ethyl group, R2 is a methoxy group, an ethoxy group, a propoxy group, a methyl group, an ethyl group, a propyl group or a butyl group, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B is a hydroxyl group, C is the above mentioned general formulae (3-1) or (3-2) wherein R7 represents a halogen atom or methyl group, R8 represents a halogen atom, R9 represents a hydrogen atom, halogen atom, hydroxyl group, lower alkyl group, lower alkoxyl group, lower alkylthio group, lower halogenoalkyl group, lower halogenoalkoxyl group, lower halogenoalkylthio group, nitro group, cyano group, amino group, lower alkylamino group, trialkylammonium group, methanesulfonyl amino group or tetrazolyl group, and J and J' are a hydrogen atom.

It is also preferably the phenylalanine derivatives or a pharmaceutically acceptable salt thereof wherein A is the above mentioned general formula (2) wherein Arm is a benzene ring, R1 is a methyl group or an ethyl group, R2 is a methoxy group, an ethoxy group or a propoxy group, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B is a hydroxyl group, C is the above mentioned general formulae (3-1) or (3-2) wherein R7 represents a halogen atom or methyl group, R8 represents a halogen atom, R9 represents a hydrogen atom, halogen atom, hydroxyl group, lower alkyl group, lower alkoxyl group, lower alkylthio group, lower halogenoalkyl group, lower halogenoalkoxyl group, lower halogenoalkylthio group, nitro group, cyano group, amino group, lower alkylamino group, trialkylammonium group, methanesulfonyl amino group or tetrazolyl group, and J and J' are a hydrogen atom.

It is also preferably the phenylalanine derivatives or a pharmaceutically acceptable salt thereof wherein A is the above mentioned general formula (2) wherein Arm is a benzene ring, R1 is a methyl group or an ethyl group, R2 is a methyl group, an ethyl group, a propyl group or a butyl group, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B is a hydroxyl group, C is the above mentioned general formulae (3-1) or (3-2) wherein R7 represents a halogen atom or methyl group, R8 represents a halogen atom, R9 represents a hydrogen atom, halogen atom, hydroxyl group, lower alkyl group, lower alkoxyl group, lower alkylthio group, lower halogenoalkyl group, lower halogenoalkoxyl group, lower halogenoalkylthio group, nitro group, cyano group, amino group, lower alkylamino group, trialkylammonium group, methanesulfonyl amino group or tetrazolyl group, and J and J' are a hydrogen atom.

It is also preferably the phenylalanine derivatives or a pharmaceutically acceptable salt thereof wherein A is the above mentioned general formulae (2-1), (2-2), (2-3) or (2-4) wherein R2 to R6 and R10 to R33 may be the same or different from one another and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group or a lower trialkylammonium group, B is a hydroxyl group or a lower alkoxyl group, and C is the above mentioned general formulae (3-1), (3-2), (3-3) or (3-4).

It is also preferably the phenylalanine derivatives or a pharmaceutically acceptable salt thereof wherein A is the above mentioned general formula (2-5) wherein R30 to R33 may be the same or different from one another and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group or a lower trialkylammonium group, B is a hydroxyl group or a lower alkoxyl group, and C is the above mentioned general formula (3).

In the general formula (22), it is preferable that A' is the above mentioned general formula (23-1) wherein Arm is preferably an aromatic ring and more preferably a benzene ring, a pyridine ring or a thiophene ring and particularly preferably a benzene ring.

R34 in the formula (23-1) is preferably a hydrogen atom or a lower alkyl group which may have a substituent(s). It is more preferable that R34 is methyl group or ethyl group.

R35 to R37 in the formula (23-1) are preferably a hydrogen atom, a halogen atom, a hydroxyl group, a lower alkyl group, a cycloalkyl group which may contain a hetero atom(s) in the ring thereof, a lower alkoxyl group, a lower halogenoalkyl group, a lower halogeno alkoxyl group, a nitro group, a cyano group, a substituted or unsubstituted amino group, or a trialkylammonium group.

B' is preferably a hydroxyl group or a lower alkoxyl group and particularly preferably a hydroxyl group. Examples of the lower alkoxyl group are methoxy group, ethoxy group and isopropyl group.

When B' is a substituted lower alkoxyl group, the substituents thereof are, for example, an aryl group, a heteroaryl group, a cycloalkyl group which may contain a hetero atom(s) in the ring thereof, a lower alkylcarbonyloxy group, an arylcarbonyloxy group, a heteroarylcarbonyloxy group, a cycloalkylcarbonyloxy group which may contain a hetero atom(s) in the ring thereof, a lower alkyloxycarbonyloxy group, an aryloxycarbonyloxy group, a heteroaryloxycarbonyloxy group and a cycloalkyloxycarbonyloxy group which may contain a hetero atom(s) in the ring thereof. Examples of the substituted lower alkoxyl group are a pivaloyloxymethoxy group, a morpholin-4-yl-ethoxy group and a 1-(cyclohexyloxylcarbonyloxy) ethoxy group.

C' is preferably a hydrogen atom or a lower alkyl group and more preferably a hydrogen atom.

D' is preferably an aryl group, a heteroaryl group or a cycloalkyl group which may contain a hetero atom(s) in the ring thereof and more preferably an aryl group or a heteroaryl group. It is particularly preferable that D' is a benzene ring which may contain a hetero atom(s) in the ring thereof or a pyridine ring which may contain a hetero atom(s) in the ring thereof. The aryl group, the heteroaryl group and the cycloalkyl group which may contain a hetero atom(s) in the ring thereof may have a substituent(s) as mentioned above, the substituents thereof are those mentioned in the above R35 to R37.

T is preferably C(=O) or S(=O)$_2$ and more preferably C(=O).

G and G' may be the same or different from one another and are preferably a hydrogen atom.

In the general formula (1), it is more preferably the phenylalanine derivatives or a pharmaceutically acceptable salt thereof wherein A is the above mentioned general formula (2-6), B is a hydroxyl group or a lower alkoxyl group, C is the above mentioned general formula (3-1) wherein R7 represents a chlorine atom, R8 represents a chlorine atom, R9 represents a hydrogen atom, and J and J' are a hydrogen atom.

In the general formula (1), it is also more preferably the phenylalanine derivatives or a pharmaceutically acceptable salt thereof wherein A is the above mentioned general formula (2-7), B is a hydroxyl group or a lower alkoxyl group, C is the above mentioned general formula (3-1) wherein R7 represents a chlorine atom, R8 represents a chlorine atom, R9 represents a hydrogen atom, and J and J' are a hydrogen atom.

More concretely, the compounds described in Examples are preferable though they are not particularly limited.

The compounds (1) of the present invention can be synthesized, for example, by common methods described below.

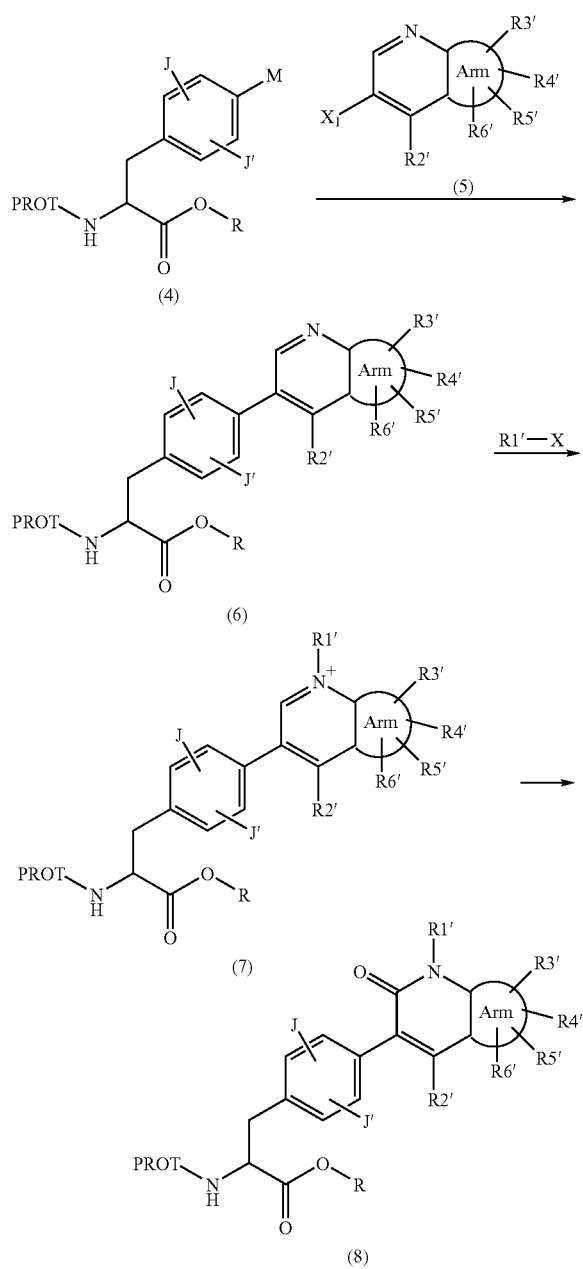

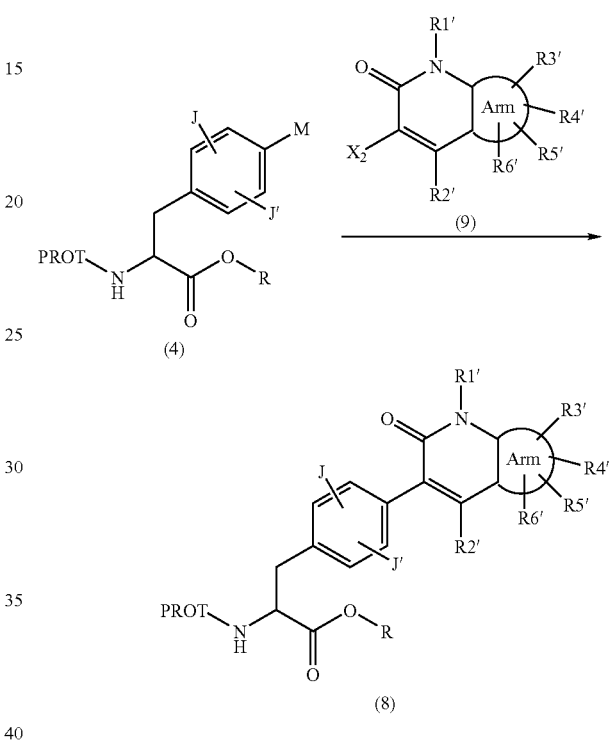

represents a halogen atom such as bromine and iodine or trifluoromethansulfonyloxy group and the like. R1'-X, for example, can be treated with the compound (6) to introduce a cation (7). R1' is a substituent(s) having the structure of R1 or the substituent(s) which can be converted into R1 in a certain point of the subsequent synthesizing process. X represents a removing group of a halogen atom and the like. The cation (7) can be oxidized by treating with potassium t-butoxide in a solvent(s) such as t-butyl alcohol to obtain an amide (8).

In the phenylalanine derivative (4), PROT represents a protective group of an amine, such as t-butoxycarbonyl group, R represents a lower alkyl group, a solid phase supporter and the like and M represents a dialkoxyboron, dihydroxyboron, trialkyltin and the like. (4) can be prepared by converting iodine of the corresponding iodine-body into M by well-known reactions like Process 1 of Example 1. A halide (5) can be treated with (4) in a solvent(s) such as DMF (N,N-dimethylformamide) under the existence of a palladium catalyst(s) such as $PdCl_2$ (dppf) [dppf: 1,1'-bis(diphenylphosphino)ferrocene] and a base(s) such as an aqueous solution of sodium carbonate to obtain (6). In the halide (5), R2', R3', R4', R5' and R6' are the substituents having the structure of R2, R3, R4, R5 and R6 respectively or the substituents which can be converted into R2, R3, R4, R5 and R6 respectively in the subsequent synthesizing process. $X_1$ The amide (8) can also be obtained by treating an halide (9) with the phenylalanine derivative (4) in a solvent(s) such as DMF under the existence of a palladium catalyst(s) such as $PdCl_2$(dppf) and a base(s) such as an aqueous solution of sodium carbonate. In the halide (9), $X_2$ represents a halogen atom such as bromine and iodine or trifluoromethansulfonyloxy group and the like.

The halide (5) and halide (9) can be synthesized, for example, by the well-known reactions such as halogenation of well-known materials like Referential Example 1.

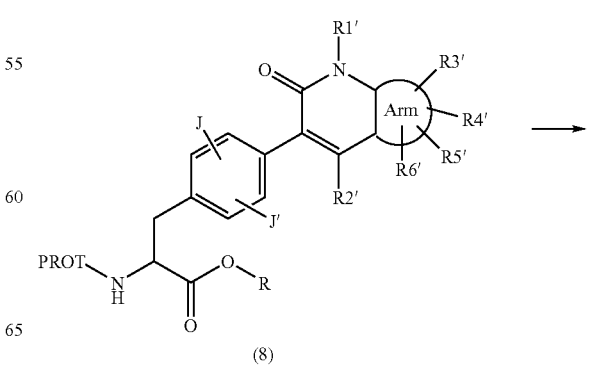

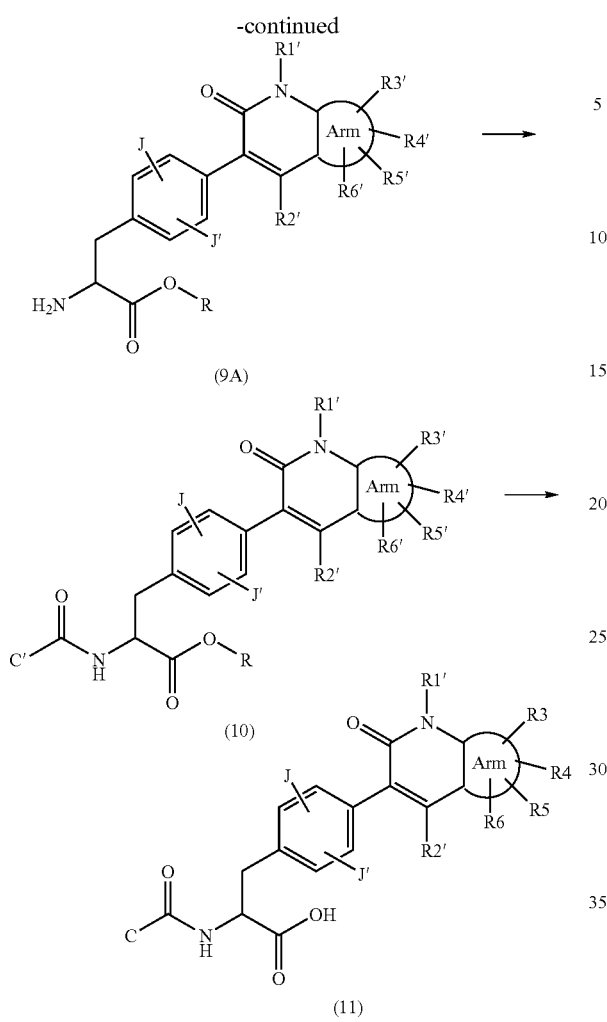

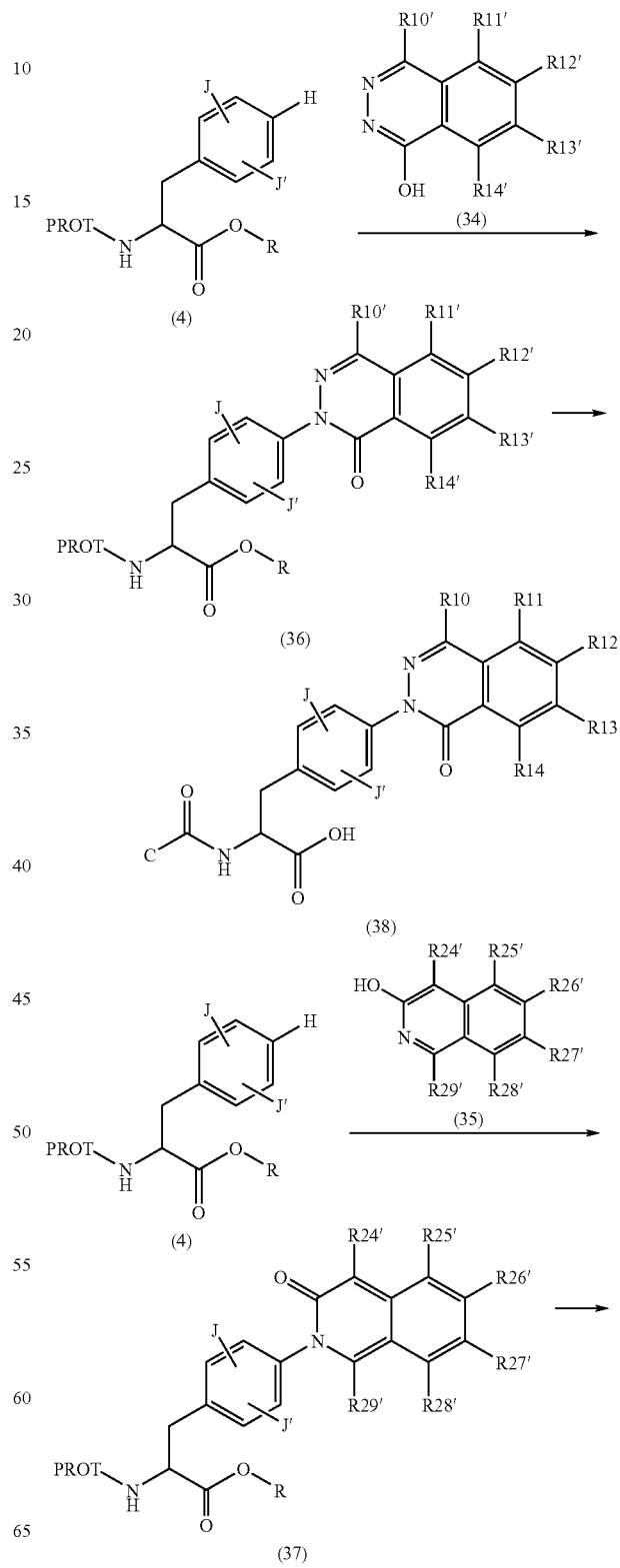

B represents a hydroxyl group. When R represents a solid phase supporter, the ester (10) can be separated from the supporter by hydrated TFA to obtain a carboxylic acid (11) wherein, in the general formula (1), A represents the general formula (2) and B represents a hydroxyl group.

Next, an amine (9A) can be obtained by removing a protective group(s) from the amide (8). For example, when PROT represents a t-butoxycarbonyl group, a protective group(s) can be removed by treating with a dioxane solution of hydrogen chloride. The amine (9A) can be condensed with a proper carboxylic acid by using, if necessary, a suitable additive such as HOAt (1-hydroxy-7-azabenzotriazole) and HOBt (1-hydroxybenzotriazole) and a condensing agent such as DIC (diisopropylcarbodiimide) in an organic solvent such as DMF and dichloromethane to introduce an amide (10). The amine (9A) can also be reacted with carboxylic halide, carboxylic anhydride and the like under the existence of a suitable base such as triethylamine in a solvent such as dichloromethane to introduce an amide (10). C' is a group having the structure of C in the formula (1) or a group which can be converted into C in the subsequent synthesizing process. The compound of the formula (1) wherein A represents the formula (2) and B represents a lower alkoxyl group can be obtained by converting R1' to R5' and C' of(10), if necessary.

Thus synthesized ester (10) can be hydrolyzed under the suitable condition such as the hydrolysis by treating with an aqueous solution of lithium hydroxide in a solvent(s) such as THF (tetrahydrofuran) or the hydrolysis by treating with 1,4-dioxane solution of hydrogen chloride under the wet condition to obtain a carboxylic acid (11) wherein, in the general formula (1), A represents the general formula (2) and

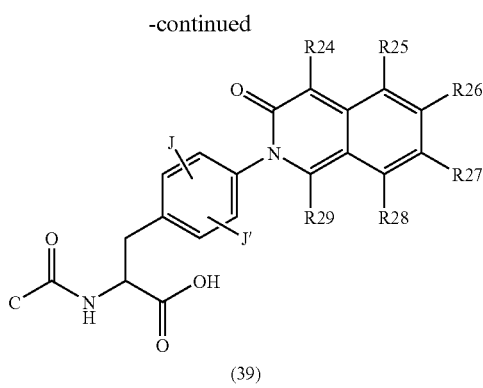

(39)

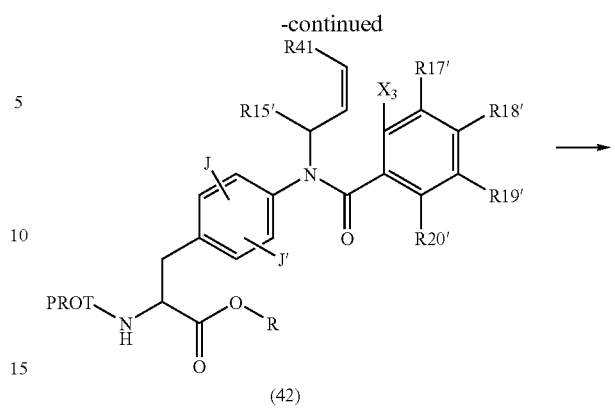

(42)

The compounds of the general formula (1) wherein A are general formulae (2-1) and (2-4) respectively can be synthesized by the methods described below. The phenylalanine derivative (4) wherein M represents dihydroxyboron or dialkylboron can be treated with phenols (34) and (35) under the existence of copper acetate(II) to obtain amides (36) and (37) respectively. R10' to R14' and R24' to R29' are the substituents having the structure of R10 to R14 and R24 to R29 respectively or the substituents which can be converted into R10 to R14 and R24 to R29 respectively in the subsequent synthesizing process. The obtained (36) and (37) can be treated with the same reactions as those of the conversion from (8) to (11) to obtain carboxylic acids (38) and (39) wherein, in the general formula (1), A represent the general formulae (2-1) and (2-4) respectively and B represents a hydroxyl group.

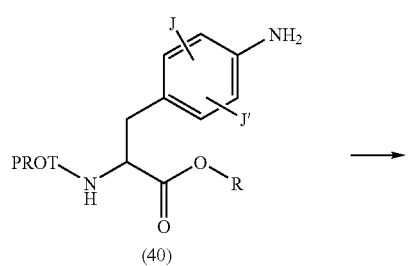

(40)

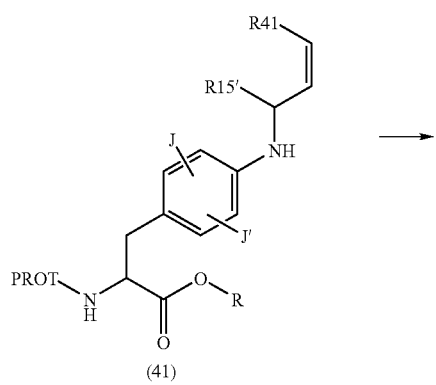

(41)

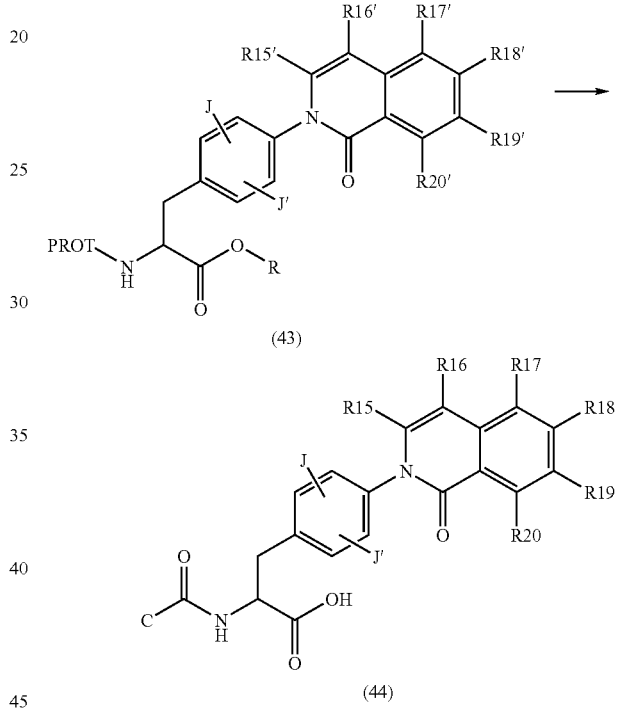

(43)

(44)

The compound of the general formula (1) wherein A is a general formula (2-2) can be synthesized by the methods described below. In the above drawing, R41 is a functional group wherein R41-CH$_2$— becomes R16'-. R15' to R20' are the substituents having the structure of R15 to R20 respectively or the substituents which can be converted into R15 to R20 respectively in the certain synthesizing process. In the phenylalanine (40), PROT and R are the same functional groups as those represented in (4). (40) can be treated with various well-known N-monoalkylation methods to obtain an allylamine (41). The allylamine (41) can be reacted with halide benzoate having a halogen atom such as iodine and bromine on the second position in a solvent(s) such as dichloromethane under the existence of a suitable base to obtain an amide (42). X$_3$ represents a halogen atom. The amide (42) can be reacted with a palladium catalyst(s) such as palladium acetate in a solvent(s) such as DMF under the existence of a suitable base to obtain a cyclic compound (43). The obtained (43) can be treated with the same reactions as those of the conversion from (8) to (11) to obtain a carboxylic acid (44) wherein, in the general formula (1), A represents the general formula (2-2) and B represents a hydroxyl group.

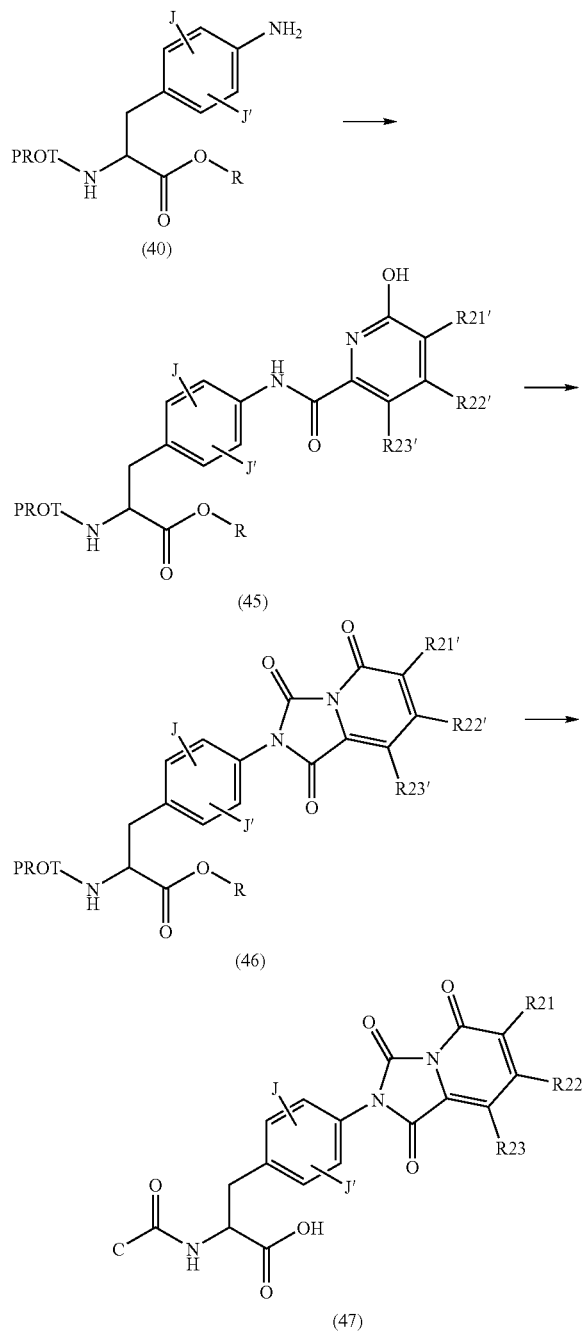

zotriazole) and a condensing agent such as DIC (diisopropylcarbodiimide) in an organic solvent such as DMF and dichloromethane to introduce an amide (45). The obtained amide (45) can be reacted with 1,1-carbonylbisimidazol, phosgene and the like in a solvent(s) such as decahydronaphthalene to obtain a cyclic compound (46). The obtained (46) can be treated with the same reactions as those of the conversion from (8) to (11) to obtain a carboxylic acid (47) wherein, in the general formula (1), A represents the general formula (2-3) and B represents a hydroxyl group.

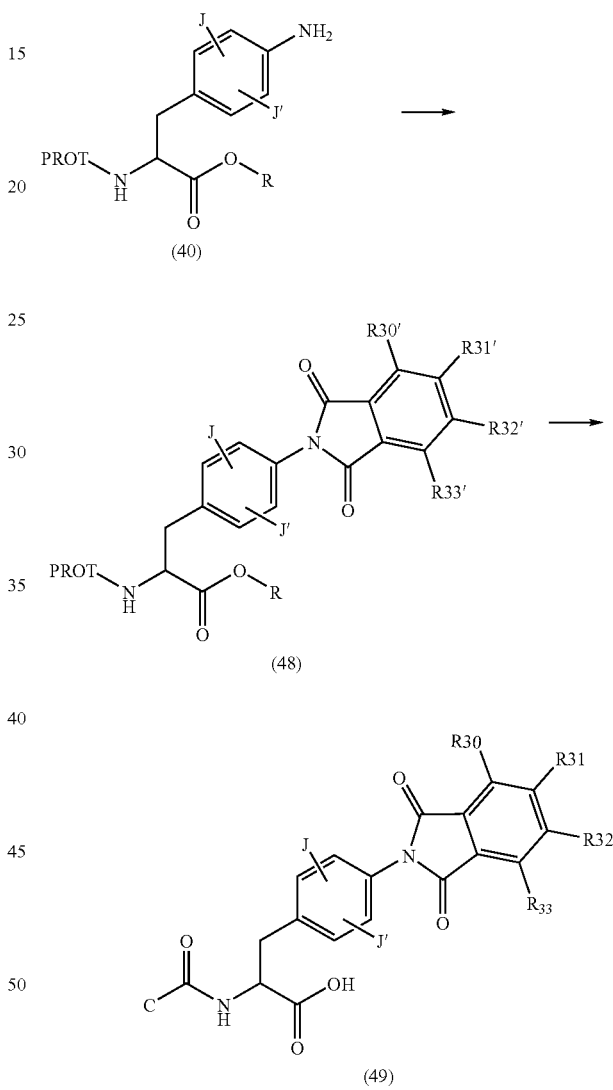

The compound of the general formula (1) wherein A is a general formula (2-3) can be synthesized by the methods described below. In the above drawing, R21' to R23' are the substituents having the structure of R21 to R 23 respectively or the substituents which can be converted into R21 to R 23 respectively in the certain synthesizing process. The phenylalanine derivative (40) can be condensed with various picolinic acids having a hydroxyl group on the sixth position by using, if necessary, a suitable additive such as HOAt (1-hydroxy-7-azabenzotriazole) and HOBt (1-hydroxyben- The compound of the general formula (1) wherein A is a general formula (2-5) can be synthesized by the methods described below. In the above drawing, R30' to R33' are the substituents having the structure of R30 to R33 respectively or the substituents which can be converted into R30 to R33 respectively in the certain synthesizing process. The phenylalanine derivative (40) can be reacted with a phthalic anhydride in a solvent(s) such as benzene under the existence of a suitable base, if necessary, to obtain an imide (48). The imide (48) can be treated with the same reactions as those of the conversion from (8) to (11) to obtain a carboxylic acid (49) wherein, in the general formula (1), A represents the general formula (2-5) and B represents a hydroxyl group.

The compound of the general formula (1) wherein B represents a lower alkoxyl group having a substituent(s) can be obtained by condensing a lower alcohol(s) having a substituent(s) with the carboxylic acids (11), (38), (39), (44), (47), (49) and the like under a suitable condensing agent or an acid catalyst.

The compound of the general formula (1) wherein B represents a hydroxylamino group can be obtained by condensing a hydroxylamine with the carboxylic acids (11), (38), (39), (44), (47), (49) and the like by using a suitable condensing agent.

Thus synthesized compounds of the formula (1) and the salt thereof can be isolated and purified by using well-known isolating and purification methods such as condensation, extraction, crystallization, various chromatography and recrystallization.

When the compounds of general formula (1) or (22) of the present invention can form salts thereof, it is sufficient for the salts to be pharmaceutically acceptable ones. When the compound has an acidic group such as carboxyl group, the salts can be ammonium salts, or salts thereof with alkali metals, e. g. sodium and potassium, salts thereof with alkaline earth metals, e. g. calcium and magnesium, salts thereof with aluminum and zinc, salts thereof with organic amines, e. g. triethylamine, ethanolamine, morpholine, piperidine and dicyclohexylamine, and salts thereof with basic amino acids, e. g. arginine and lysine. When the compound has a basic group, the salts can be those with inorganic acids, e. g. hydrochloric acid, sulfuric acid and phosphoric acid; those with organic carboxylic acids, e. g. acetic acid, citric acid, benzoic acid, maleic acid, fumaric acid, tartaric acid and succinic acid; and those with organosulfonic acids, e. g. methanesulfonic acid and p-toluenesulfonic acid. The salts can be formed by mixing a compound of the general formula (1) or (22) with a necessitated acid or base in a proper ratio in a solvent or dispersant or by the cation exchange or anion exchange reaction with another salt.

The compounds of the general formula (1) or (22) of the present invention include also solvates thereof such as hydrates and alcohol adducts thereof.

The compounds of general formula (1) or (22) and salts thereof are administered as they are or in the form of various pharmaceutical compositions to patients. The dosage forms of the pharmaceutical compositions are, for example, tablets, powders, pills, granules, capsules, suppositories, solutions, sugar-coated tablets, depots and syrups. They can be prepared with ordinary preparation assistants by an ordinary method.

For example, the tablets are prepared by mixing the phenylalanine derivative, the active ingredient of the present invention, with any of known adjuncts such as inert diluents, e. g. lactose, calcium carbonate and calcium phosphate; binders, e. g. acacia, corn starch and gelatin; extending agents, e. g. alginic acid, corn starch and pre-gelatinized starch; sweetening agents, e. g. sucrose, lactose and saccharin; flavour, e. g. peppermint, Akamono (Gaultheria aderothrix) Oil and cherry; lubricants, e. g. magnesium stearate, talc and carboxymethyl cellulose; excipients for soft gelatin capsules and suppositories, e. g. fats, waxes, semi-solid or liquid polyols, natural oils and hardened oils; and excipients for solutions, e. g. water, alcohols, glycerols, polyols, sucrose, invert sugars, glucose and vegetable oils.

The antagonist containing a compound(s) of the general formula (1) or (22) or a salt(s) thereof as active ingredient is usable as a therapeutic agent or preventing agent for diseases in which α4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis, transplantation rejection, etc.

The dose of the compound of the general formula (1) or (22) or salts thereof used for the above-described purpose varies depending on the intended therapeutic effect, administration method, period of the treatment, and age and body weight of the patient. The dose is usually 1 µg to 5 g a day for adults in the oral administration, and 0.01 µg to 1 g a day for adults in the parenteral administration.

The following Examples will further illustrate the present invention, which are only preferred embodiments of the invention and which by no means limit the invention.

EXAMPLE 1

Synthesis of the Compound of the Following General Formula (12) Which has Substituents of Example 1 of Table 1

Process 1
Methyl (2S)-2-[(t-butoxycarbonyl)amino]-3-[4-(4,4,5,5-tetramethyl-1,3,2-dioxaborolan-2-yl) phenyl] propionate

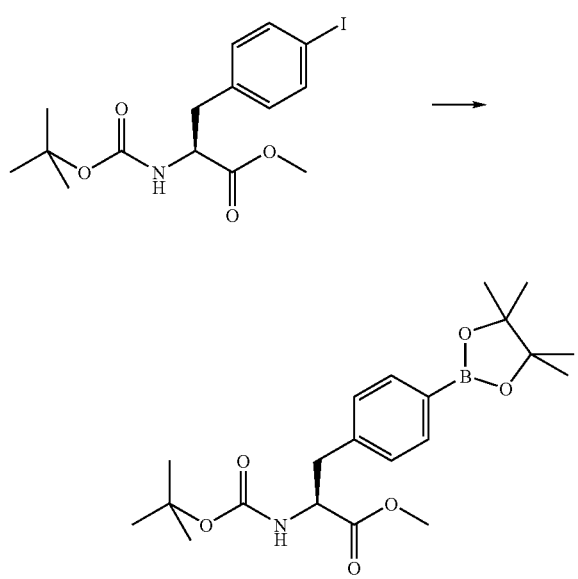

PdCl$_2$(dppf) (127 mg), triethylamine (2.14 ml), 4,4,5,5-tetramethyl-1,3,2-dioxaborolan (1.13 ml) and 1,4-dioxane (21 ml) were added to methyl (2S)-2-[(t-butoxycarbonyl)amino]-3-(4-iodophenyl)propionate (1.8 g) and stirred at 100° C. for 14 hours. The reaction solution was diluted with ethyl acetate, washed with water and dried over magnesium sulfate to remove the solvent. The residue was purified with a silica gel chromatography (hexane-ethyl acetate) to obtain the title compound (1.05 g).

MS (ESI MH+): 406

CHNO: C21H32BNO6

Process 2
Methyl(2S)-2-[(t-butoxycarbonyl)amino]-3-[4-(3-quinolinyl) phenyl] propionate

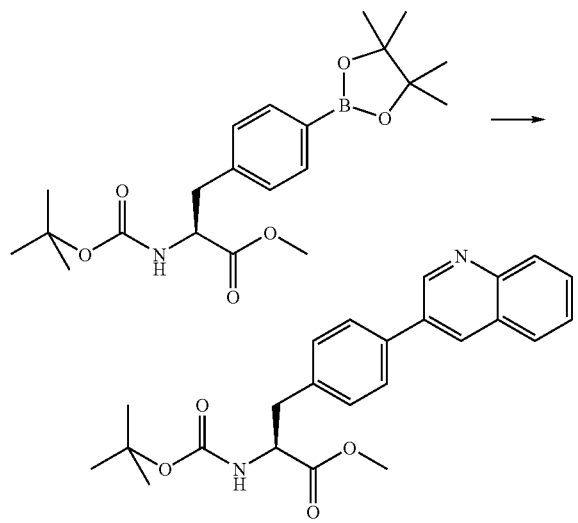

PdCl$_2$(dppf) (151 mg), an aqueous solution of 2M sodium carbonate (3.07 ml), 3-bromoquinoline (185 μl) and DMF (10 ml) were added to the compound obtained in Process 1 (500 mg) and stirred at 90° C. for two hours. The reaction solution was diluted with ethyl acetate, washed with water and dried over magnesium sulfate to remove the solvent. The residue was purified with a silica gel chromatography (hexane-ethyl acetate) to obtain the title compound (190 mg).

MS (ESI MH+): 407

CHNO: C24H26N2O4

Process 3
(2S)-2-[(t-butoxycarbonyl) amino]-3-[4-(1-methyl-2-oxo-1,2-dihydro-3-quinolinyl) phenyl] propionic acid

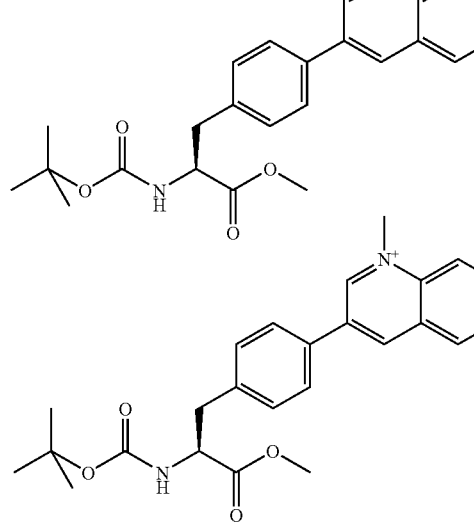

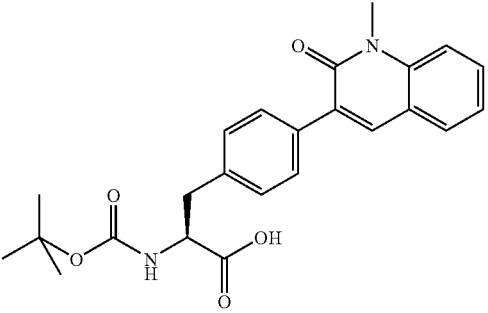

Methyl iodide (2 ml) and tetrahydrofuran (5 ml) were added to the compound obtained in Process 2 (200 mg) and stirred at 95° C. for 13 hours. The solvent was removed and t-butoxy potassium (48 mg) and t-butyl alcohol (2 ml) were added to the obtained residue and stirred for 24 hours. The reaction solution was diluted with ethyl acetate, washed with an aqueous solution of 50% citric acid and dried over magnesium sulfate to remove the solvent. The residue was purified with a reverse phase high performance liquid chromatography (reverse phase HPLC) (water-acetonitrile, each containing 0.1% trifluoroacetate (TFA)) to obtain the title compound (31 mg).

MS (ESI MH+): 423

CHNO: C24H26N2O5

Process 4
Methyl (2S)-2-[(2,6-dichlorobenzoyl)amino]-3-[4-(1-methyl-2-oxo-1,2-dihydro-3-quinolinyl) phenyl] propionate

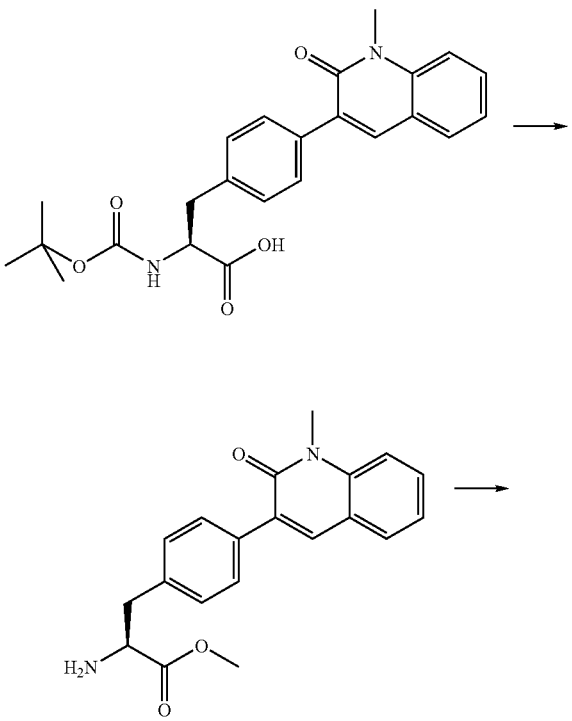

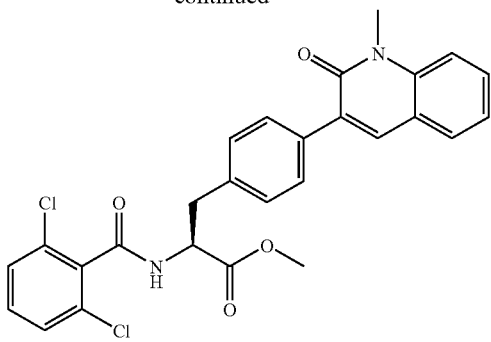

Thionylchloride (50 μl) and methanol (1 ml) were added to the compound obtained in Process 3 (14 mg) and stirred at room temperature for 15 hours. The solvent was removed to obtain a crude material of methyl (2S)-2-amino-3-[4-(1-methyl-2-oxo-1,2-dihydro-3-quinolinyl) phenyl]propionate hydrochloride. 2,6-dichlorobenzoylchloride (10 μl), triethylamine (10 μl) and dichloromethane (300 μl) were added therein and stirred for four hours. The solvent was removed and the residue was purified with a silica gel chromatography (hexane-ethyl acetate) to obtain the title compound (10 mg).

MS (ESI MH+): 509

CHNO: C27H22Cl2N2O4

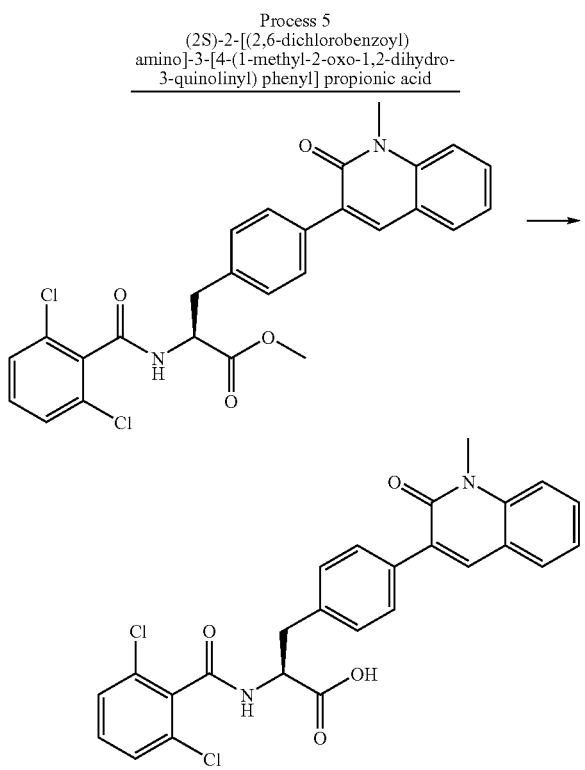

Process 5
(2S)-2-[(2,6-dichlorobenzoyl)amino]-3-[4-(1-methyl-2-oxo-1,2-dihydro-3-quinolinyl) phenyl] propionic acid Lithium hydroxide monohydrate (3 mg), tetrahydrofuran (800 μl), methanol (200 μl) and water (200 μl) were added to the compound obtained in Process 4 (10 mg) and stirred at room temperature for three hours. The reaction solution was diluted with ethyl acetate, washed with 1N hydrochloric acid and dried over magnesium sulfate to remove the solvent. The residue was purified with a reverse phase HPLC (water-acetonitrile, each containing 0.1% TFA) to obtain the title compound (7 mg).

MS (ESI MH+): 495

CHNO: C26H20Cl2N2O4

NMR data of the compound of Example 1: $^1$H-NMR (300 MHz, CDCl$_3$) 3.33 (2H, brd, J=5.1 Hz), 3.78 (3H, s), 5.24 (1H, m), 6.64 (1H, m), 7.18-7.40 (6H, m), 7.54-7.60 (4H, m), 7.77 (1H, s).

EXAMPLE 2

Synthesis of the Compound of the Following General Formula (12) which has Substituents of Example 2 of Table 1

The compound of Example 2 of Table 1 was synthesized by the same procedure as that of Example 1 except that corresponding alkylation reagents were used instead of methyl iodide in Process 3 of Example 1.

EXAMPLES 3 TO 5

Synthesis of the compounds of the following general formula (12) which has substituents of Examples 3 to 5 of Table 1

The compounds of Examples 3 to 5 of Table 1 were synthesized by the same procedure as that of Example 1 except that corresponding 3-bromoquinoline derivatives having the substituents were used instead of 3-bromoquinoline in Process 2 of Example 1. Those 3-bromoquinoline derivatives having the substituents were synthesized by the same procedure as that of Referential Example 1. Though the synthesizing method of 3-bromo-6-chloroquinoline was shown in Referential Example 1, the derivatives having other substituents were synthesized by the same procedure.

(12)

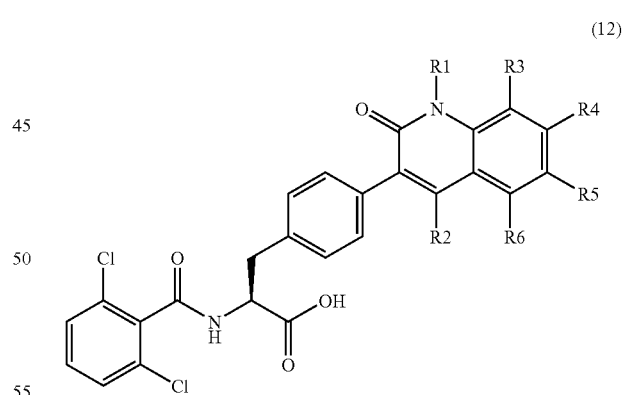

TABLE 1

| Example | R1- | R2- | R3- | R4- | R5- | R6- | MS Found (MH+) |
|---|---|---|---|---|---|---|---|
| 1 | Me— | H— | H— | H— | H— | H— | 495 |
| 2 | Et— | H— | H— | H— | H— | H— | 509 |
| 3 | Me— | H— | H— | H— | Cl— | H— | 529 |
| 4 | Me— | H— | H— | H— | NO2— | H— | 540 |
| 5 | Me— | H— | H— | H— | H— | NO2— | 540 |

R1, R2, R3, R4, R5 and R6 in Table 1 are the substituents in the formula (12).

EXAMPLE 6

Synthesis of the Compound of the Following General Formula (13) which has Substituents of Example 6 of Table 2

Process 1
3-iodo-4-methoxy-1-methyl-2(1H)-quinolinone

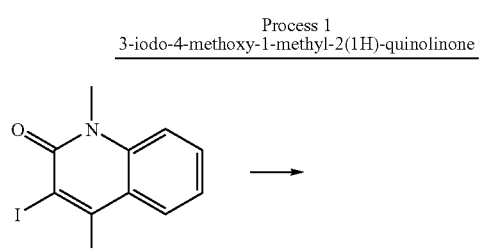

1M hexane solution of trimethylsilyldiazomethane (10 ml) and methanol (5 ml) were added to 4-hydroxy-3-iodo-1-methyl-2(1H)-quinolinone (500 mg) and stirred at room temperature for one hour. The reaction solution was concentrated and purified with a silica gel chromatography (hexane-ethyl acetate) to obtain the title compound (479 mg).

MS (ESI MH+): 316

CHNO: C11H10INO2

Process 2
Methyl (2S)-2-[(t-butoxycarbonyl)amino]-3-[4-(4-methoxy-1-methyl-2-oxo-1,2-dihydro-3-quinolinyl) phenyl] propionate

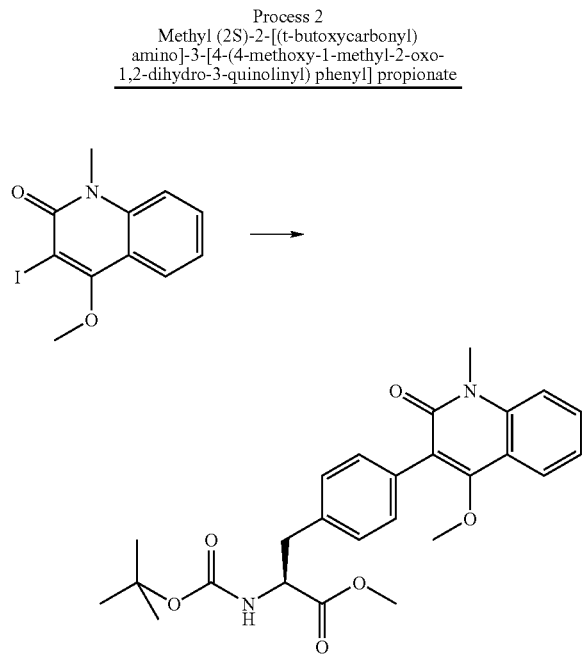

PdCl$_2$(dppf) (105 mg), an aqueous solution of 2M sodium carbonate (3.21 ml), the compound obtained in Process 1 of Example 1 (520 mg) and DMF (11 ml) were added to the compound obtained in Process 1 (445 mg) and stirred at 90° C. for 30 minutes. The reaction solution was diluted with ethyl acetate, washed with water and dried over magnesium sulfate to remove the solvent. The residue was purified with a silica gel chromatography (hexane-ethyl acetate) to obtain the title compound (387 mg).

MS (ESI MH+): 467

CHNO: C26H30N2O6

Process 3
Methyl (2S)-2-[(2,6-dichlorobenzoyl)amino]-3-[4-(4-methoxy-1-methyl-2-oxo-1,2-dihydro-3-quinolinyl) phenyl] propionate

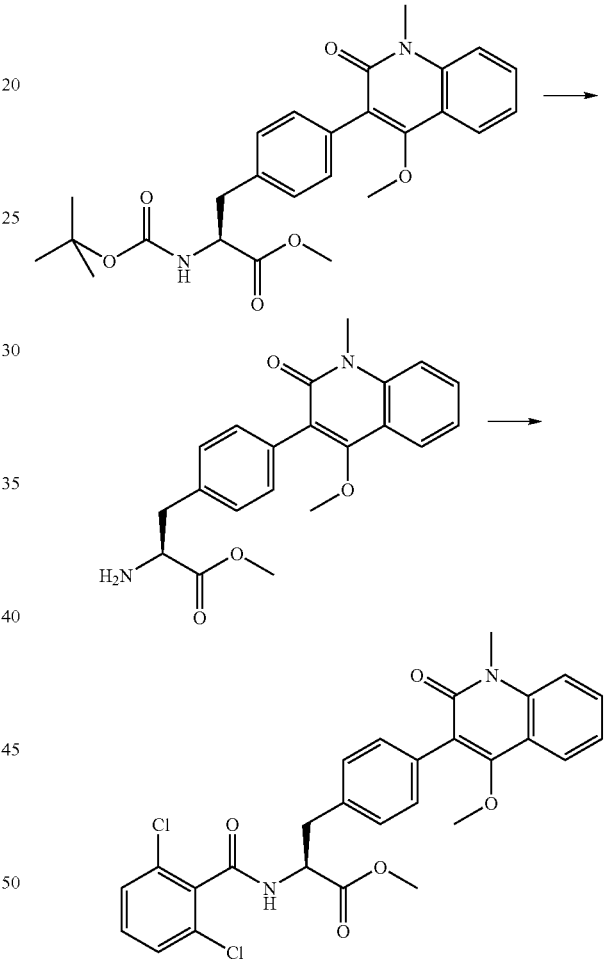

1,4-dioxane solution containing 4N hydrogen chloride (5 ml) was added to the compound obtained in Process 2 (387 mg) and stirred at room temperature for 30 minutes. The solvent was removed and 2,6-dichlorobenzoylchloride (190 μl), triethylamine (350 μl) and dichloromethane (4 ml) were added to the obtained residue and stirred for 16 hours. The solvent was removed and purified with a silica gel chromatography (hexane-ethyl acetate) to obtain the title compound (386 mg).

MS (ESI MH+): 539

CHNO: C28H24Cl2N2O5

Process 4
(2S)-2-[(2,6-dichlorobenzoyl) amino]-3-[4-(4-methoxy-1-methyl-2-oxo-1,2-dihydro-3-quinolinyl) phenyl] propionic acid

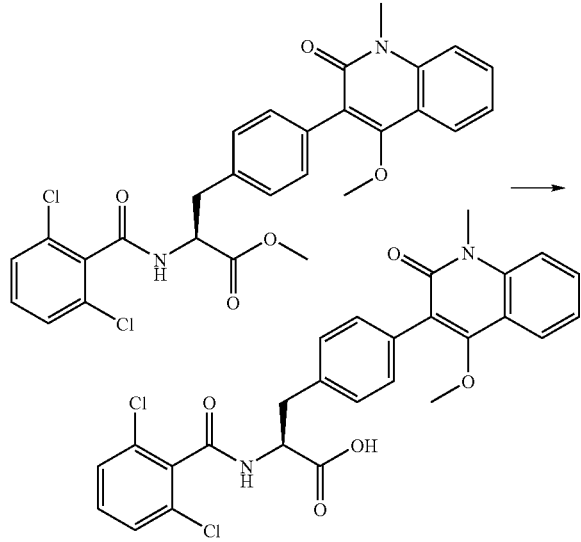

Lithium hydroxide monohydrate (10 mg), tetrahydrofuran (500 μl), methanol (30 μl) and water (30 μl) were added to the compound obtained in Process 3 (40 mg) and stirred at room temperature for one hour. The reaction solution was diluted with ethyl acetate, washed with 1N hydrochloric acid and dried over magnesium sulfate to remove the solvent. The residue was purified with a reverse phase HPLC (water-acetonitrile, each containing 0.1% TFA) to obtain the title compound (33 mg).

MS (ESI MH+): 525

CHNO: C27H22Cl2N2O5

NMR data of the compound of Example 6: $^1$H-NMR (300 MHz, DMSO-$d_6$) 2.98 (1H, dd, J=14.1, 9.9 Hz), 3.17 (1H, dd, J=14.1, 9.9 Hz), 3.42 (3H, s), 3.63 (3H, s), 4.70 (1H, m), 7.28-7.45 (9H, m), 7.56 (1H, d, J=8.4 Hz), 7.66 (1H, t, J=7.5 Hz), 7.90 (1H, d, J=8.4 Hz), 9.14 (1H, d, J=8.1 Hz).

EXAMPLE 7

Synthesis of the Compound of the Following General Formula (13) which has Substituents of Example 7 of Table 2

Process 1
(2S)-2-[(2,6-dichlorobenzoyl) amino]-3-[4-(4-hydroxy-1-methyl-2-oxo-1,2-dihydro-3-quinolinyl) phenyl] propionic acid

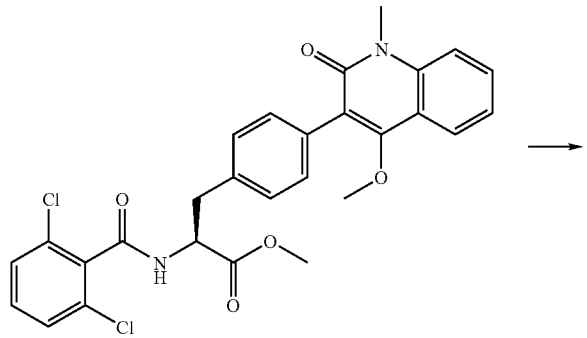

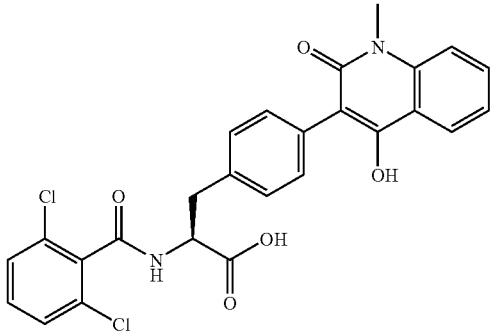

4N hydrogen chloride-dioxane solution (3 ml) and 1N hydrochloric acid (600 μl) were added to the compound obtained in Process 3 of Example 6 (175 mg) and stirred at 90° C. for four hours. The reaction solution was concentrated and purified with a reverse phase HPLC (water-acetonitrile, each containing 0.1% TFA) to obtain the title compound (118 mg).

MS (ESI MH+): 511

CHNO: C26H20Cl2N2O5

NMR data of the compound of Example 7: $^1$H-NMR (300 MHz, DMSO-$d_6$) 2.98 (1H, m), 3.15 (1H, m), 3.59 (3H, s), 4.71 (1H, m), 7.24-7.51 (9H, m), 7.63 (1H, t, J=7.5 Hz), 8.03 (1H, d, J=8.1 Hz), 9.13 (1H, d, J=8.2 Hz), 10.00 (1H, s).

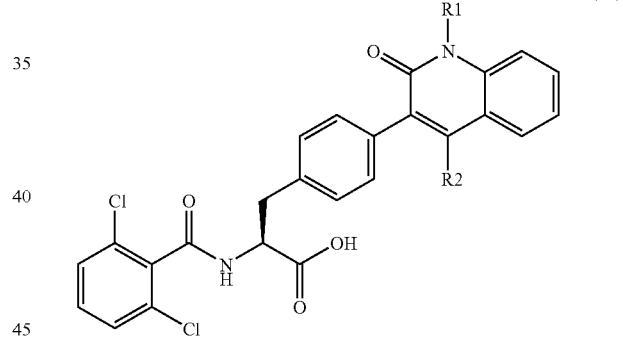

(13)

TABLE 2

| Example | R1- | R2- | MS Found (MH+) |
|---|---|---|---|
| 6 | Me— | MeO— | 525 |
| 7 | Me— | HO— | 511 |

R1 and R2 in Table 2 are the substituents in the formula (13).

EXAMPLE 8

Synthesis of (2S)-2-[[2-ethyl-2-(1-pyrrolidinecarbonyl) butanoyl]amino]-3-[4-(1-methyl-2-oxo-1,2-dihydro-3-quinolinyl) phenyl]propionic acid

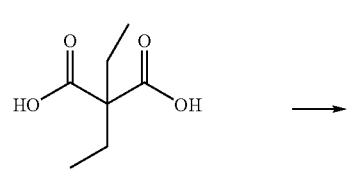

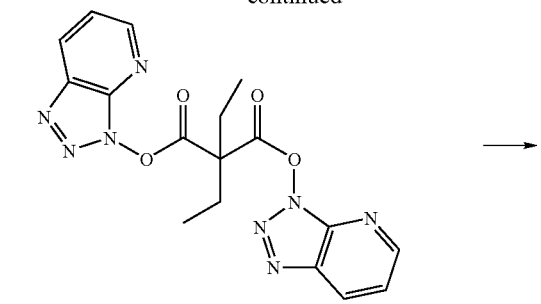

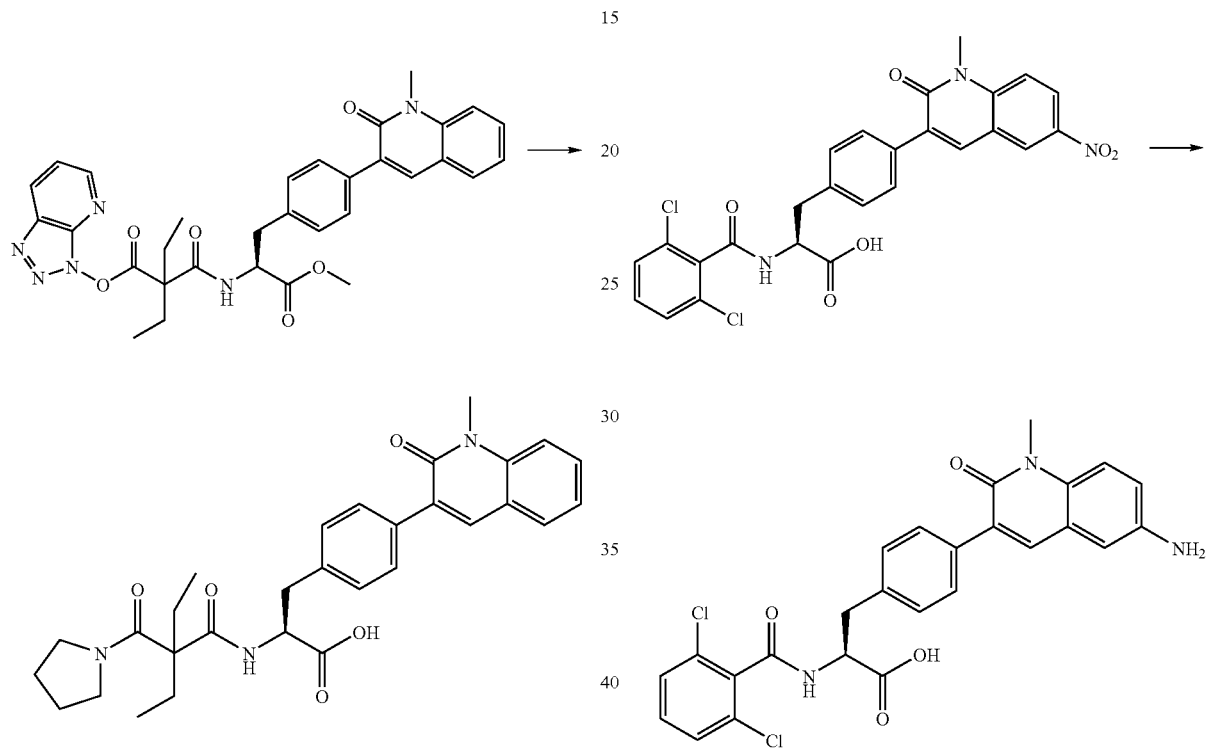

hydrogen chloride and 5 ml of water were added to the residue and stirred at 80° C. for three hours. The solvent was removed and the residue was purified with a reverse phase HPLC to obtain the title compound.

MS (ESI MH+) 518

EXAMPLE 11

Synthesis of the Compound of the Following General Formula (14) which has Substituents of Example 11 of Table 3

The mixture of 86.5 mg of diethylmalonic acid, 220 mg of 1-hydroxy-7-azabenzotriazol, 3 ml of NMP (1-methyl-2-pyrrolidinone) and 251 μl of 1,3-diisopropylcarbodiimide was stirred for one hour. The reaction mixture was diluted with ethyl acetate and washed with water and then the solvent was removed.

100 mg of methyl (2S)-2-amino-3-[4-(1-methyl-2-oxo-1,2-dihydro-3-quinolinyl) phenyl]propionate hydrochloride, 100 μl of diisopropylethylamine and 2 ml of NMP were added to the residue and stirred for one hour. The reaction mixture was diluted with ethyl acetate and washed with water and a saturated aqueous solution of sodium chloride and then the solvent was removed. The obtained residue was purified with a silica gel chromatography (ethyl acetate-hexane) to obtain a crude material of methyl (2S)-2-[[2-ethyl-2-[([1,2,3]triazolo [4,5-b]pyridine-3-yloxy)carbonyl] butanoyl]amino]-3-[4-(1-methyl-2-oxo-1,2-dihydro-3-quinolinyl)phenyl]propionate.

4 ml of NMP and 55 μl of pyrrolidine were added to the crude material and stirred at room temperature for two hours. The reaction mixture was diluted with ethyl acetate, washed with 1N hydrochloric acid and a saturated aqueous solution of sodium chloride and dried over magnesium sulfate to remove the solvent. 5 ml of dioxane containing 4N 7.5% palladium charcoal (containing 50% water) (3 mg) and ethyl acetate (1 ml) were added to the compound obtained in Example 4 (10 mg) and stirred under the hydrogen atmosphere at room temperature for 15 hours. After Celite filtration and removing the solvent, the residue was purified with a reverse phase HPLC (water-acetonitrile, each containing 0.1% TFA) to obtain the objective compound (2.0 mg).

MS (ESI MH+): 510

CHNO: C26H21Cl2N3O4

EXAMPLE 12

Synthesis of the Compound of the Following General Formula (14) which has Substituents of Example 12 of Table 3

The compound of Example 12 of Table 3 was synthesized by the same procedure as that of Example 11 except that the compound obtained in Example 5 was used as a raw material.

EXAMPLE 13

Synthesis of the Compound of the Following General Formula (14) which has Substituents of Example 13 of Table 3

Process 1 Reduction of nitro group

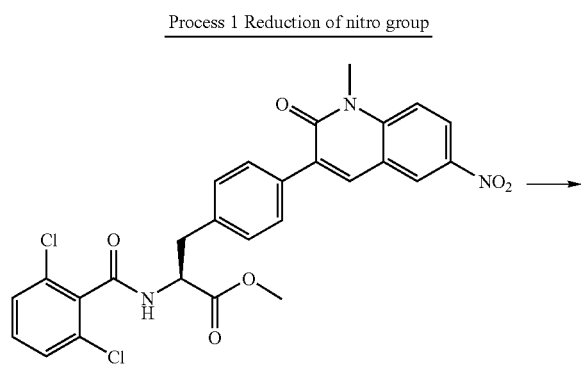

The compound obtained as a synthetic intermediate in Example 4, that is, methyl 2-[(2,6-dichlorobenzoyl)amino]-3-[4-(1-methyl-6-nitro-2-oxo-1,2-dihydro-3-quinolinyl)phenyl]propionate (64 mg) was treated by the same procedure as that of Example 11 to obtain the objective compound (40 mg).

MS (ESI MH+): 524

CHNO: C27H23Cl2N3O4

Process 2 Methylation

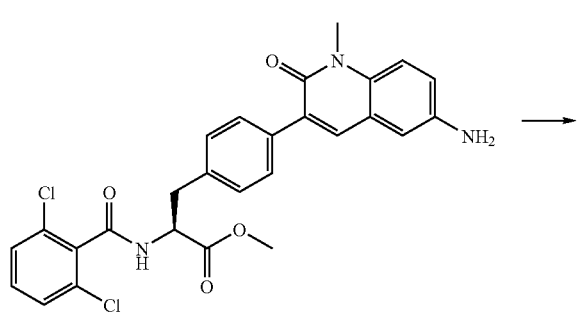

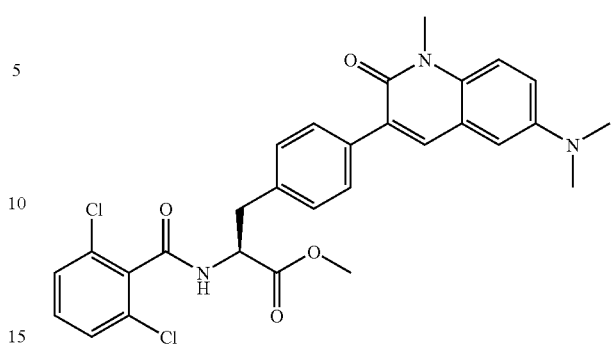

Methyl iodide (12 µl), calcium carbonate (8 mg) and DMF (200 µl) were added to the compound obtained in Process 1 (20 mg) and stirred at 60° C. for 20 hours. The reaction solution was concentrated and purified with a reverse phase HPLC (water-acetonitrile, each containing 0.1% TFA) to obtain the objective compound (3 mg).

MS (ESI MH+): 552

CHNO: C29H27Cl2N3O4

Process 3 Hydrolysis

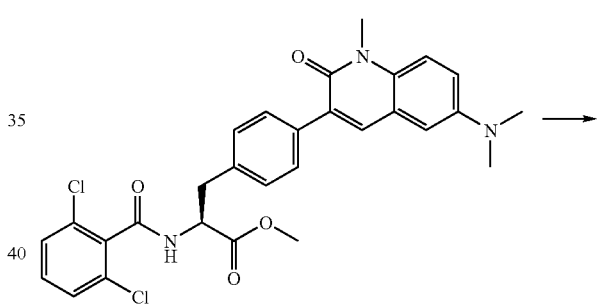

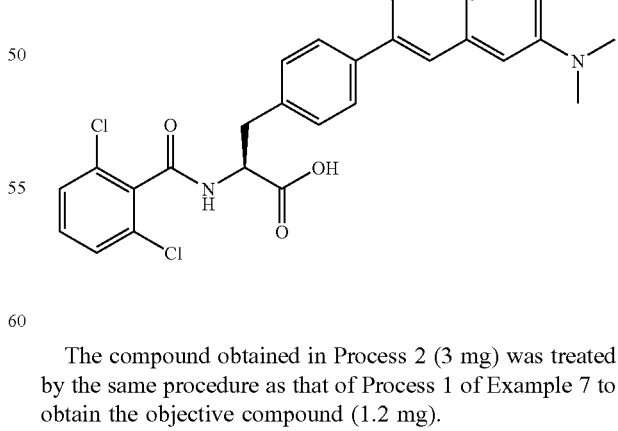

The compound obtained in Process 2 (3 mg) was treated by the same procedure as that of Process 1 of Example 7 to obtain the objective compound (1.2 mg).

MS (ESI MH+): 538

CHNO: C28H25Cl2N3O4

EXAMPLE 14

Synthesis of the Compound of the Following General Formula (14) which has Substituents of Example 14 of Table 3

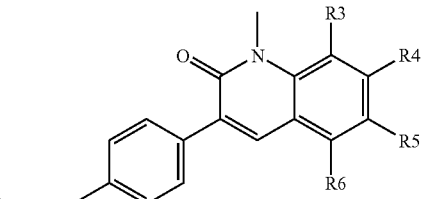

(14)

Process 1 Hydrolysis

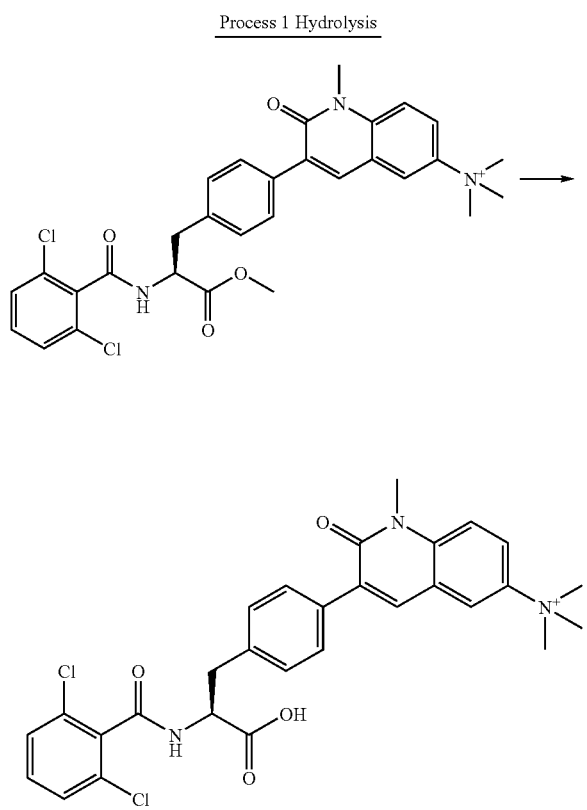

The compound obtained as a by-product material in Process 2 Example 13, that is, 3-(4-{(2S)-2-[(2,6-dichlorobenzoyl)amino]-3-methoxy-3-oxopropyl}phenyl)-N,N,N,1-tetramethyl-2-oxo-1,2-dihydro-6-quinolinaminium (10 mg) was treated by the same procedure as that of Process 1 of Example 7 to obtain the objective compound (6 mg).

MS (ESI MH+): 552

CHNO: C29H28Cl2N3O4

EXAMPLES 15 TO 16

Synthesis of the compounds of the following general formula (14) which has substituents of Examples 15 to 16 of Table 3

The compounds of Examples 15 to 16 of Table 3 were synthesized by the same procedure as that of Example 1 except that corresponding 3-bromoquinoline derivatives having the substituents were used instead of 3-bromoquinoline in Process 2 of Example 1.

TABLE 3

| Example | R6- | R5- | R4- | R3- | MS Found (MH+) |
|---|---|---|---|---|---|
| 11 | H— | NH$_2$— | H— | H— | 510 |
| 12 | NH$_2$— | H— | H— | H— | 510 |
| 13 | H— | (CH$_3$)$_2$N— | H— | H— | 538 |
| 14 | H— | (CH$_3$)$_3$N$^+$— | H— | H— | 552 |
| 15 | H— | Me— | H— | H— | 509 |
| 16 | H— | H— | Me— | H— | 509 |

R3, R4, R5 and R6 in Table 3 are the substituents in the formula (14).

EXAMPLE 17

Synthesis of the Compound of the Following General Formula (15) which has Substituents of Example 17 of Table 4

Process 1 Acylation

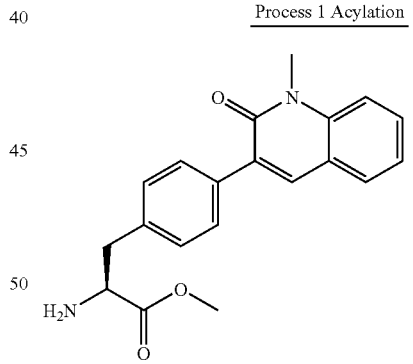

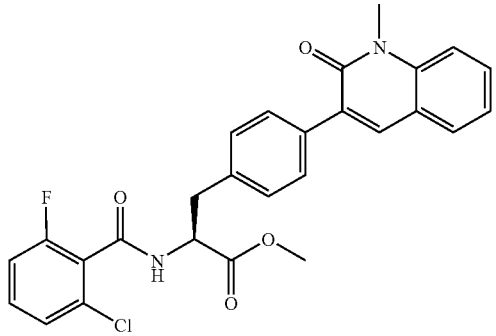

1-hydroxybenzotriazol monohydrate (37 mg), 2-chloro-6-fluorobenzoic acid (42 mg), triethylamine (34 μl), dichloromethane (2 ml) and 1-(3-dimethylaminopropyl)-3-ethylcarbodiimide hydrochloride (46 mg) were added to the compound obtained as a synthetic intermediate in Process 4 of Example 1, that is, a crude material of methyl (2S)-2-amino-3-[4-(1-methyl-2-oxo-1,2-dihydro-3-quinolinyl)phenyl]propionate hydrochloride (30 mg). After stirring the mixture at 30° C. for 24 hours, the reaction solution was concentrated. After adding ethyl acetate, the mixture was washed with 1N hydrochloric acid, saturated sodium bicarbonate water and a saturated aqueous solution of sodium chloride and dried over magnesium sulfate to remove the solvent. The residue was purified with a silica gel chromatography (hexane-ethyl acetate) to obtain the objective compound (40 mg).

MS (ESI MH+): 493

CHNO: C27H22ClFN2O4

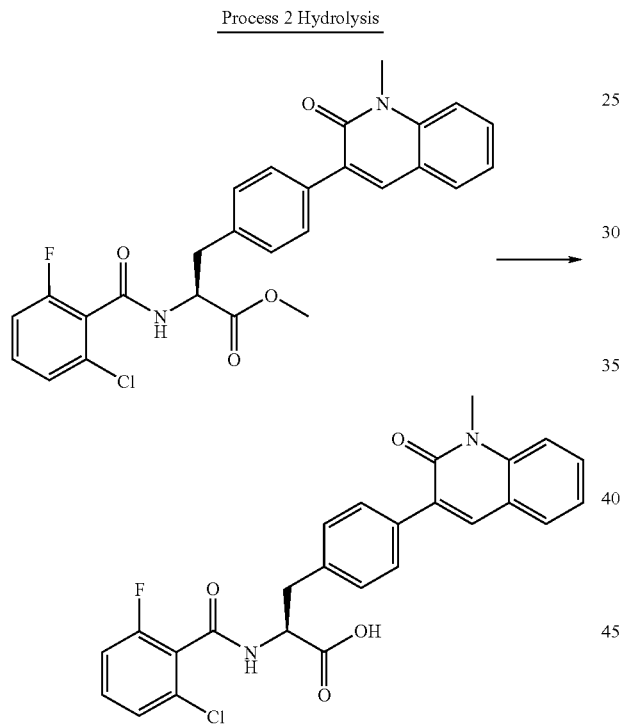

The compound obtained in Process 1 (40 mg) was treated by the same procedure as that of Process 1 of Example 7 to obtain the objective compound (27 mg).

MS (ESI MH+): 479

CHNO: C26H20ClFN2O4

EXAMPLES 18 TO 20

Synthesis of the compounds of the following general formula (15) which has substituents of Examples 18 to 20 of Table 4

The compounds of Examples 18 to 20 of Table 4 were synthesized by the same procedure as that of Example 17 except that corresponding carboxylic acid derivatives were used instead of 2-chloro-6-fluorobenzoic acid in Process 1 of Example 17. 2,4-dichloronicotinic acid used in the synthesis of the compound of Example 19 was synthesized in accordance with the method of Elena Marzi, et al. (Eur. J. Org. Chem. Vol. 7, p.1371, 2001)

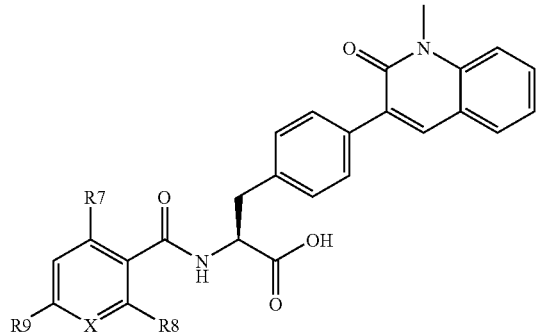

(15)

TABLE 4

| Example | R7— | R8— | R9— | X | MS Found (MH+) |
|---------|-----|-----|-----|------|----------------|
| 17 | F— | Cl— | H— | CH | 479 |
| 18 | Me— | Cl— | H— | CH | 475 |
| 19 | Cl— | Cl— | H— | N | 496 |
| 20 | Br— | Cl— | H— | CH | 539 |

R7, R8, R9 and X in Table 4 are the substituents or an atom(s) in the formula (15).

EXAMPLE 21

Synthesis of the Compound of the Following Formula (16)

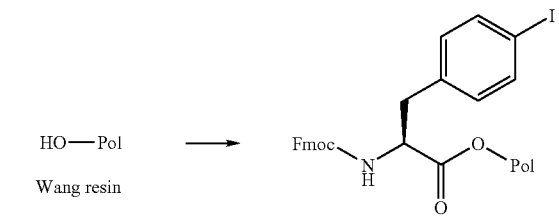

Process 1
Introduction of an amino acid(s) into resin 1.44 g of Wang resin (1.11 mmol/g) were washed with NMP and DCM alternately twice and then with NMP three times. 2.70 g of Fmoc-Phe(4-iodo)—OH in a solution of NMP (10 ml), 10.30 ml of pyridine in a solution of NMP (4 ml) and 0.755 ml of 2,6-dichlorobenzoyl chloride in a solution of NMP (3 ml) were added respectively to the resin and stirred at room temperature for 16 hours. After removing the excess solvent, the resin was washed with DMF three times, ethanol three times, DCM three times and NMP three times. NMP (7 ml) was added to the resin and 1.545 ml of pyridine in a solution of NMP (7 ml) and 1.506 ml of acetic anhydride in a solution of NMP (7 ml) were further added therein. After stirring the solution at room temperature for two hours, the reaction solution was removed and the resin was washed with DMF three times, ethanol three times and DCM three times. The obtained resin was dried under reduced pressure to obtain 2.22 g of the resin.

Process 2 Removal of Fmoc group

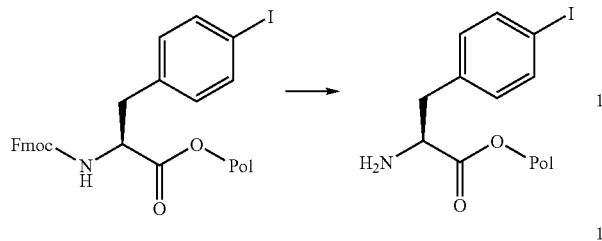

8 ml of a DMF solution of 20% piperidine was added to 0.789 g of the resin obtained in Process 1 and stirred for 5 minutes. After removing the solvent, 8 ml of a DMF solution of 20% piperidine was added again and stirred for 15 minutes. After removing the solvent, the resin was washed with DMF three times, ethanol three times and DCM three times.

Process 3 Acylation

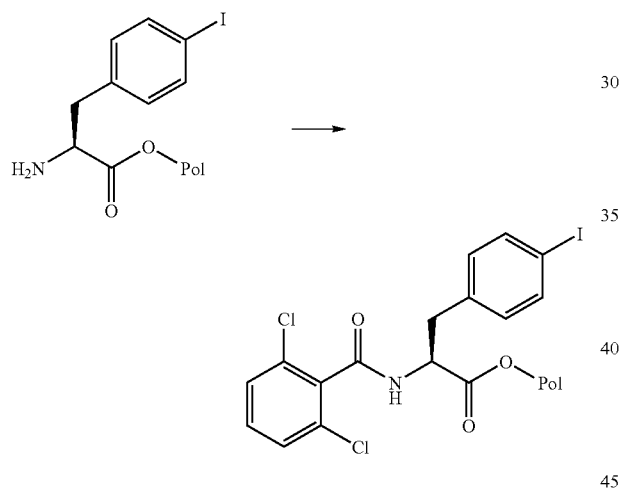

0.32 ml of pyridine in a solution of DCM (2 ml) and 0.34 ml of 2,6-dichlorobenzoyl chloride in a solution of DCM (3 ml) were added respectively to the resin obtained in Process 2 and stirred at room temperature for 16 hours. After removing the reaction solution, the resin was washed with DMF three times, ethanol three times and DCM three times. The obtained resin was dried under reduced pressure to obtain 0.772 g of the resin.

Process 4 Synthesis of boronate

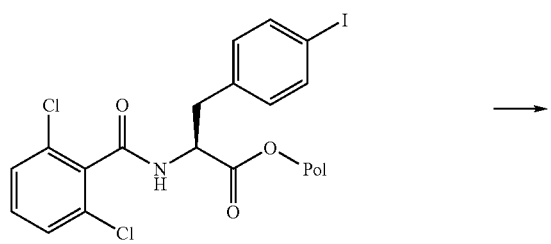

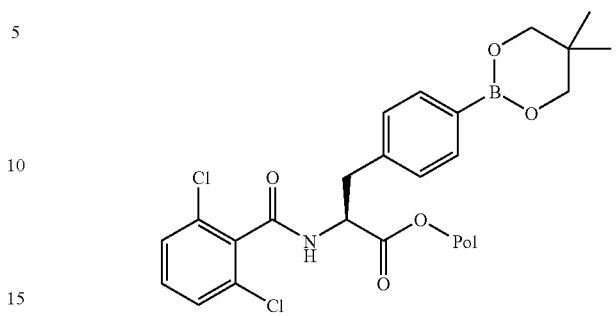

47.1 mg of dichlorobis(tricyclohexylphosphine)palladium(II), 800 mg of bis(neopentyl glycolato)diboron and 220 mg of potassium acetate were added to 436 mg of the resin obtained in Process 3. Degassed NMP (6 ml) was further added under the argon atmosphere. The mixture was reacted at 80° C. for one hour. After removing the reaction solution, the resin was washed with DMF, water, DMF, ethanol and DCM three times each. The obtained resin was dried under reduced pressure to obtain 0.403 g of the resin.

Process 5 Coupling reaction 261.3 mg of acetic anhydride copper(II) and Molecular Sieve 4A (79.1 mg) were added to 80.7 mg of the resin obtained in Process 4. 400.0 mg of 1(2H)-phthalazinone and 984 μl of diisopropylethylamine in a solution of NMP (4 ml) were further added therein and stirred at 50° C. for 23 hours. After removing the reaction solution, the resin was washed with DMF, water, ethanol and DCM three times each and dried under reduced pressure.

Process 6 Excision and purification

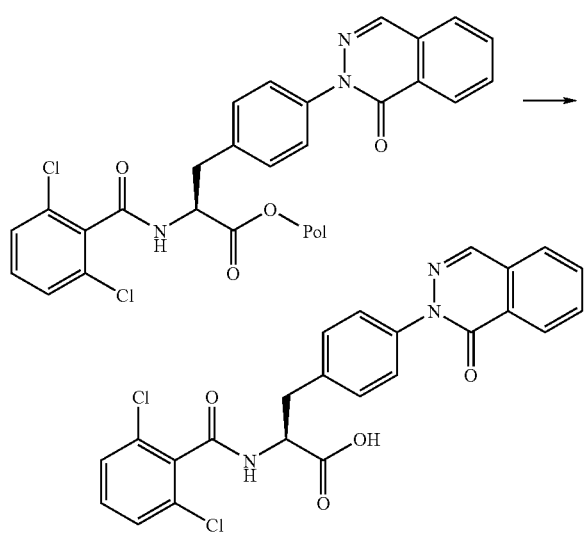

An aqueous solution of 95% trifluoroacetic acid (2 ml) was added to the resin obtained in Process 5 and stirred for 40 minutes. After filtration, an aqueous solution of 95% trifluoroacetic acid (2 ml) was further added to the resin and stirred for 40 minutes. After filtration, the resin was washed with acetonitrile (1 ml) twice. The filtering solvent and the cleaning solvent were concentrated together and purified with a reverse phase HPLC (Waters, Symmetry $C_{18}$ Column (5 μm; 19 mm φ*150 mm), Developing solvents: water, acetonitrile (TFA 0.05%)) to obtain 10.1 mg of the objective compound.

MS (ESI MH+): 482

CHNO: C24H17Cl2N3O4

(16)

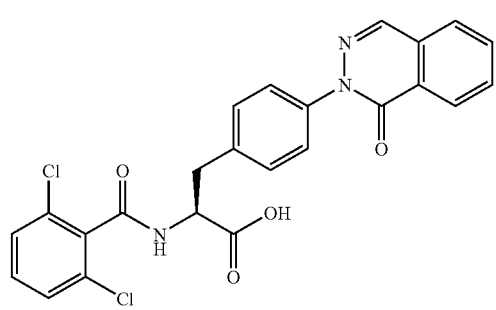

EXAMPLE 22

Synthesis of the Compound of the Following Formula (17)

Process 1 Preparation of resin

Wang resin

-continued

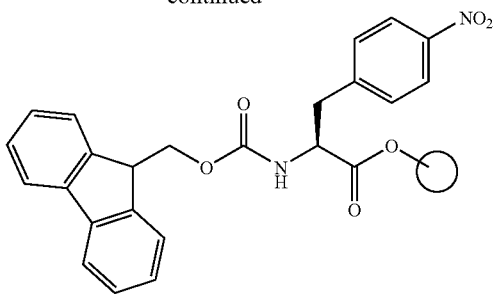

Fmoc-Phe(4-nitro)—OH (Fmoc: 9-fluorenylmethoxycarbonyl) (2.5 g), 2,6-dichlorobenzoyl chloride (0.745 mL) and pyridine (1.5 mL) in a solution of NMP (N-methyl-2-pyrrolidone) (25 mL) were added to Wang resin (0.76 mmol/g, 2.3 g) and stirred at room temperature for 16 hours. After removing the excess solvent, the resin was washed with DMF three times, dichloromethane three times and NMP twice. In order to conduct capping of an unreacted hydroxyl group on the resin, the resin was treated with acetic anhydride (20 mL), pyridine (20 mL) and NMP (20 mL) for 2 hours. After removing the excess solvent, the resin was washed with DMF three times and dichloromethane three times, and dried under reduced pressure.

Process 2 Removal of Fmoc group

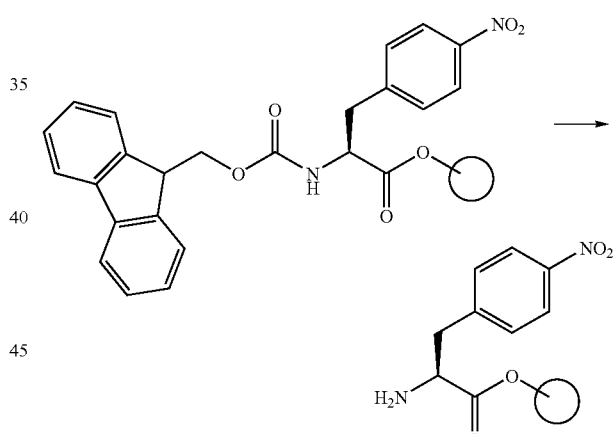

A DMF solution of 20% piperidine (25 mL) was added to the resin obtained in Process 1 and reacted for 15 minutes. After removing the solvent, the resin was washed with DMF and dichloromethane three times each, and dried under reduced pressure.

Process 3 Acylation reaction

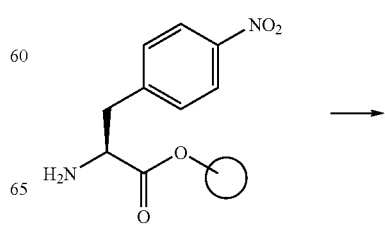

-continued

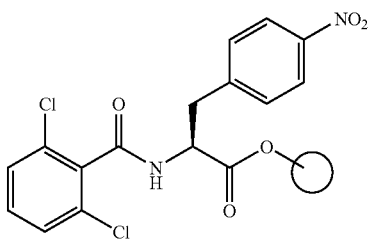

2,6-dichlorobenzoyl chloride (1.1 mL), 2,6-lutidine 1.6 mL) and NMP (26 mL) were added to 2.0 g of the resin obtained in Process 2 and reacted for 16 hours. After removing the excess solvent, the resin was washed with NMP and dichloromethane three times each, and dried under reduced pressure.

Process 4 Reduction of nitro group

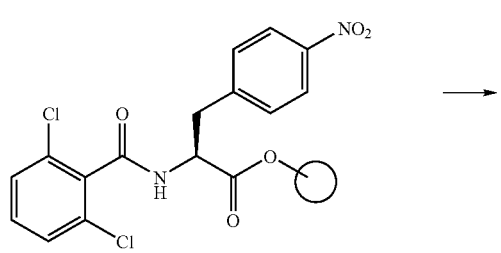

NMP (30 mL)·EtOH (1.5 mL) solution of $SnCl_2·2H_2O$ (15.0 g) was added to 1.5 g of the resin obtained in Process 3 and reacted for 16 hours. After removing the reaction solvent, the resin was washed with NMP and dichloromethane three times each, and dried under reduced pressure.

Process 5 Acylation reaction

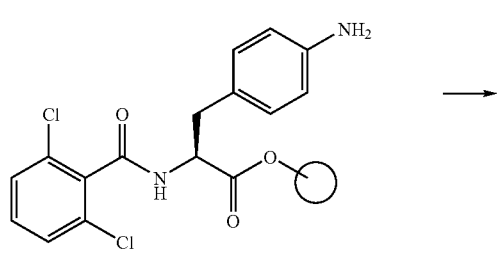

-continued

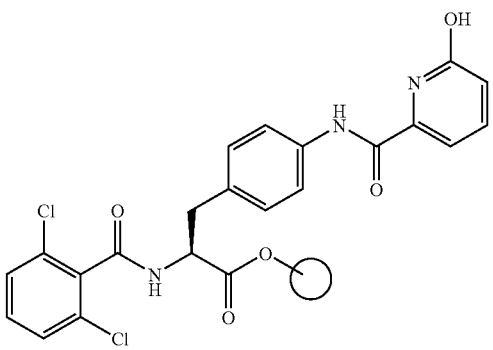

6-hydroxypicolinic acid (285 mg), diisopropylcarbodiimide (DICD) (159 μl) and 1-hyrdoxy-7-azabenzotriazol (HOAt) (279 mg) were added to NMP (5.75 ml) and stirred at room temperature for one hour. The resin obtained in Process 4 (250 mg) was added to this solution and stirred at room temperature for 14 hours. After removing the reaction solution, the resin was washed with NMP, methanol and dichloromethane three times each, and dried under reduced pressure.

Process 6 Ring closure, Excision from the resin

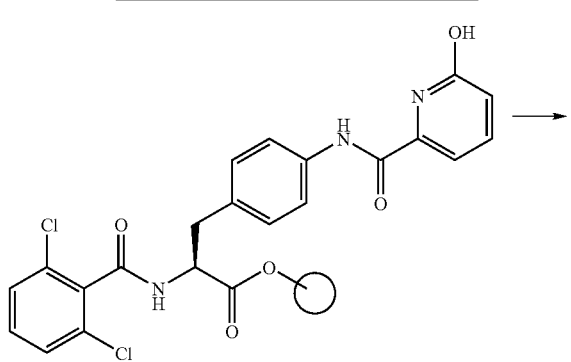

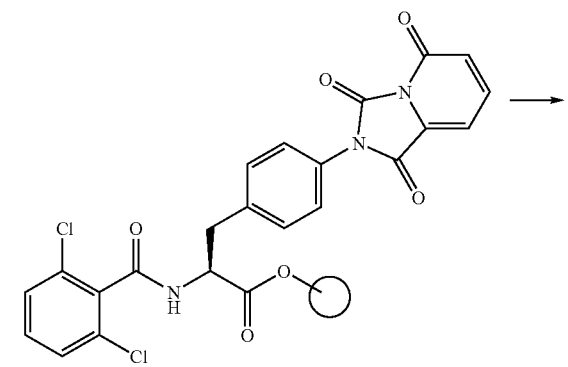

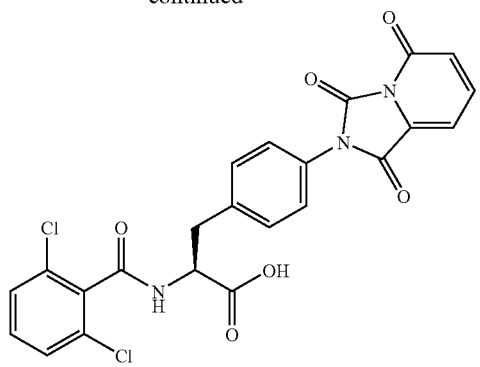

CDI (carbonyldiimidazole) (200 mg) and decahydronaphthalene (2 ml) were added to the resin obtained in Process 5 (260 mg) and stirred at 95° C. for 20 hours. After removing the reaction solution, the resin was washed with DMF, methanol and dichloromethane three times each and treated with trifluoroacetic acid containing 5% of water for 1 hour. After filtration, the filtrate was concentrated under reduced pressure. The residue was purified with a high-pressure liquid chromatography (water-acetonitrile, each containing 0.1% TFA) to obtain 26 mg of the intended compound.

MS (ESI MH+): 500

CHNO: C23H15Cl2N3O6

(17)

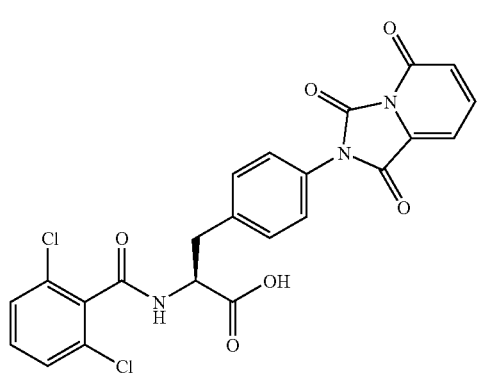

EXAMPLE 23

Synthesis of the Compound of the Following Formula (18)

Process 1 2-nitrobenzenesulfonylation, alkylation

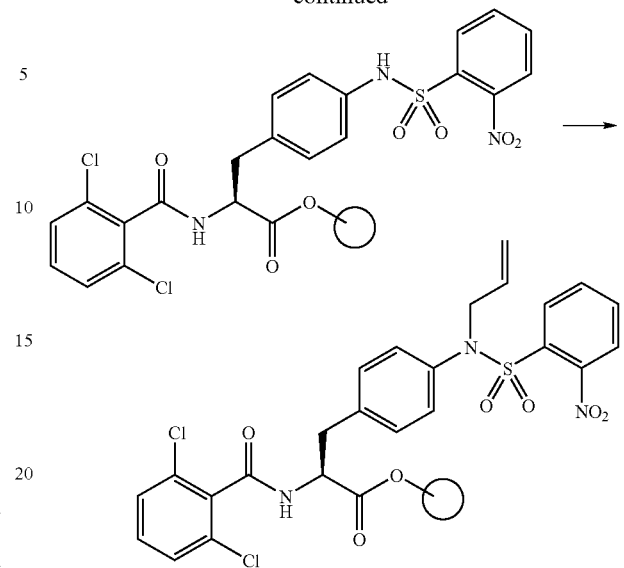

2-nitrobenzenesulfonyl chloride (400 mg), 2,6-lutidine (400 µl) and dichloromethane (8 ml) were added to the resin obtained in Process 4 of Example 22 (400 mg) and stirred at 4° C. for 19 hours. After removing the reaction solution, the resin was washed with NMP, methanol and dichloromethane three times each, and dried under reduced pressure. Allyl-bromide (800 µl), diisopropylethylamine (DIEA) (800 µl) and NMP (4 ml) were added to the obtained resin and stirred at room temperature for 15 hours. The resin was washed with water, NMP, methanol and dichloromethane three times each, and dried under reduced pressure.

Process 2 Removal of 2-nitrobenzenesulfonyl group

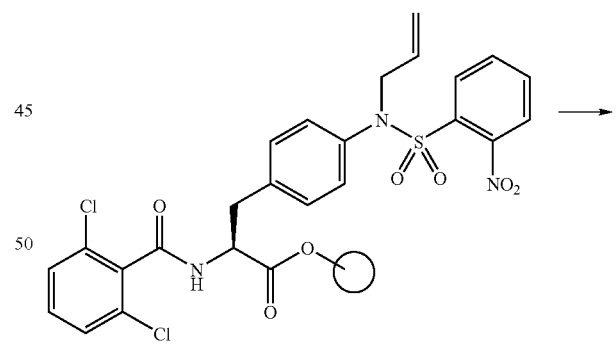

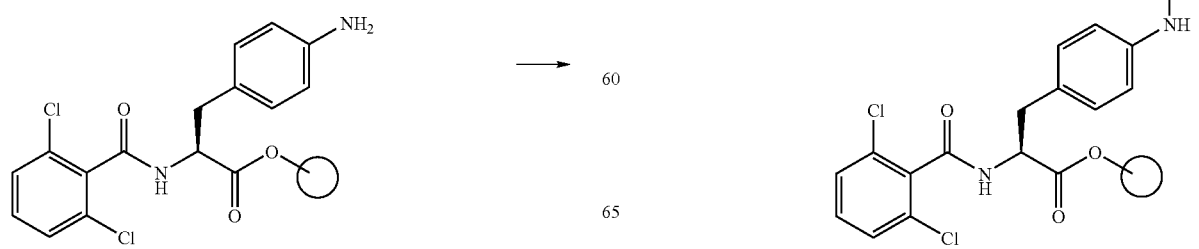

DBU (1,8-diazabicyclo[5.4.0]undec-7-ene) (300 μl), 2-mercaptoethanol (600 μl) and NMP (3 ml) were added to the resin obtained in Process 1 (400 mg) and stirred for 15 minutes. After removing the reaction solution, the resin was washed with NMP, methanol and dichloromethane three times each, and dried under reduced pressure.

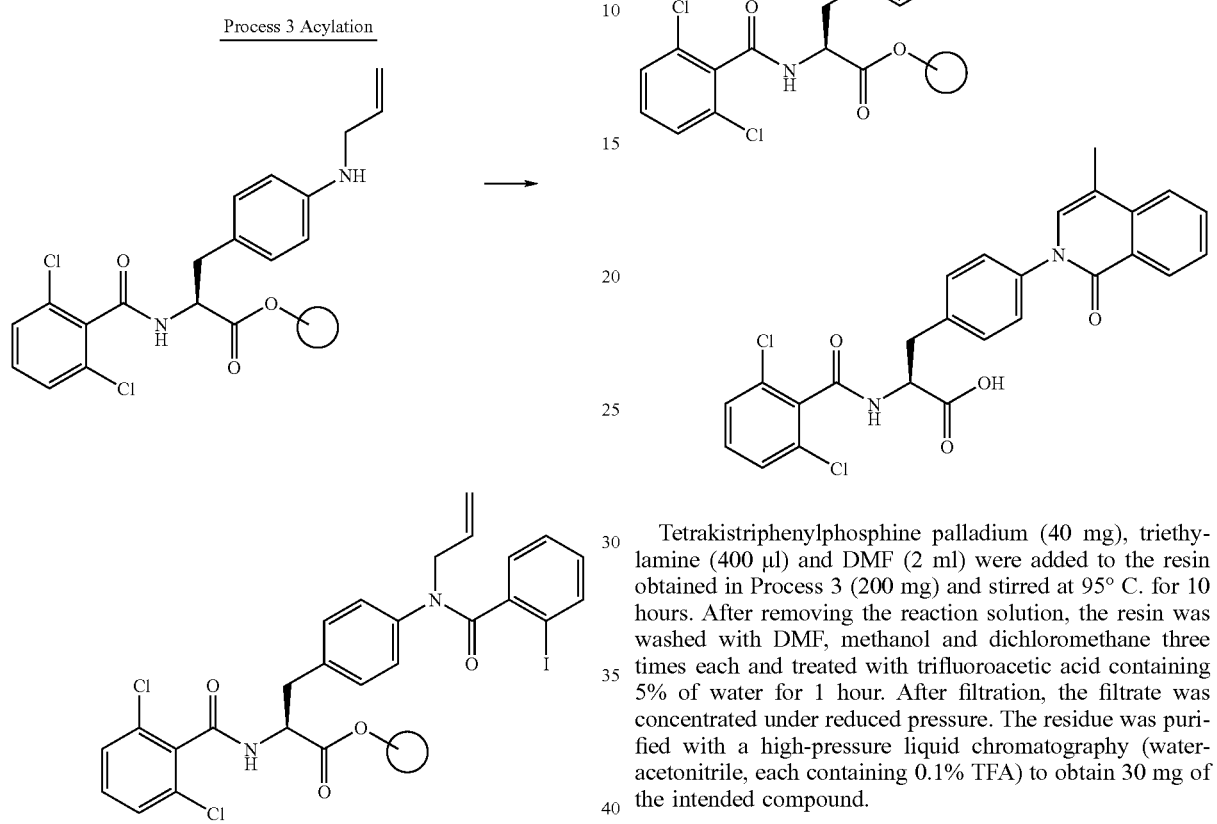

2-iodobenzoic acid chloride (200 mg), DIEA (400 μl) and NMP (4 ml) were added to the resin obtained in Process 2 (400 mg) and stirred at room temperature for 13 hours. After removing the reaction solution, the resin was washed with NMP, methanol and dichloromethane three times each, and dried under reduced pressure.

Tetrakistriphenylphosphine palladium (40 mg), triethylamine (400 μl) and DMF (2 ml) were added to the resin obtained in Process 3 (200 mg) and stirred at 95° C. for 10 hours. After removing the reaction solution, the resin was washed with DMF, methanol and dichloromethane three times each and treated with trifluoroacetic acid containing 5% of water for 1 hour. After filtration, the filtrate was concentrated under reduced pressure. The residue was purified with a high-pressure liquid chromatography (water-acetonitrile, each containing 0.1% TFA) to obtain 30 mg of the intended compound.

MS (ESI MH+): 495

CHNO: C26H20Cl2N2O4

NMR data of the compound of Example 23: $^1$H-NMR (300 MHz, DMSO-$d_6$) 2.30 (3H, s), 2.95-3.30 (2H, m), 4.75 (1H, m), 7.20 (1H, s), 7.30-7.55 (7H, m), 7.60 (1H, t), 7.75 (1H, d), 7.85 (1H, t), 8.30 (1H, d), 9.15 (1H, d).

EXAMPLE 24

Synthesis of the Compound of the Following Formula (19)

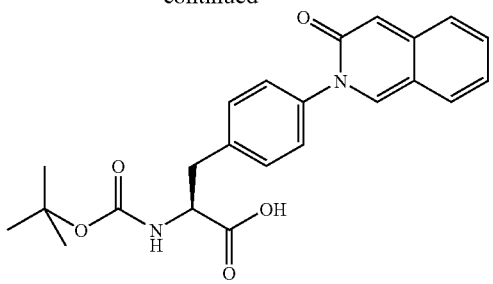

The mixture of 98 mg of (2S)-2-[(t-butoxycarbonyl)amino]-3-[4-(dihydroxyboranyl)phenyl]propionic acid, 46 mg of 3-hydroxyisoquinoline, 43 mg of copper acetate(II), 175 μl of triethylamine and 10 ml of dichloromethane was stirred for two days and diluted with ethanol. After Celite filtration, the filtering solvent was concentrated and the obtained residue was diluted with ethyl acetate. After extraction by an aqueous solution of 1N sodium hydroxide, the water phase was acidified by hydrochloric acid. The organic phase was extracted with ethyl acetate. The residue was washed with a saturated aqueous solution of sodium chloride and dried over magnesium sulfate to remove the solvent. The obtained residue was split by HPLC to obtain the objective compound.

H-NMR (CDCl3) δ 1.45 (9H, s), 3.20 (2H, m), 4.60 (1H, m), 5.30 (1H, m), 7.00-7.60 (9H, m), 8.35 (1H s).

MS (ESI, m/z) 409 (MH+)

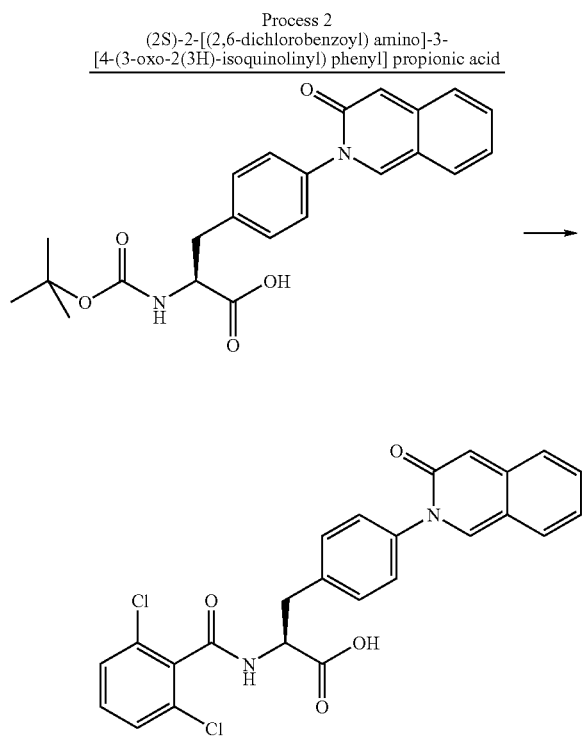

After being synthesized by the same procedure as that of Process 4 of Example 1 except that (2S)-2-[(t-butoxycarbonyl)amino]-3-[4-(3-oxo-2(3H)-isoquinolinyl)phenyl]propionic acid was used as a starting material, the objective compound was obtained by the same hydrolysis and purification procedures as those in Process 1 of Example 7.

MS (ESI MH+): 481

CHNO: C25H18Cl2N2O4

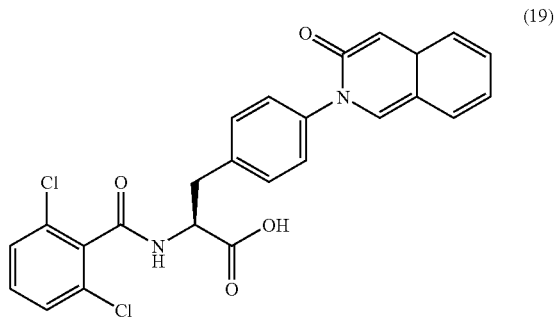

EXAMPLE 25

Synthesis of the Compound of the Following Formula (20)

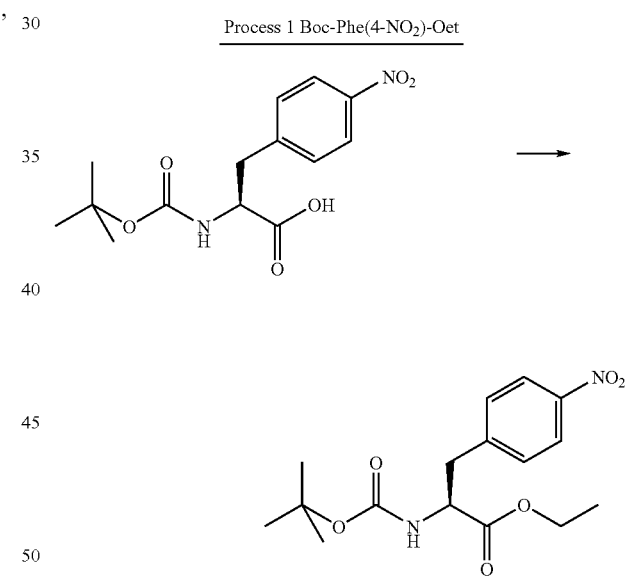

5 g of Boc-Phe(4—NO2)—OH, 3.09 g of 1-(3-dimethylaminopropyl)-3-ethylcarbodiimide hydrochloride, 5 ml of ethanol and 2 g of dimethylaminopyridine were stirred in dichloromethane for three days. The reaction mixture was washed with 1N hydrochloric acid, a saturated aqueous solution of sodium hydrogen carbonate and a saturated aqueous solution of sodium chloride and dried over magnesium sulfate. The solvent was removed to obtain the objective compound.

Yield: 4.6 g

H-NMR (CDCl3) δ 1.25 (3H, t), 1.40 (9H, s), 3.05-3.35 (2H, m), 4.20 (2H, q), 4.60 (1H, m), 5.10 (1H, br), 7.35 (2H, d), 8.15 (2H, d).

Process 2 Boc-Phe(4-NH₂)-Oet

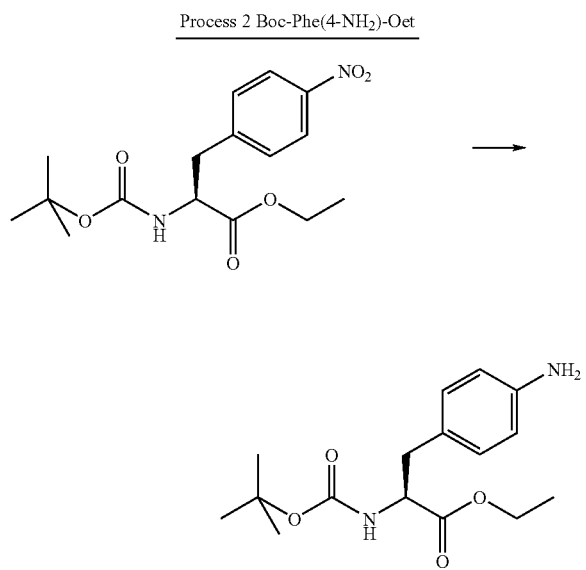

The mixture of 4.6 g of Boc-Phe(4—NO₂)—Oet, 900 mg of 10% palladium charcoal (containing 50% water) and ethanol was stirred overnight under the hydrogen atmosphere. After Celite filtration, the solvent was removed to obtain the objective compound.

Yield: 4.4 g

H-NMR (CDCl₃) δ 1.25 (3H, t), 1.40 (9H, s), 2.95 (2H, br), 4.15 (2H, q), 4.45 (1H, m), 4.95 (1H, br), 6.60 (2H, d), 6.95 (2H, d).

Process 3
Ethyl (2S)-2-amino-3-[4-(4-methyl-1,3-dioxo-1,3-dihydroisoindol-2-yl) phenyl] propionate hydrochloride

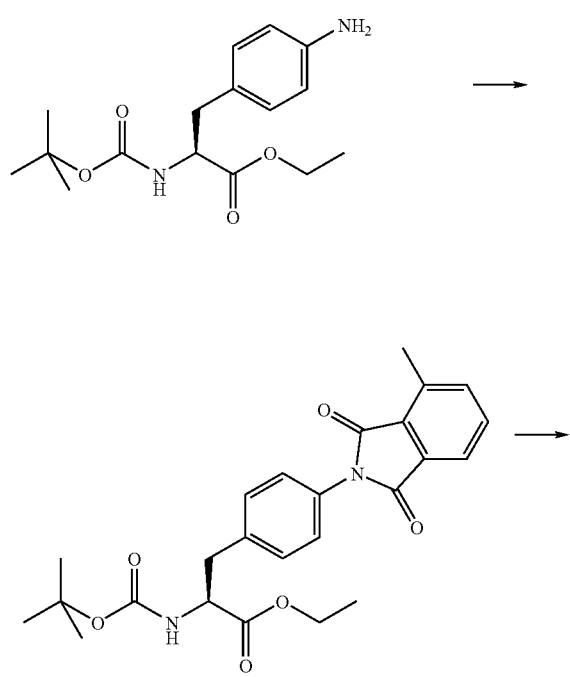

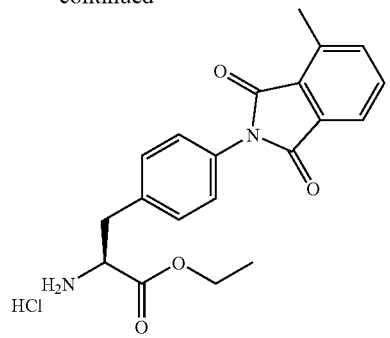

The mixture of 2.75 g of Boc-Phe(4—NH₂)—Oet, 1.67 g of 3-methyl phthalic anhydride and 40 ml of benzene was heated to reflux. After adding ethyl acetate, the mixture was washed with 1N hydrochloric acid, an aqueous solution of 1N sodium hydroxide and a saturated aqueous solution of sodium chloride and dried over magnesium sulfate to remove the solvent. Dioxane containing 4N hydrogen chloride was added to ethyl (2S)-2-(t-butoxyamino)-3-[4-(4-methyl-1,3-dioxo-1,3-dihydro-isoindol-2-yl)phenyl]propionate obtained by washing the residue with hexane, and stirred for two hours. The solvent was removed and the residue was washed with ethyl acetate to obtain the objective compound.

Yield: 1.9 g

H-NMR (DMSO-d6) δ 1.15 (3H, m), 2.65 (3H, s), 3.10-3.40 (2H, m), 4.15 (2H, m), 4.30 (1H, t), 7.40 (4H, s), 7.65-7.80 (3H, m), 8.70. (3H, br).

Process 4
Ethyl (2S)-2-[[2-ethyl-2-(1-pyrrolidinecarbonyl) butanoyl] amino]-3-[4-(4-methyl-1,3-dioxo-1,3-dihydroisoindol-2-yl) phenyl] propionate

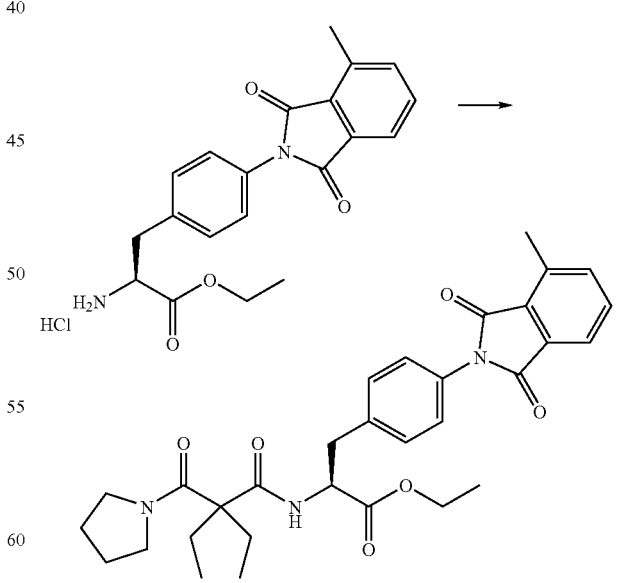

The mixture of 82.4 mg of diethylmalonic acid, 210 mg of 1-hydroxy-7-azabenzotriazole, 3 ml of 1-methyl-2-pyrrolidinone and 239 μl of 1,3-diisopropylcarbodiimide was stirred for four hours. The mixture was diluted with ethyl acetate, washed with water and a saturated aqueous solution of sodium chloride and dried over magnesium sulfate to remove, the solvent. 100 mg of ethyl (2S)-2-amino-3-[4-(4-methyl-1,3-dioxo-1,3-dihydroisoindol-2-yl)phenyl]propionate hydrochloride, 45 µl of diisopropylethylamine and 2 ml of 1-methyl-2-pyrrolidinone were added to the residue and stirred for four hours. The reaction mixture was diluted with ethyl acetate, washed with water and a saturated aqueous solution of sodium chloride and dried over magnesium sulfate to remove the solvent. The residue was purified with a silica gel chromatography (ethyl acetate-hexane) to obtain ethyl (2S)-2-[[2-ethyl-2-[([1,2,3]triazolo[4,5-b]pyridine-3-yloxy)carbonyl]butanoyl]amino]-3-[4-(4-methyl-1,3-dioxo-1,3-dihydroisoindol-2-yl)phenyl]propionate. 3 ml of 1-methyl-2-pyrrolidinone and 50.8 µl of pyrrolidine were added to the whole amount of the obtained compound and stirred for one hour. 1N hydrochloric acid was added therein and the reaction mixture was extracted with ethyl acetate, washed with water and a saturated aqueous solution of sodium chloride and dried over magnesium sulfate to remove the solvent. The residue was purified with a reverse phase HPLC to obtain the objective compound.

Yield: 66 mg

MS (ESI MH+): 548

CHNO: C31H37N3O6

NMR data of the compound of Example 25: H-NMR (DMSO-d6) δ 0.50-0.70 (6H, m), 1.20 (3H, t), 1.50-1.90 (8H, m), 2.65 (3H, s), 2.80 (1H, m), 2.90-3.40 (5H, m), 4.10 (2H, q), 4.60 (1H, m), 7.35 (2H, d), 7.45 (2H, d), 7.65-7.85 (3H, m), 8.05 (1H, d).

(20)

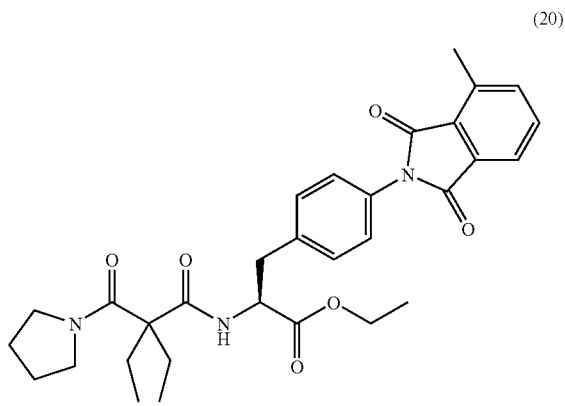

EXAMPLE 26

Synthesis of the Compound of the Following Formula (21)

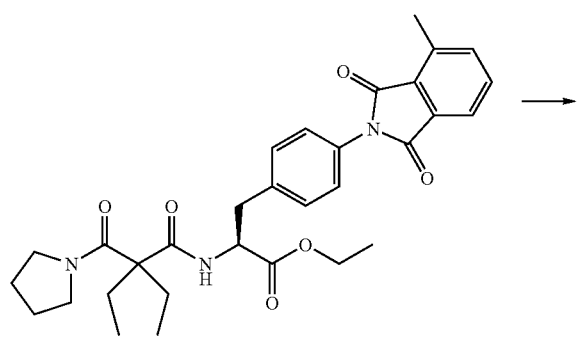

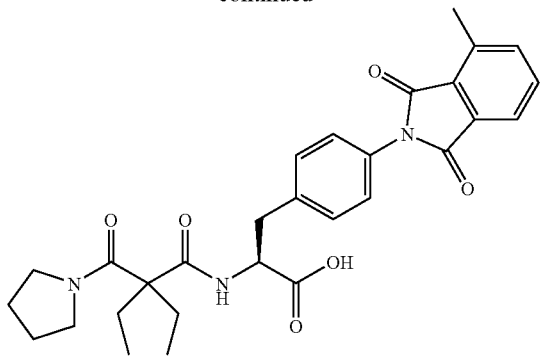

The objective compound was obtained by the same procedure as that of Process 1 of Example 7 except that ethyl (2S)-2-[[2-ethyl-2-(1-pyrrolidinecarbonyl)butanoyl]amino]-3-[4-(4-methyl-1,3-dioxo-1,3-dihydroisoindol-2-yl)phenyl]propionate obtained in Example 25 was used as a starting material.

MS (ESI MH+): 520

CHNO: C29H33N3O6

(21)

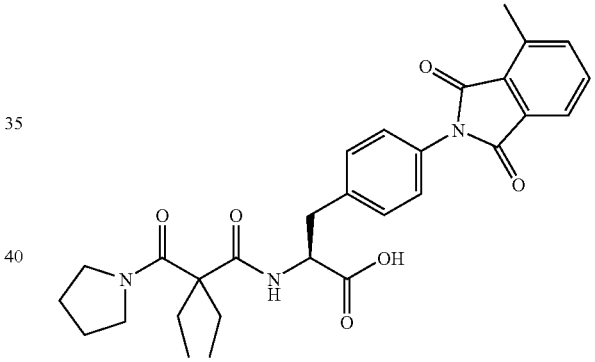

EXAMPLE 27

Synthesis of the Compound of the Following General Formula (24)

Process 1 Construction of quinazolinedione ring

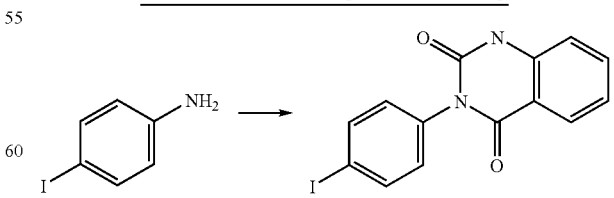

Acetonitrile (30 ml), tetrahydrofuran (6 ml) and 2-isocyanate methyl benzoate (1.33 g) were added to 4-aminoiodobenzene (1.5 g) and stirred at 70° C. for two hours. Triethylamine (1.14 ml) was further added and stirred at 70° C. for 12 hours. The precipitated objective material (2.17 g) was filtered and washed with acetonitrile.

MS (ESI MH+): 365

CHNO: C14H9IN2O2

Process 2 Methylation

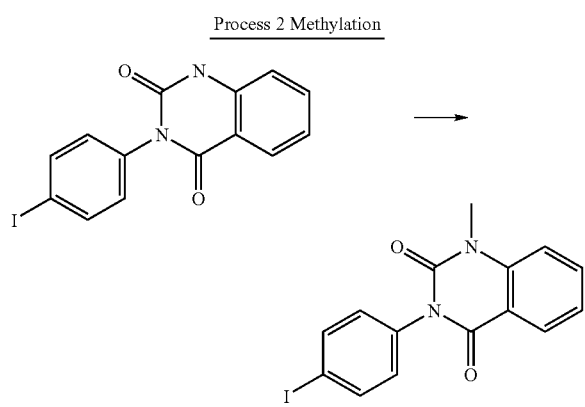

N,N'-dimethylformamide (40 ml), potassium carbonate (988 mg) and iodomethane (742 µl) were added to the compound obtained in Process 1 (2.17 g) and stirred at room temperature for four hours. The reaction solution was concentrated and ethyl acetate was added therein. The mixture was washed with 1N hydrochloric acid, saturated sodium bicarbonate water and a saturated aqueous solution of sodium chloride and dried over magnesium sulfate to remove the solvent. The residue was purified with a silica gel chromatography (dichloromethane-methanol) to obtain the objective compound (2.2 g).

MS (ESI MH+): 379

CHNO: C15H11IN2O2

Process 3 Acylation

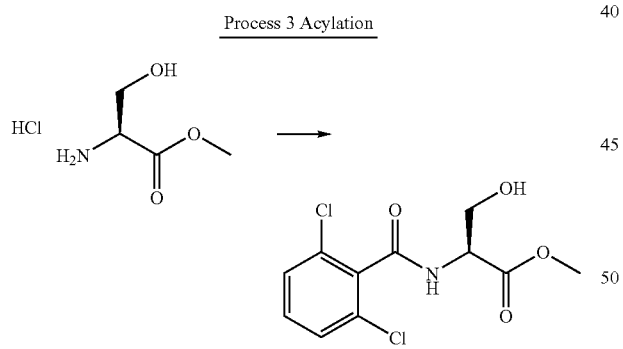

Dichloromethane (10 ml), 2,6-dichlorobenzoyl chloride (1.0 ml) and triethylamine (1.87 ml) were added to (D,L)-serine methyl hydrochloride (1.0 g) and stirred at room temperature for 13 hours. The reaction solution was concentrated and ethyl acetate was added therein. The mixture was washed with 1N hydrochloric acid, saturated sodium bicarbonate water and a saturated aqueous solution of sodium chloride and dried over magnesium sulfate. The solvent was removed to obtain a crude material of the objective compound (1.80 g).

MS (ESI MH+): 292

CHNO: C11H11Cl2NO4

Process 4 Dehydration reaction

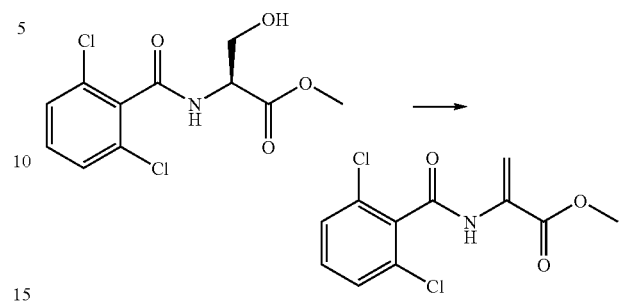

Dichloromethane (16 ml), triethylamine (1.3 ml) and methanesulfonyl chloride (444 µl) were added to the compound obtained in Process 3 (1.2 g) and stirred at room temperature for 13 hours. The reaction solution was concentrated and ethyl acetate was added therein. The mixture was washed with 1N hydrochloric acid, saturated sodium bicarbonate water and a saturated aqueous solution of sodium chloride and dried over magnesium sulfate to remove the solvent. The residue was purified with a. silica gel chromatography (hexane-ethyl acetate) to obtain the objective compound (797 mg).

MS (ESI MH+): 274

CHNO: C11H9Cl2NO3

Process 5 Coupling

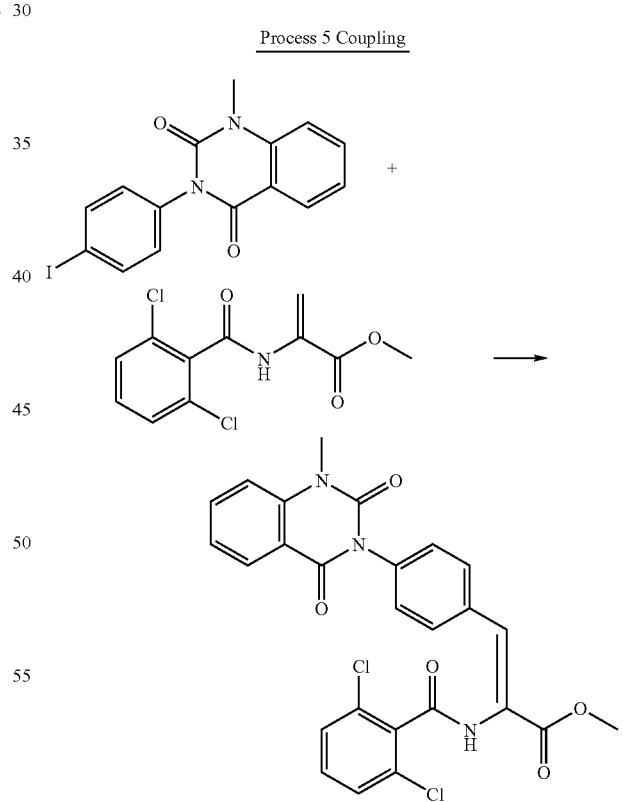

N,N'-dimethylformamide (17 ml), the compound obtained in Process 2 (1.21 g), triethylamine (1.3 ml), tetrabutylammonium chloride (892 mg) and palladium acetate (131 mg) were added to the compound obtained in Process 4 (800 mg) and stirred at 120° C. for two hours. The reaction solution was concentrated and ethyl acetate was added therein. The mixture was washed with 1N hydrochloric acid, saturated sodium bicarbonate water and a saturated aqueous solution of sodium chloride and dried over magnesium sulfate to remove the solvent. The residue was purified with a silica gel chromatography (hexane-ethyl acetate) to obtain the objective compound (850 mg).

MS (ESI MH+): 524

CHNO: C26H19Cl2N3O5

Process 6 Hydrolysis

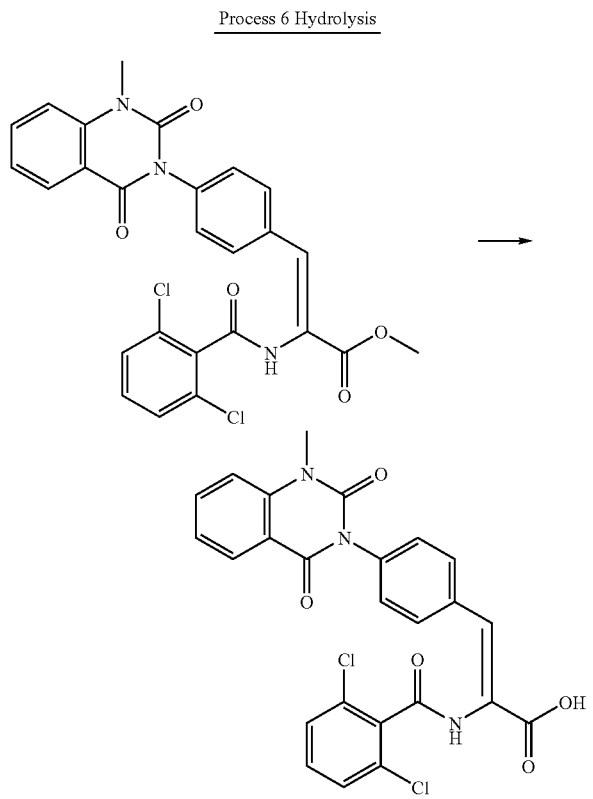

The objective compound (39 mg) was obtained by the same procedure as that of Process 1 of Example 7 except that the compound obtained in Process 5 (60 mg) was used.

MS (ESI MH+): 510

CHNO: C25H17Cl2N3O5.

NMR data of the compound of Example 27: $^1$H-NMR (300 MHz, DMSO-$d_6$) 3.54 (3H, s), 7.31-7.38 (4H, m), 7.43-7.55 (4H, m), 7.80-7.88 (3H, m), 8.06 (1H, dd, J=7.8 Hz, 1.2 Hz), 10.48 (1H, s).

(24)

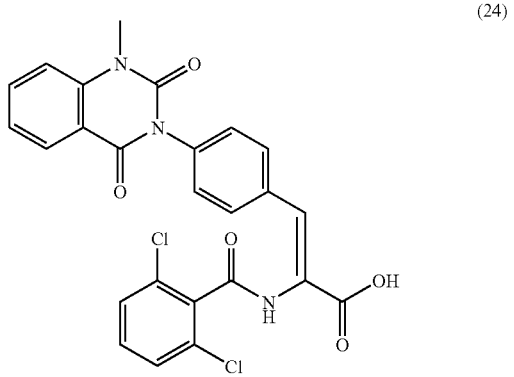

EXAMPLES 28 TO 30

Synthesis of the compounds of the above general formula (12) which has substituents of Examples 28 to 30 of Table 5

The compounds of Examples 28 to 30 of Table 5 were synthesized by the same procedure as that of Example 1 except that corresponding 3-bromoquinoline derivatives having the substituents were used instead of 3-bromoquinoline in Process 2 of Example 1. Those 3-bromoquinoline derivatives having the substituents were synthesized by the same procedure as that of Referential Example 1. Though the synthesizing method of 3-bromo-6-chloroquinoline was shown in Referential Example 1, the derivatives having other substituents were synthesized by the same procedure.

TABLE 5

| Example | R1- | R2- | R3- | R4- | R5- | R6- | MS Found (MH+) |
|---|---|---|---|---|---|---|---|
| 28 | Me— | H— | H— | H— | MeO— | H— | 525 |
| 29 | Me— | H— | H— | H— | iPr— | H— | 537 |
| 30 | Me— | H— | H— | H— | MeSO2— | H— | 573 |

R1, R2, R3, R4, R5 and R6 in Table 5 are the substituents in the formula (12).

EXAMPLES 31 TO 32

Synthesis of the compounds of the above general formula (15) which has substituents of Examples 31 to 32 of Table 6

The compounds of Examples 31 to 32 of Table 6 were synthesized by the same procedure as that of Example 17 except that corresponding benzoic acid derivatives having substituents were used instead of 2-chloro-6-fluorobenzoic acid in Process 1 of Example 17.

TABLE 6

| Example | R7- | R8- | R9- | X | MS Found (MH+) |
|---|---|---|---|---|---|
| 31 | Cl— | Cl— | MeSO2NH— | CH | 588 |
| 32 | Me— | Me— | H— | CH | 455 |

R7, R8, R9 and X in Table 6 are the substituents or an atom(s) in the formula (15).

EXAMPLE 33

Synthesis of the Compound of the Following General Formula (25)

Process 1 Demethylation 1M dichloromethane solution (1 ml) of BBr3 was added to the compound obtained in Example 28 (7 mg) and stirred at room temperature overnight. The reaction solution was concentrated and purified with a reverse phase HPLC (water-acetonitrile, each containing 0.1% TFA) to obtain the title compound (2 mg).

MS (ESI MH+): 511

CHNO: C26H20Cl2N2O5

(25)

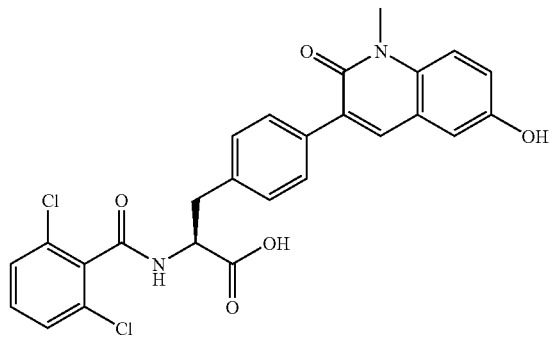

EXAMPLE 34

Synthesis of the Compound of the Following General Formula (26) which has Substituents of Example 34 of Table 7

Process 1 Acylation

The compound obtained as an intermediate in Process 3 of Example 6, that is, methyl (2S)-2-amino-3-[4-(4-methoxy-1-methyl-2-oxo-1,2-dihydro-3-quinolinyl)phenyl]propionate (50 mg) was acylated with 2-chloro-6-methylbenzoic acid by the same procedure as that of Process 1 of Example 17 to obtain methyl (2S)-2-[(2-chloro-6-methylbenzoyl)amino]-3-[4-(4-methoxy-1-methyl-2-oxo-1,2-dihydro-3-quinolinyl)phenyl]propionate (38 mg).

MS (ESI MH+): 519

CHNO: C29H27ClN2O5

Process 2 Hydrolysis

The compound obtained in Process 1 (20 mg) was hydrolyzed by the same procedure as that of Process 4 of Example 6 to obtain the objective compound (10 mg).

MS (ESI MH+): 505

CHNO: C28H25ClN2O5

EXAMPLES 35 TO 36

Synthesis of the compounds of the following general formula (26) which has substituents of Examples 35 to 36 of Table 7

The compounds of Examples 35 to 36 of Table 7 were synthesized by the same procedure as that of Example 34 except that corresponding benzoic acid derivatives having substituents were used instead of 2-chloro-6-methylbenzoic acid in Process 1 of Example 34.

(26)

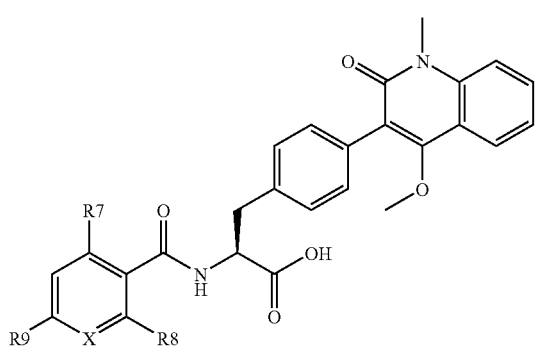

TABLE 7

| Example | R7- | R8- | R9- | X | MS Found (MH+) |
|---|---|---|---|---|---|
| 34 | Me— | Cl— | H— | CH | 505 |
| 35 | Cl— | Cl— | Cl— | CH | 559 |
| 36 | Cl— | Cl— | H— | N | 526 |

R7, R8, R9 and X in Table 7 are the substituents or an atom(s) in the formula (26).

EXAMPLES 37 TO 39

Synthesis of the compounds of the following general formula (27) which has substituents of Examples 37 to 39 of Table 8

The compounds of Examples 37 to 39 of Table 8 were synthesized by hydrolysis under the same conditions as those of Process 1 of Example 7 except that the compounds obtained in Process 1 of Examples 34 to 36 were used respectively.

(27)

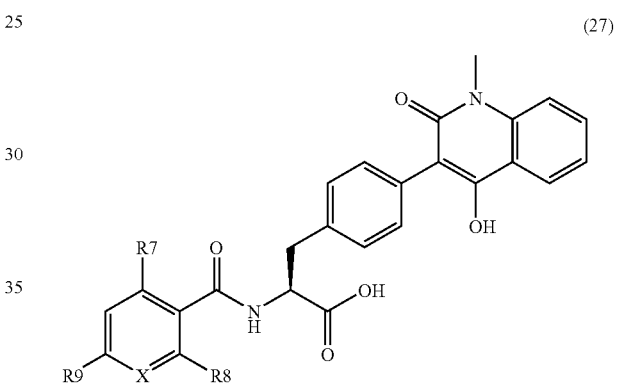

TABLE 8

| Example | R7- | R8- | R9- | X | MS Found (MH+) |
|---|---|---|---|---|---|
| 37 | Me— | Cl— | H— | CH | 491 |
| 38 | Cl— | Cl— | Cl— | CH | 545 |
| 39 | Cl— | Cl— | H— | N | 512 |

R7, R8, R9 and X in Table 8 are the substituents or an atom(s) in the formula (27).

EXAMPLE 40

Synthesis of the Compound of the Following General Formula (28) which has a Substituent(s) of Example 40 of Table 9

Process 1 O-alkylation

Tri-n-propyl orthoformate (5 ml) was added to the compound obtained in Example 7 (130 mg) and stirred at 150° C. for eight hours. The reaction mixture was diluted with ethyl acetate, washed with 1N hydrochloric acid, saturated sodium bicarbonate water and a saturated aqueous solution of sodium chloride and dried over magnesium sulfate to remove the solvent. The residue was purified with a silica gel chromatography (hexane-ethyl acetate) to obtain n-propyl (2S)-2-[(2,6-dichlorobenzoyl)amino]-3-[4-(4-n-propoxy-1-methyl-2-oxo-1,2-dihydro-3-quinolinyl)phenyl]propionate (60 mg).

MS (ESI MH+): 595

CHNO: C32H32Cl2N2O5

Process 2 Hydrolysis

The compound obtained in Process 1 (60 mg) was hydrolyzed by the same procedure as that of Process 4 of Example 6 to obtain the objective compound (21 mg).

MS (ESI MH+): 553

CHNO: C29H26Cl2N2O5

EXAMPLE 41

Synthesis of the Compound of the Following General Formula (28) which has a Substituent(s) of Example 41 of Table 9

The compound of Example 41 of Table 9 was synthesized by the same procedure as that of Example 40 except that ethyl orthoformate was used instead of tri-n-propyl orthoformate in Process 1 of Example 40.

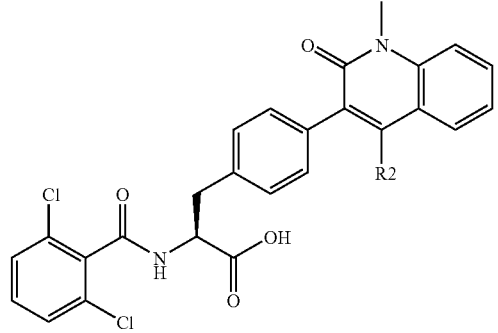

(28)

TABLE 9

| Example | R2- | MS Found (MH+) |
| --- | --- | --- |
| 40 | nPrO— | 553 |
| 41 | EtO— | 539 |

R2 in Table 9 is a substituent(s) in the formula (28).

EXAMPLE 42

Synthesis of the Compound of the Following General Formula (29) which has a Substituent(s) of Example 42 of Table 10

Process 1 N-Alkylation, Bromination

Methyl iodide (2.4 ml), potassium carbonate (5.4 g) and DMF (30 ml) were added to 4-methyl-2-quinolinol (3.18 g) and stirred at room temperature overnight. After removing the solvent, the reaction mixture was diluted with chloroform, washed with water and dried over magnesium sulfate to remove the solvent. N-bromosuccinimide (3.07 g) and methanol (120 ml) were added to the residue (2.5 g) and stirred at 90° C. for two hours. After removing the solvent, the residue was purified with a silica gel chromatography (hexane-ethyl acetate) to obtain 3-bromo-1,4-dimethyl-2(1H)-quinolinone (1.01 g).

MS (ESI MH+): 252

CHNO: C11H10BrNO

NMR data of 3-bromo-1,4-dimethyl-2(1H)-quinolinone: $^1$H-NMR (300 MHz, CDCl$_3$) 2.72 (3H, s), 3.82 (3H, s), 7.29 (1H, t, J=7.8 Hz), 7.39 (1H, d, J=9.0 Hz), 7.61 (1H, t, J=9.0 Hz), 7.80 (1H, d, J=8.1 Hz).

Process 2 Coupling

The compound obtained in Process 1 of Example 1 (300 mg) was treated by the same procedure as that of Process 2 of Example 1 except that the compound obtained in Process 1 of Example 42 was used instead of 3-bromoquinoline to obtain methyl 2-[(t-butoxycarbonyl)amino]-3-[4-(1,4-dimethyl-2-oxo-1,2-dihydro-3-quinolinyl)phenyl]propionate (50 mg).

MS (ESI MH+): 451

CHNO: C26H30N2O5

NMR data of methyl 2-[(t-butoxycarbonyl)amino]-3-[4-(1,4-dimethyl-2-oxo-1,2-dihydro-3-quinolinyl)phenyl]propionate: $^1$H-NMR (300 MHz, CDCl$_3$) 1.44 (9H, s), 2.32 (3H, s), 3.13 (2H, m), 3.73 (3H, s), 3.76 (3H, s), 4.62 (1H, m), 5.06 (1H, m), 7.21 (4H, s), 7.29 (1H, t, J=6.0 Hz), 7.41 (1H, d, J=8.4 Hz), 7.58 (1H, t, J=7.2 Hz), 7.81 (1H, d, J=7.8 Hz).

Process 3 Removal of Boc Group, Acylation

The compound obtained in Process 2 (50 mg) was treated by the same procedure as that of Process 3 of Example 6 to obtain methyl 2-[(2,6-dichlorobenzoyl)amino]-3-[4-(1,4-dimethyl-2-oxo-1,2-dihydro-3-quinolinyl)phenyl]propionate (50 mg).

MS (ESI MH+): 523

CHNO: C28H24Cl2N2O4

NMR data of methyl 2-[(2,6-dichlorobenzoyl)amino]-3-[4-(1,4-dimethyl-2-oxo-1,2-dihydro-3-quinolinyl)phenyl]propionate: $^1$H-NMR (300 MHz, CDCl$_3$) 2.31 (3H, s), 3.31 (2H, m), 3.74 (3H, s), 3.77 (3H, s), 5.24 (1H, m), 6.45 (1H, m), 7.17-7.32 (8H, m), 7.40 (1H, d, J=8.7 Hz), 7.58 (1H, t, J=9.0 Hz), 7.80 (1H, d, J=7.8 Hz).

Process 4 Hydrolysis

The compound obtained in Process 3 (30 mg) was treated by the same procedure as that of Process 1 of Example 7 to obtain the title compound (14 mg).

MS (ESI MH+): 509

CHNO: C27H22Cl2N2O4

NMR data of Example 42: $^1$H-NMR (300 MHz, DMSO-d$_6$) 2.26 (3H, s), 2.94-3.02 (1H, m), 3.18-3.24 (1H, m), 3.66 (3H, s), 4.75 (1H, m), 7.14 (2H, d, J=8.4 Hz), 7.25-7.46 (6H, m), 7.56 (1H, d, J=8.7 Hz), 7.65 (1H, t, J=6.0 Hz), 7.88 (1H, d, J=7.8 Hz), 9.14 (1H, d, J=8.1 Hz).

EXAMPLE 43

Synthesis of the Compound of the Following General Formula (29) which has a Substituent(s) of Example 43 of Table 10

The compound of Example 43 of Table 10 was synthesized by the same procedure as that of Example 42 except that a corresponding alkylating agent(s) was used instead of methyl iodide in Process 1 of Example 42.

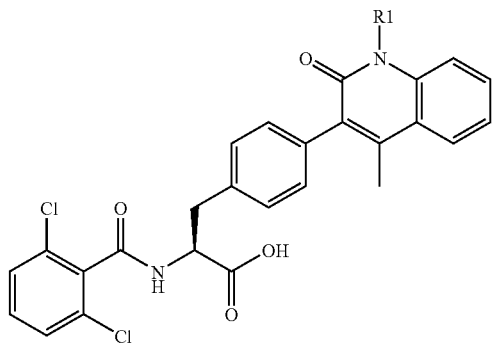

(29)

TABLE 10

| Example | R1- | MS Found (MH+) |
|---|---|---|
| 42 | Me— | 509 |
| 43 | Et— | 523 |

R1 in Table 10 is a substituent(s) in the formula (29).

EXAMPLE 44

Synthesis of the Compound of the Following Formula (30)

Process 1 Bromination, Methylation

The compound obtained in Referential Example 2 (600 mg) was suspended in an aqueous solution of potassium bromide (4.0 ml) and bromine (221 µl) diluted with an aqueous solution of potassium bromide (7.0 ml) was added therein. The mixture was stirred at room temperature overnight and precipitated crystals were filtered out. A hexane solution of 1M tetramethylsilyldiazomethane was added to the obtained residue until bubbles did not rise in the reaction solution, and then stirred for two hours. The solvent was removed and the residue was purified with a silica gel chromatography (hexane-ethyl acetate) to obtain 3-bromo-6-chloro-4-methoxy-1-methyl-2(1H)-quinolinone (200 mg).

MS (ESI MH+): 302

CHNO: C11H9BrClNO2

NMR date of 3-bromo-6-chloro-4-methoxy-1-methyl-2(1H)-quinolinone: $^1$H-NMR (300 MHz, CDCl$_3$) 3.77 (3H, s), 4.11 (3H, s), 7.33 (1H, d, J=9.0 Hz), 7.57 (1H, d, J=7.5 Hz), 7.88 (1H, s).

Process 2 Coupling, Removal of Boc Group and Acylation

The compound obtained in Process 1 (200 mg) was treated by the same procedures as those of Processes 2 and 3 of Example 42 to obtain methyl 3-[4-(6-chloro-4-methoxy-1-methyl-2-oxo-1,2-dihydro-3-quinolinyl)phenyl]-2-[(2,6-dichlorobenzoyl)amino]propionate (37 mg).

MS (ESI MH+): 573

CHNO: C28H23Cl3N2O5

NMR data of methyl 3-[4-(6-chloro-4-methoxy-1-methyl-2-oxo-1,2-dihydro-3-quinolinyl)phenyl]-2-[(2,6-dichlorobenzoyl)amino]propionate: $^1$H-NMR (300 MHz, CDCl$_3$) 3.45 (3H, s), 3.70 (3H, s), 3.76 (3H, s), 5.24 (1H, m), 6.38 (1H, d, J=7.8 Hz), 7.23-7.34 (7H, m), 7.41 (2H, d, J=7.8 Hz), 7.53 (1H, dd, J=9.3, 2.7 Hz), 7.95 (1H, d, J=2.7 Hz).

Process 3 Hydrolysis

The compound obtained in Process 2 (20 mg) was treated by the same procedure as that of Process 4 of Example 6 to obtain the title compound (15 mg).

MS (ESI MH+): 559

CHNO: C27H21Cl3N2O5

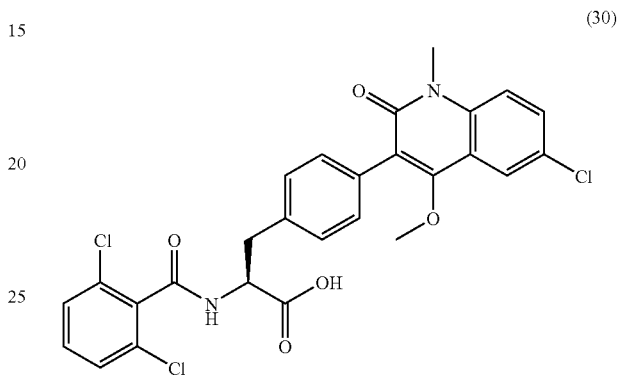

(30)

EXAMPLE 45

Synthesis of the Compound of the Following Formula (31)

Process 1 Synthesis of 1-methyl-4-propyl-2(1H)-quinolinone

Aniline (1 ml) and toluene (66 ml) were added to ethyl 3-oxohexanoate (2.1 ml) and stirred at 120° C. overnight. After removing the solvent, sulfuric acid (40 ml) was added to the residue and stirred at 80° C. for seven hours. The reaction solution was put into ice and adjusted to pH=3, and the precipitated crystals were filtered out. Methyl iodide (3 ml), potassium carbonate (1.9 g) and DMF (20 ml) were added to the residue and stirred at room temperature for 26 hours. After removing the solvent, the reaction mixture was diluted with dichloromethane, washed with 1N hydrochloric acid and saturated sodium bicarbonate water and dried over magnesium sulfate to remove the solvent. The residue was purified with a silica gel chromatography (dichloromethane-methanol) to obtain 1-methyl-4-propyl-2(1H)-quinolinone (800 mg).

MS (ESI MH+): 202

CHNO: C13H15NO

Process 2 Bromination

The compound obtained in Process 1 (800 mg) was brominated by the same procedure as that of Process 1 of Example 42 to obtain 3-bromo-1-methyl-4-propyl-2(1H)-quinolinone (400 mg).

MS (ESI MH+): 280

CHNO: C13H14BrNO

NMR data of 3-bromo-1-methyl-4-propyl-2(1H)-quinolinone: $^1$H-NMR (300 MHz, CDCl$_3$) 1.11 (3H, t, J=7.8 Hz), 1.70 (2H, m), 3.10 (2H, m), 3.80 (3H, s), 7.28 (1H, t, J=9.0 Hz), 7.39 (1H, d, J=8.7 Hz), 7.59 (1H, t, J=8.1 Hz), 7.78 (1H, d, J=6.0 Hz).

Process 3 Coupling, Removal of Boc group, Acylation and Hydrolysis

The compound obtained in Process 2 (300 mg) was treated by the same coupling, removal of Boc group, acylation and hydrolysis procedures as those of Processes 2 to 4 of Example 42 to obtain the title compound (223 mg).

MS (ESI MH+): 537

CHNO: C29H26Cl2N2O4

NMR data of the compound of Example 45: $^1$H-NMR (300 MHz, DMSO-$d_6$) 0.79 (3H, t, J=7.2 Hz), 1.48 (2H, m), 2.58 (2H, m), 2.93-3.01 (1H, m), 3.16-3.22 (1H,m), 3.62 (3H, s), 4.72 (1H, m), 7.08 (2H, d, J=7.5 Hz), 7.28-7.44 (6H, m), 7.54 (1H, d, J=8.4 Hz), 7.62 (1H, t, J=7.5 Hz), 7.86 (1H, d, J=8.4 Hz), 9.13 (1H, d, J=8.1 Hz).

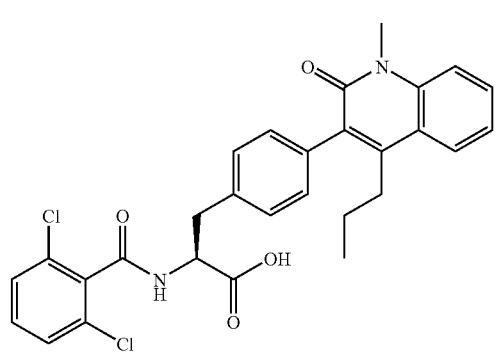

(31)

The same procedure as that of Example 45 synthesizes (2S)-2-[(2,6-dichlorobenzoyl)amino]-3-[4-(4-ethyl-1-methyl-2-oxo-1,2-dihydro-3-quinolinyl)phenyl]propanoic acid and (2S)-3-[4-(4-butyl-1-methyl-2-oxo-1,2-dihydro-3-quinolinyl)phenyl]-2-[(2,6-dichlorobenzoyl)amino]propanoic acid.

EXAMPLE 46

Synthesis of the Compound of the Following Formula (32)

Process 1 Hydrogenation 7.5% Pd/C (5 mg) and ethyl acetate (5 ml) were added to N-(2,6-dichlorobenzoyl)-4-(4-methylene-1-oxy-3,4-dihydro-2(1H)-isoquinolinyl) phenylalanine (10 mg) obtained as a by-product material in Process 4 of Example 23. The mixture was stirred at room temperature for five hours under the hydrogen atmosphere. After Celite filtration, the solvent was removed and the residue was purified with a reverse phase HPLC (water-acetonitrile, each containing 0.1% TFA) to obtain the objective compound (1 mg).

MS (ESI MH+): 497

CHNO: C26H22Cl2N2O4

NMR data of the compound of Example 46: $^1$H-NMR (300 MHz, DMSO-$d_6$) 1.35 (3H, d), 2.90-4.10 (5H, m), 4.70 (1H, m), 7.20-7.60 (10H,m), 7.95 (1H, d), 9.10 (1H, d).

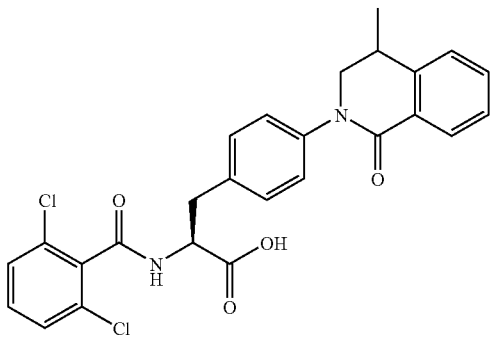

(32)

EXAMPLE 47

Synthesis of the Compound of the Following Formula (33)

Process 1 N-alkylation

An ethanol solution of hydrogen bromide (25%, 10 ml) was added to 1,4-dihydro-3H-isochromene-3-one (500 mg) and stirred at 70° C. overnight. After removing the solvent, the residue was roughly purified with a silica gel chromatography (hexane-ethyl acetate) to obtain a crude material of [2-(bromomethyl)phenyl]ethyl acetate. Methyl 3-(4-aminophenyl)-2-[(2,6-dichlorobenzoyl)amino]propionate (520 mg), triethylamine (490 μl) and DMF (5 ml) were added to the crude material and stirred at 125° C. for six hours. After removing the solvent, the residue was purified with a silica gel chromatography (hexane-ethyl acetate) to obtain methyl 2-[(2,6-dichlorobenzoyl)amino]-3-(4-{[2-(2-ethoxy-2-oxoethyl) benzyl]amino}phenyl) propionate (510 mg).

MS (ESI MH+): 542

CHNO: C28H28Cl2N2O5

Process 2 Cyclization, Hydrolysis

The compound obtained in Process 1 (240 mg) was cyclized and hydrolyzed under the same conditions as those of Process 4 of Example 6 to obtain the title compound (22 mg).

MS (ESI MH+): 483

CHNO: C25H20Cl2N2O4

NMR data of the compound of Example 47: $^1$H-NMR (300 MHz, CDCl$_3$) 3.30 (2H, m), 3.82 (2H, s), 4.82 (2H, s), 5.23 (1H, m), 6.67 (1H, m), 7.17-7.36 (11H, m).

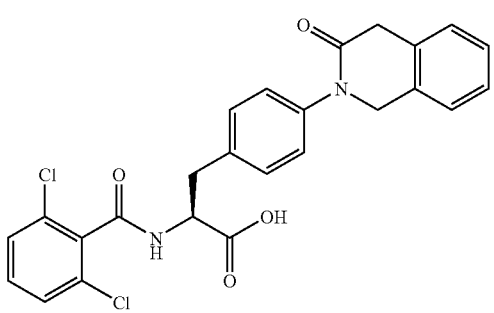

(33)

EXAMPLES 48 TO 72

Synthesis of the compounds of the following Table 11

The ester compounds of Examples 48 to 72 of Table 11 were obtained as intermediates, which were synthesized in the synthesizing processes of corresponding carboxylic acid compounds in Examples of the present specification. They were also obtained by esterifying the corresponding carboxylic acid compounds with well-known methods. The esterification was done by the method comprising the step of reacting a carboxylic acid compound(s) with thionyl chloride in methanol or by the method comprising the step of reacting trimethylsilyldiazomethane in various solvents.

TABLE 11

| Example | Structure | $[M + H]^+$ |
|---|---|---|
| 48 | 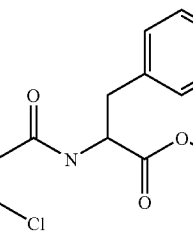 | 509 |
| 49 | 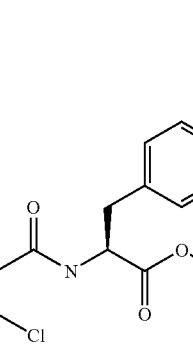 | 539 |
| 50 | 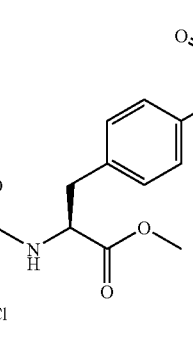 | 566* |
| 51 | 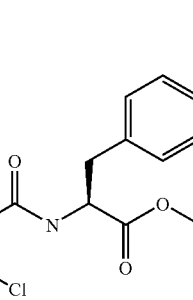 | 523 |

TABLE 11-continued

| Example | Structure | [M + H]+ |
|---|---|---|
| 52 | 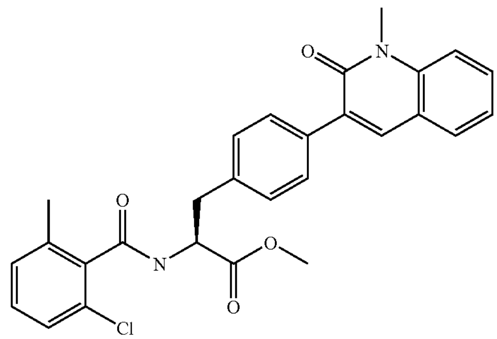 | 489 |
| 53 | 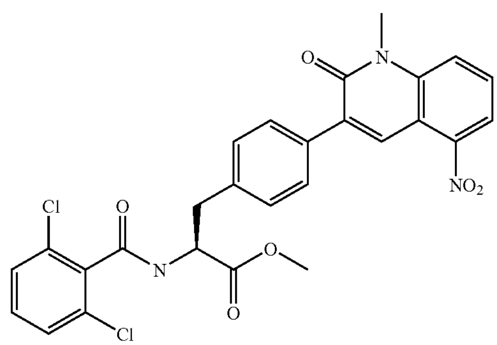 | 554 |
| 54 | 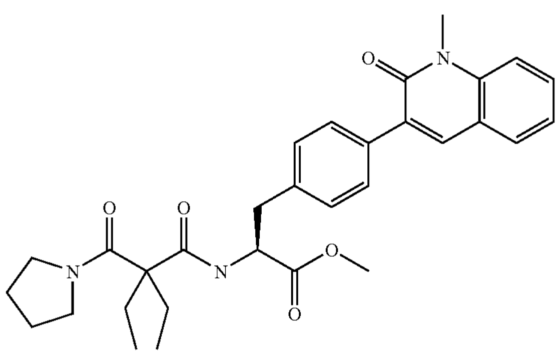 | 532 |
| 55 | 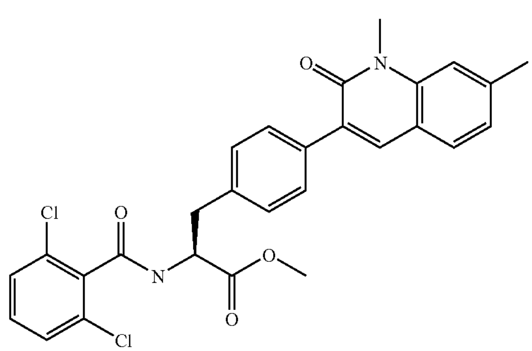 | 523 |

TABLE 11-continued
| Example | Structure | [M + H]+ |
|---|---|---|
| 56 | 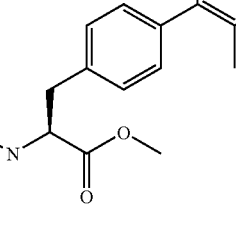 | 523 |
| 57 | 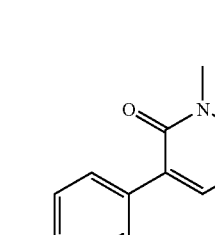 | 524 |
| 58 | 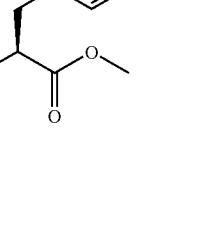 | 539 |
| 59 | 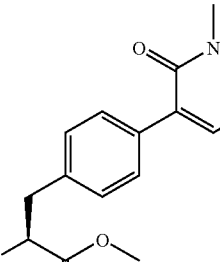 | 552 |

TABLE 11-continued

| Example | Structure | [M + H]+ |
|---|---|---|
| 60 | 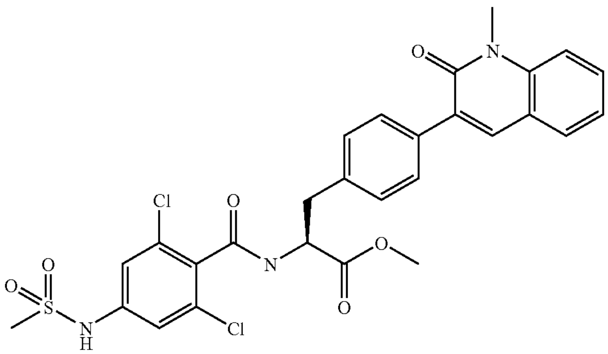 | 602 |
| 61 | 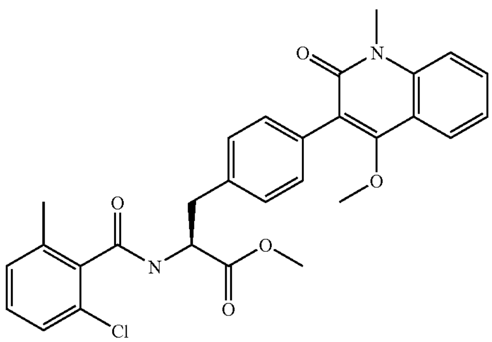 | 519 |
| 62 | 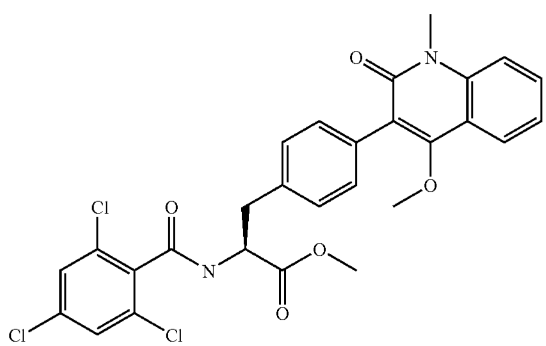 | 573 |
| 63 | 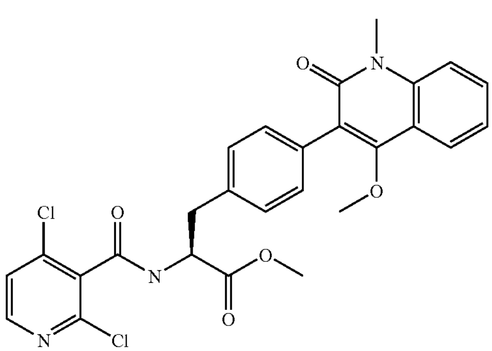 | 540 |

TABLE 11-continued

| Example | Structure | [M + H]+ |
|---|---|---|
| 64 | 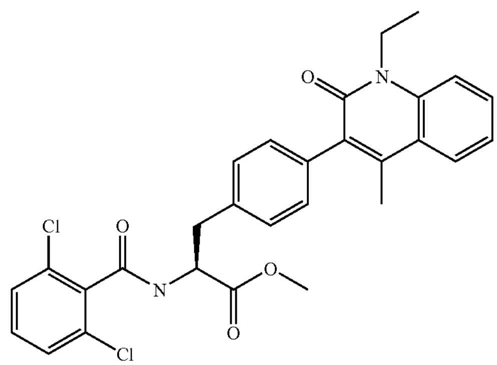 | 537 |
| 65 | 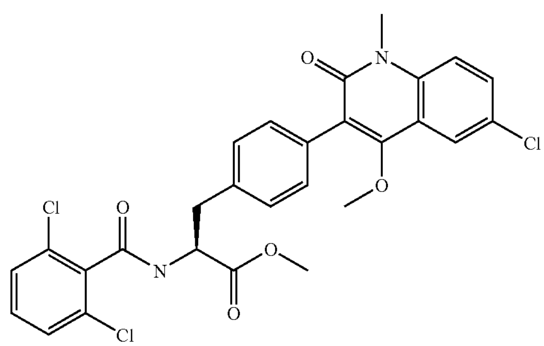 | 559 |
| 66 | 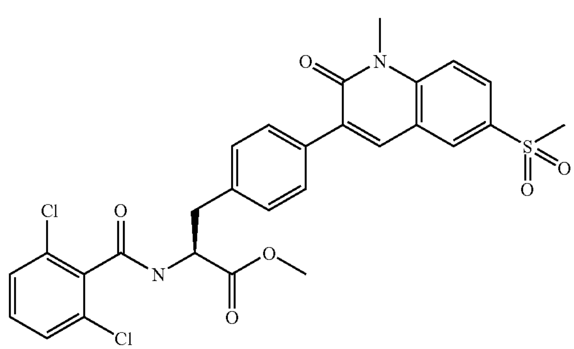 | 587 |
| 67 | 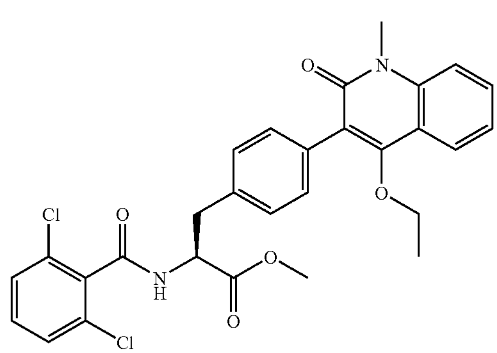 | 553 |

TABLE 11-continued
| Example | Structure | [M + H]+ |
|---|---|---|
| 68 | 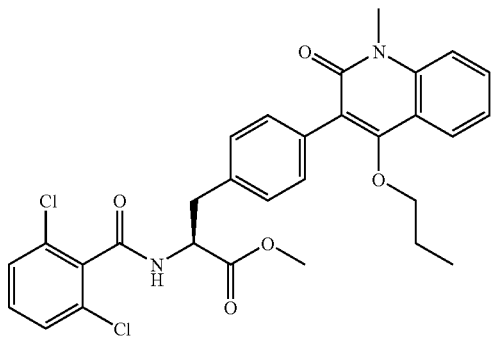 | 567 |
| 69 | 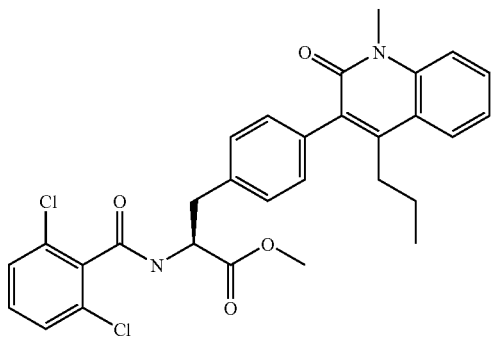 | 551 |
| 70 | 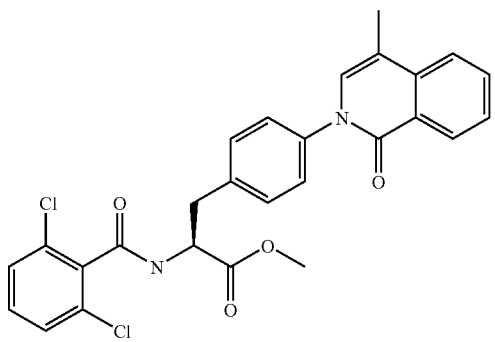 | 509 |
| 71 | 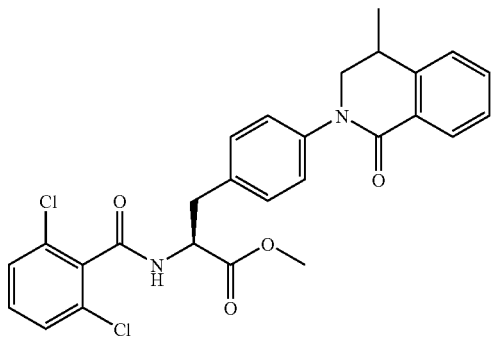 | 511 |

TABLE 11-continued

| Example | Structure | [M + H]+ |
|---|---|---|
| 72 | 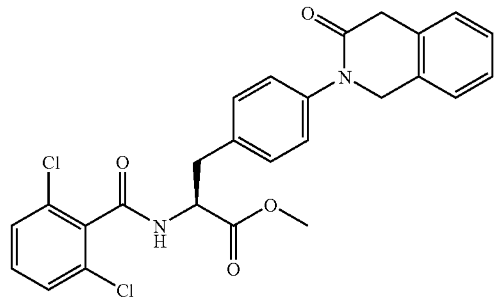 | 497 |

*: represents M+

REFERENTIAL EXAMPLE 1

Synthesis of 3-bromo-6-chloroquinoline

The synthesis was done by the same procedure as that of J. J. Eisch (J. Org. Chem. Vol. 27, p.1318, 1962). Bromine (79 μl) and carbon tetrachloride (2 ml) were added to 6-chloroquinoline (250 mg) and stirred at 90° C. for two hours. Pyridine (123 μl) was added to the reaction solution and stirred at the same temperature for 16 hours. The reaction solution was concentrated and purified with a silica gel chromatography (hexane-ethyl acetate) to obtain the title compound (250 mg).

REFERENTIAL EXAMPLE 2

Synthesis of 6-chloro-2,4-quinolinediol

The synthesis was done by the same procedure as that of D. R. Buckle (J. Med. Chem. Vol. 18, p.726, 1975). This synthesizing method can apply to that of 2,4-quinolinediol having other substituents on the fifth to eighth positions.

EXAMPLE 9

VCAM Antagonist Activity (VCAM-1/α4 β1 Binding Assay)

The capacity of a test substance antagonistic to the binding of cell strain Jurkat (ATCC TIB-152) of human T cells, known to express integrin α4 β1, to VCAM-1 was determined.

100 μl/well of a solution (500 ng/ml) of recombinant human VCAM-1 (R & D systems) solution diluted with buffer A (0.1 M NaHCO$_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace (Dainippon Pharmaceutical Co., Ltd.) with PBS to ¼ concentration was added in an amount of 150 μl/well. After the incubation at room temperature for 1 hour, buffer B was removed and the plate was washed with PBS once.

Jurkat cells were washed with Dulbecco modified Eagle medium (SIGMA, hereinafter referred to as "DMEM") twice and then incubated in DMEM containing 10 μg/ml of Calcein-AM (Wako Pure Chemical Industries, Ltd.) at 37° C. in dark place for 30 minutes to label with fluorescence. The cells were again suspended in a binding buffer (20 mM HEPES, DMEM containing 0.1% BSA).

50 μl of a test substance of various concentrations obtained by the dilution with the binding buffer was added to the plate. Immediately thereafter, 50 μl (final volume: 100 μl/well) of the fluorescent Jurkat cells (4×10$^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-1abel counter) (filter excitation wave length: 485 nm, emission wave length: 535 nm). The fluorescent strength thus obtained is proportional to the number of Jurkat cells bound to VCAM-1 and remaining on the plate. The binding rate of each test material in various concentrations was determined while the fluorescent strength of the test material-free well was determined to be 100%. The concentration IC$_{50}$ for the 50% binding inhibition was calculated.

The obtained test results are shown in Table 5

EXAMPLE 10

VCAM Antagonistic Activity (VCAM-1/α4β7 Binding Assay)

The capacity of a test substance antagonistic to the binding of lymphoma cell strain RPMI-8866 of human B cells, known to express integrin α4 β7, to VCAM-1 was determined.

100 μl/well of a solution (500 ng/ml) of recombinant human VCAM-1 (R & D systems) solution diluted with buffer A (0.1 M NaHCO$_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace (Dainippon Pharmaceutical Co., Ltd.) with PBS to ¼ concentration was added in an amount of 150 μl/well. After the incubation at room temperature for 1 hour, buffer B was removed and the plate was washed with PBS once.

RPMI-8866 cells were incubated in Dulbecco modified Eagle medium containing 10 μg/ml of Calcein-AM (Wako Pure Chemical Industries, Ltd.) (SIGMA, hereinafter referred to as "DMEM") at 37° C. for 30 minutes to label with fluorescence. The cells were again suspended in a binding buffer (20 mM HEPES, DMEM containing 0.1% BSA) containing 4 mM of $MnCl_2$.

50 μl of a test substance of various concentrations obtained by the dilution with the binding buffer was added to the plate. Immediately thereafter, 50 μl (final volume: 100 μl/well) of the fluorescent RPMI-8866 cells ($4\times10^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of RPMI-8866 cells bound to VCAM-1 and remaining on the plate. The binding rate of each test material in various concentrations was determined while the fluorescent strength of the test material-free well was determined to be 100%. The concentration $IC_{50}$ for the 50% binding inhibition was calculated.

The obtained test results are shown in Table 5.

TABLE 5

Results of the determination of VCAM antagonistic activity (IC50, nmol/L)

| Example | α4β7 | α4β1 |
|---|---|---|
| 1 | 90 | 620 |
| 6 | 3.5 | 44 |
| 8 | 18 | 320 |
| 14 | 3.3 | 150 |
| 19 | 11 | 290 |
| 21 | 2.4 | 190 |
| 22 | 150 | |
| 23 | 35 | |
| 26 | 44 | |
| 30 | 3.9 | 64 |
| 31 | 3.0 | 47 |
| 33 | 21 | 255 |
| 40 | 6.5 | 115 |
| 41 | 4.5 | 74 |
| 42 | 4.1 | 52 |
| 43 | 10 | 178 |
| 44 | 11 | 168 |
| 45 | 7.3 | 37 |
| 46 | 67 | |
| 47 | 97 | |

It is thus apparent that the new phenylalanine derivatives of the present invention exhibited an excellent α4-integrin inhibiting activity.

Therefore, the new phenylalanine derivatives of the present invention provide a therapeutic agent or preventive agent for diseases in which α4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection. The above-described inflammatory bowel diseases include Crohn's disease and ulcerative colitis. In this purpose, the compound of the present invention has high bioavailability and/or blood level when administered orally. Therefore, an oral administration of a drug is effective.

The compound of the present invention also has high stability in acidic or alkaline solution and is effective, for example, as it is possible to apply to various dosage forms.

What is claimed is:
1. Phenylalanine derivatives of the following general formula (1) or pharmaceutically acceptable salts thereof:

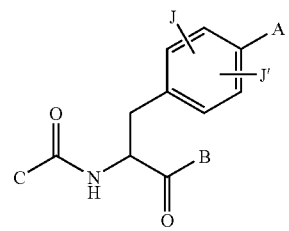

(1)

wherein A represents one of the following general formulae (2), (2-2), and (2-4) and:

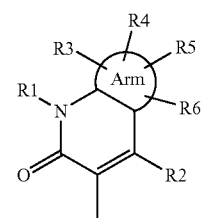

(2)

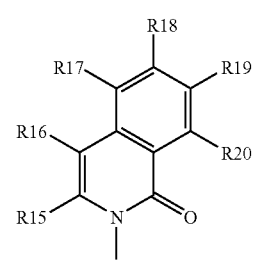

(2-2)

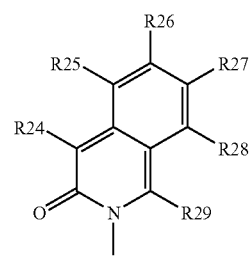

(2-4)

wherein Arm represents a cyclic alkyl group or an aromatic ring containing 0,

R1 represents a hydrogen atom, an alkyl group which may have a substituent(s), a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower hydroxyalkyl group, a lower halogenoalkyl group, a cycloalkyl group which may contain a hetero atom(s) in the ring thereof, an alkenyl group which may have a substituent(s), a lower hydroxyalkenyl group, a lower halogenoalkenyl group, an alkynyl group which may have a substituent(s), an aryl group, a heteroaryl group, a lower alkyloxycarbonyl group, a substituted or unsubstituted carbamoyl group, a lower alkanoyl group, an aroyl group, a lower alkylsulfonyl group or a substituted or unsubstituted sulfamoyl group, R2 to R6 and R10 to R33 may be the same or different from one another and each represents a hydrogen atom, an alkyl group which may have a substituent(s), a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower hydroxyalkyl group, a lower halogenoalkyl group, a cycloalkyl group which may contain a hetero atom(s) in the ring thereof, an alkenyl group which may have a substituent(s), a lower hydroxyalkenyl group, a lower halogenoalkenyl group, an alkynyl group which may have a substituent(s), an aryl group, a heteroaryl group, a lower alkyloxycarbonyl group, a substituted or unsubstituted carbamoyl group, a lower alkanoyl group, an aroyl group, a lower alkylsulfonyl group, a substituted or unsubstituted sulfamoyl group, a halogen atom, a hydroxyl group, a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a lower hydroxylalkoxyl group, a lower halogeno alkoxyl group, a lower halogenoalkylthio group, a cycloalkyloxy group which may contain a hetero atom(s) in the ring thereof, an aryloxy group, a heteroaryloxy group, a nitro group, a cyano group, a substituted or unsubstituted amino group, carboxyl group or a trialkylammonium group, B represents a hydroxyl group, an alkoxyl group, a substituted lower alkoxyl group or a hydroxylamino group, in cases where A represents the general formula (2), (2-2), or (2-4), C represents an aryl group, a heteroaryl group, a cycloalkyl group which may contain a hetero atom(s) in the ring thereof, a lower alkyl group substituted with a cycloalkyl group(s) which may contain a hetero atom(s) in the ring thereof, a lower alkyl group substituted with an aryl group(s), a lower alkyl group substituted with a heteroaryl group(s), an alkyl group which may have a substituent(s), a lower hydroxyalkyl group, a lower halogenoalkyl group, an alkenyl group which may have a substituent(s), a lower hydroxyalkenyl group, a lower halogenoalkenyl group, an alkynyl group which may have a substituent(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxylalkoxyl group, a lower halogeno alkoxyl group, a substituted or unsubstituted amino group or a lower alkylthio group, or C also represents an organic group of the following general formula (3):

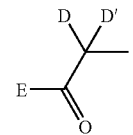

(3)

wherein D and D' may be the same or different from one another and each represents a hydrogen atom, an alkyl group which may have a substituent(s), an alkenyl group which may have a substituent(s) or an alkynyl group which may have a substituent(s), and D and D' may be bonded together to form a ring which may contain one or two oxygen, nitrogen or sulfur atoms, E represents an amino group or a lower alkylamino group which may have a substituent(s), including an amino group(s) having two substituents wherein the substituents are bonded together to form a ring, J and J' may be the same or different from one another and each represents a hydrogen atom, a halogen atom, a lower alkyl group, a lower alkyloxy group, a nitro group, an amino group or a hydroxyl group.

2. The phenylalanine derivatives or pharmaceutically acceptable salts thereof according to claim 1, wherein A represents the general formula (2) wherein Arm represents a cyclic alkyl group or an aromatic ring containing 0, R1 represents a hydrogen atom, an alkyl group which may have a substituent(s), a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower hydroxyalkyl group, a lower halogenoalkyl group, a cycloalkyl group which may contain a hetero atom(s) in the ring thereof, an alkenyl group which may have a substituent(s), a lower hydroxyalkenyl group, a lower halogenoalkenyl group, an alkynyl group which may have a substituent(s), an aryl group, a heteroaryl group, a lower alkyloxycarbonyl group, a substituted or unsubstituted carbamoyl group, a lower alkanoyl group, an aroyl group, a lower alkylsulfonyl group or a substituted or unsubstituted sulfamoyl group, R2, R3, R4, R5 and R6 may be the same or different from one another and each represents a hydrogen atom, an alkyl group which may have a substituent(s), a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower hydroxyalkyl group, a lower halogenoalkyl group, a cycloalkyl group which may contain a hetero atom(s) in the ring thereof, an alkenyl group which may have a substituent(s), a lower hydroxyalkenyl group, a lower halogenoalkenyl group, an alkynyl group which may have a substituent(s), an aryl group, a heteroaryl group, a lower alkyloxycarbonyl group, a substituted or unsubstituted carbamoyl group, a lower alkanoyl group, an aroyl group, a lower alkylsulfonyl group, a substituted or unsubstituted sulfamoyl group, a halogen atom, a hydroxyl group, a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a lower hydroxylalkoxyl group, a lower halogeno alkoxyl group, a lower halogenoalkylthio group, a cycloalkyloxy group which may contain a hetero atom(s) in the ring thereof, an aryloxy group, a heteroaryloxy group, a nitro group, a cyano group, a substituted or unsubstituted amino group, carboxyl group or a trialkylammonium group, B represents a hydroxyl group, an alkoxyl group, a substituted lower alkoxyl group or a hydroxylamino group, C represents an aryl group, a heteroaryl group, a cycloalkyl group which may contain a hetero atom(s) in the ring thereof, a lower alkyl group substituted with a cycloalkyl group(s) which may contain a hetero atom(s) in the ring thereof, a lower alkyl group substituted with an aryl group(s), a lower alkyl group substituted with a heteroaryl group(s), an alkyl group which may have a substituent(s), a lower hydroxyalkyl group, a lower halogenoalkyl group, an alkenyl group which may have a substituent(s), a lower hydroxyalkenyl group, a lower halogenoalkenyl group, an alkynyl group which may have a substituent(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxylalkoxyl group, a lower halogeno alkoxyl group, a substituted or unsubstituted amino group or a lower alkylthio group, or C represents an organic group of the above general formula (3), wherein D and D' may be the same or different from one another and each represents a hydrogen atom, an alkyl group which may have a substituent(s), an alkenyl group which may have a substituent(s) or an alkynyl group which may have a substituent(s), and D and D' may be bonded together to form a ring which may contain one or two oxygen, nitrogen or sulfur atoms, E represents an amino group or a lower alkylamino group which may have a substituent(s), including an amino group(s) having two substituents wherein the substituents are bonded together to form a ring, and J and J' may be the same or different from one another and each represents a hydrogen atom, a halogen atom, a lower alkyl group, a lower alkyloxy group, a nitro group, an amino group or a hydroxyl group.

3. The phenylalanine derivatives or pharmaceutically acceptable salts thereof according to claim 2, wherein, in the general formula (1), A represents the above general formula (2) wherein Arm is a benzene ring, R1 is a lower alkyl group, R2 is a lower alkyl group, a lower alkoxyl group or a hydrogen atom, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, an amino group substituted with a lower alkanoyl group, an amino group substituted with a lower alkyloxycarbonyl group, a lower alkylsulfonyl groups or a lower trialkylammonium group.

4. The phenylalanine derivatives or pharmaceutically acceptable salts thereof according to claim 2, wherein B represents a hydroxyl group or a lower alkoxyl group.

5. The phenylalanine derivatives or pharmaceutically acceptable salts thereof according to claim 2, wherein C represents the above general formula (3) or the following general formulae (3-1), (3-2), (3-3) or (3-4):

(3-1)

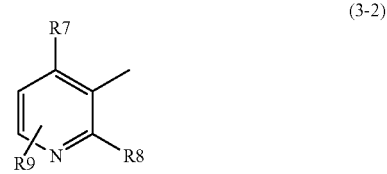

(3-2)

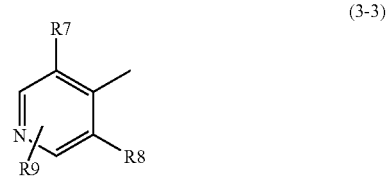

(3-3)

(3-4)

wherein R7 represents a halogen atom or methyl group, R8 represents a halogen atom, methyl group, trifluoromethyl group, methoxy group or a hydrogen atom, R9 represents a hydrogen atom, halogen atom, hydroxyl group, lower alkyl group, cycloalkyl group which may contain a hetero atom(s) in the ring thereof, lower alkoxyl group, lower alkylthio group, lower halogenoalkyl group, lower halogenoalkoxyl group, lower halogenoalkylthio group, nitro group, cyano group, amino group, amino group substituted with a lower alkyl group(s), lower trialkylammonium group, lower alkylsulfonylamino group or tetrazolyl group.

6. The phenylalanine derivatives or pharmaceutically acceptable salts thereof according to claim 2, wherein, in the general formula (1), A represents the above general formula (2) wherein Arm is a benzene ring, R1 is a lower alkyl group, R2 is a lower alkyl group, a lower alkoxyl group or a hydrogen atom, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B represents a hydroxyl group or a lower alkoxyl group, and C represents the above general formulae (3), (3-1), (3-2), (3-3) or (3-4).

7. The phenylalanine derivatives or pharmaceutically acceptable salts thereof according to claim 2, wherein, in the general formula (1), A represents the above general formula (2) wherein Arm is a benzene ring, R1 is a lower alkyl group, R2 is a lower alkyl group, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B represents a hydroxyl group or a lower alkoxyl group, C represents the above general formulae (3-1) or (3-2), and J and J' are a hydrogen atom.

8. The phenylalanine derivatives or pharmaceutically acceptable salts thereof according to claim 2, wherein, in the general formula (1), A represents the above general formula (2) wherein Arm is a benzene ring, R1 is a lower alkyl group, R2 is a lower alkoxyl group, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B represents a hydroxyl group or a lower alkoxyl group, C represents the above general formulae (3-1) or (3-2), and J and J' are a hydrogen atom.

9. The phenylalanine derivatives or pharmaceutically acceptable salts thereof according to claim 2, wherein, in the general formula (1), A represents the above general formula (2) wherein Arm is a benzene ring, R1 is a lower alkyl group, R2 is a hydrogen atom, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B represents a hydroxyl group or a lower alkoxyl group, C represents the above general formulae (3-1) or (3-2), and J and J' are a hydrogen atom.

10. The phenylalanine derivatives or pharmaceutically acceptable salts thereof according to claim 2, wherein, in the general formula (1), A represents the above general formula (2) wherein Arm is a benzene ring, R1 is a methyl group or an ethyl group, R2 is a methoxy group, an ethoxy group, a propoxy group, a methyl group, an ethyl group, a propyl group or a butyl group, R3, R4, R5 and R6 may be the same or different from each other and each represents a hydrogen atom, a halogen atom, a lower alkyl group, a lower halogenoalkyl group, a hydroxyl group, a lower alkoxyl group, a nitro group, a cyano group, an amino group, an amino group substituted with a lower alkyl group, a lower alkylsulfonyl groups or a lower trialkylammonium group, B represents a hydroxyl group, C represents the above general formulae (3-1) or (3-2) wherein R7 represents a halogen atom or methyl group, R8 represents a halogen atom, R9 represents a hydrogen atom, halogen atom, hydroxyl group, lower alkyl group, lower alkoxyl group, lower alkylthio group, lower halogenoalkyl group, lower halogenoalkoxyl group, lower halogenoalkylthio group, nitro group, cyano group, amino group, lower alkylamino group, trialkylammonium group, methanesulfonyl amino group or tetrazolyl group, and J and J' are a hydrogen atom.

11. Phenylalanine derivatives of the following general formula (22) or pharmaceutically acceptable salts thereof:

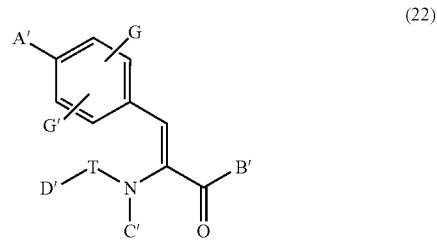

(22)

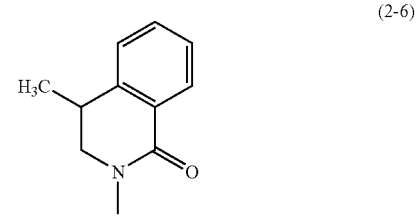

(2-6)

B represents a hydroxyl group or a lower alkoxyl group,

C represents the general formulae (3-1), (3-2) or (3-3):

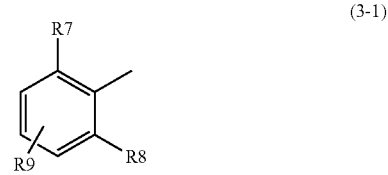

(3-1)

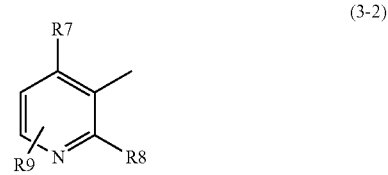

(3-2)

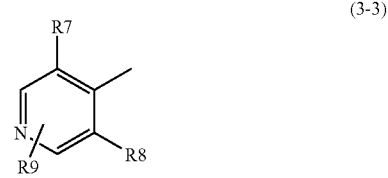

(3-3)

R7 represents a halogen atom or a methyl group, R8 represents a halogen atom, R9 represents a hydrogen atom, a halogen atom, a hydroxyl group, a lower alkyl group, a lower alkoxyl group, a lower alkylthio group, a lower halogenoalkyl group, a lower halogeno alkoxyl group, a lower halogenoalkylthio group, a nitro group, a cyano group, an amino group, a lower alkylamino group, a trialkylammonium group, a methansulfonylamino group or a tetrazolyl group, and J and J' represent a hydrogen atom.

12. The phenylalanine derivatives or pharmaceutically acceptable salts thereof according to claim 1, wherein, in the general formula (1), A represents the following general formula (2-7):

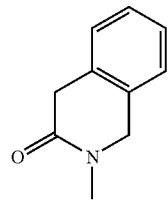
(2-7)

B represents a hydroxyl group or a lower alkoxyl group,

C represents the general formulae (3-1), (3-2) or (3-3):

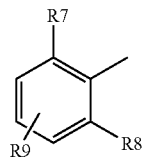
(3-1)

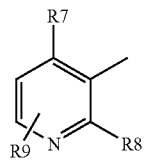
(3-2)

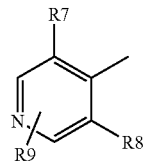
(3-3)

R7 represents a halogen atom or a methyl group, R8 represents a halogen atom, R9 represents a hydrogen atom, a halogen atom, a hydroxyl group, a lower alkyl group, a lower alkoxyl group, a lower alkylthio group, a lower halogenoalkyl group, a lower halogeno alkoxyl group, a lower halogenoalkylthio group, a nitro group, a cyano group, an amino group, a lower alkylamino group, a trialkylammonium group, a methansulfonylamino group or a tetrazolyl group, and J and J' represent a hydrogen atom.

13. The phenylalanine derivatives or pharmaceutically acceptable salts thereof according to claim 11, wherein, in the general formula (1), A represents the general formula (2-6), B represents a hydroxyl group or a lower alkoxyl group, C represents the above general formula (3-1) wherein R7 represents a chlorine atom, R8 represents a chlorine atom, R9 represents a hydrogen atom, and J and J' are a hydrogen atom.

14. The phenylalanine derivatives or pharmaceutically acceptable salts thereof according to claim 12, wherein, in the general formula (1), A represents the general formula (2-7), B represents a hydroxyl group or a lower alkoxyl group, C represents the general formula (3-1) wherein R7 represents a chlorine atom, R8 represents a chlorine atom, R9 represents a hydrogen atom, and J and J' are a hydrogen atom.

* * * * *

UNITED STATES PATENT AND TRADEMARK OFFICE
CERTIFICATE OF CORRECTION

PATENT NO.      : 7,250,516 B2
APPLICATION NO. : 10/866260
DATED           : July 31, 2007
INVENTOR(S)     : Tatsuya Okuzumi et al.

It is certified that error appears in the above-identified patent and that said Letters Patent is hereby corrected as shown below:

Column 49, line 34, "150 mm" should read -- "50 mm--.

Column 52, line 22, "1-hyrdoxy" should read --1-hydroxy--.

Delete Claim 11 in its entirety and replace with the following:

--11. The phenylalanine derivatives or pharmaceutically acceptable salts thereof according to claim 1, wherein, in the general formula (1), A represents the following general formula (2-6):

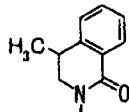

(2-6)

B represents a hydroxyl group or a lower alkoxyl group,
C represents the general formulae (3-1), (3-2) or (3-3):

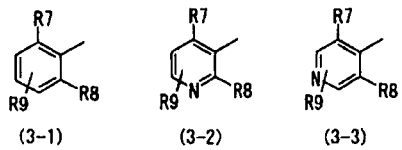

R7 represents a halogen atom or a methyl group, R8 represents a halogen atom, R9 represents a hydrogen atom, a halogen atom, a hydroxyl group, a lower alkyl group, a lower alkoxyl group, a lower alkylthio group, a lower halogenoalkyl group, a lower halogeno alkoxyl group, a lower halogenoalkylthio group, a nitro group, a cyano group, an amino group, a lower alkylamino group, a trialkylammonium group, a methansulfonylamino group or a tetrazolyl group, and J and J' represent a hydrogen atom.--.

Signed and Sealed this
Twelfth Day of April, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,250,516 B2 | |
| APPLICATION NO. | : 10/866260 | |
| DATED | : July 31, 2007 | |
| INVENTOR(S) | : Tatsuya Okuzumi et al. | |

It is certified that error appears in the above-identified patent and that said Letters Patent is hereby corrected as shown below:

Column 49, line 34, "150 mm" should read -- "50 mm --.

Column 52, line 22, "1-hyrdoxy" should read -- 1-hydroxy --.

Column 96, Lines 1-67, Delete Claim 11 in its entirety and replace with the following:

-- 11. The phenylalanine derivatives or pharmaceutically acceptable salts thereof according to claim 1, wherein, in the general formula (1), A represents the following general formula (2-6):

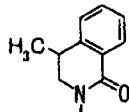

(2-6)

B represents a hydroxyl group or a lower alkoxyl group,
C represents the general formulae (3-1), (3-2) or (3-3):

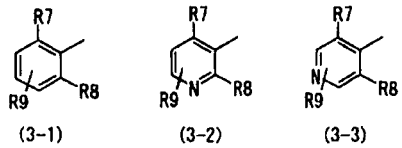

R7 represents a halogen atom or a methyl group, R8 represents a halogen atom, R9 represents a hydrogen atom, a halogen atom, a hydroxyl group, a lower alkyl group, a lower alkoxyl group, a lower alkylthio group, a lower halogenoalkyl group, a lower halogeno alkoxyl group, a lower halogenoalkylthio group, a nitro group, a cyano group, an amino group, a lower alkylamino group, a trialkylammonium group, a methansulfonylamino group or a tetrazolyl group, and J and J' represent a hydrogen atom. --.

This certificate supersedes the Certificate of Correction issued April 12, 2011.

Signed and Sealed this
Tenth Day of May, 2011

David J. Kappos
*Director of the United States Patent and Trademark Office*